(12) United States Patent (10) Patent No.: US 8,142,746 B2
Reyes et al. (45) Date of Patent: Mar. 27, 2012

(54) SEPARATION OF CARBON DIOXIDE FROM METHANE UTILIZING ZEOLITIC IMIDAZOLATE FRAMEWORK MATERIALS

(75) Inventors: Sebastian C. Reyes, Branchburg, NJ (US); Jose G. Santiesteban, legal representative, Hellertown, PA (US); Zheng Ni, Clinton, NJ (US); Charanjit S. Paur, South Bound Brook, NJ (US); Pavel Kortunov, Flemington, NJ (US); John Zengel, Clinton, NJ (US); Harry W. Deckman, Clinton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 12/321,752

(22) Filed: Jan. 23, 2009

(65) Prior Publication Data

US 2009/0211441 A1 Aug. 27, 2009

Related U.S. Application Data

(60) Provisional application No. 61/066,550, filed on Feb. 21, 2008.

(51) Int. Cl.
*B01D 53/04* (2006.01)
*B01D 53/02* (2006.01)
*B01D 53/047* (2006.01)
*B01J 8/02* (2006.01)
*C01B 33/20* (2006.01)
*C01B 31/20* (2006.01)
*C01B 39/02* (2006.01)
*C01B 39/04* (2006.01)
*C07C 9/04* (2006.01)

(52) U.S. Cl. .............. 423/213.2; 423/220; 423/230; 423/235; 423/236; 423/239.1; 423/239.2; 423/245.1; 423/700; 423/701; 423/702; 423/704; 423/705; 423/706

(58) Field of Classification Search ............ 423/213.2, 423/220, 230, 235, 236, 239.1, 239.2, 245.1, 423/700, 701, 702, 704, 705, 706
See application file for complete search history.

(56) References Cited

U.S. PATENT DOCUMENTS 3,885,927 A 5/1975 Sherman et al.
(Continued)

FOREIGN PATENT DOCUMENTS

DE 2926524 6/1979
(Continued)

OTHER PUBLICATIONS

Watson, J.T.R., "Mean velocity, free path and size of molecules 2.2.4." National Physical Laboratory (2010). Visited Jun. 22, 2011 at http://www.kayelaby.npl.co.uk/general_physics/2_2/2_2_4.html.*

(Continued)

*Primary Examiner* — Stuart Hendrickson
*Assistant Examiner* — Daniel Berns

(57) ABSTRACT

The present invention relates to the selective separation of carbon dioxide ("$CO_2$") from methane ("$CH_4$") in streams containing both carbon dioxide and methane utilizing a zeolitic imidazolate framework ("ZIF") material. Preferably, the stream to be separated is fed to the present process in a substantially gaseous phase. In preferred embodiments, the current invention is utilized in a process to separate carbon dioxide from natural gas streams preferably for sequestration of at least a portion of the carbon dioxide present in the natural gas.

21 Claims, 29 Drawing Sheets

ZIF-7 Isotherms for $CO_2$ AND $CH_4$ @ 301 K

U.S. PATENT DOCUMENTS

| | | | |
|---|---|---|---|
| 4,775,396 | A | 10/1988 | Rastelli et al. |
| 4,857,078 | A | 8/1989 | Watler |
| 4,869,883 | A | 9/1989 | Thorogood et al. |
| 5,171,333 | A | 12/1992 | Maurer |
| 5,642,630 | A * | 7/1997 | Abdelmalek et al. ............ 62/632 |
| 5,726,118 | A * | 3/1998 | Ivey et al. ...................... 502/417 |
| 5,753,011 | A | 5/1998 | Sircar et al. |
| 6,011,192 | A | 1/2000 | Baker et al. |
| 6,531,569 | B1 | 3/2003 | Tachiki et al. |
| 6,617,467 | B1 | 9/2003 | Muller et al. |
| 6,624,318 | B1 | 9/2003 | Muller et al. |
| 6,893,564 | B2 | 5/2005 | Mueller et al. |
| 6,929,679 | B2 | 8/2005 | Muller et al. |
| 6,930,193 | B2 | 8/2005 | Yaghi et al. |
| 7,056,482 | B2 | 6/2006 | Hakka et al. |
| 7,078,235 | B2 | 7/2006 | Spencer et al. |
| 7,196,210 | B2 | 3/2007 | Yaghi et al. |
| 7,202,385 | B2 | 4/2007 | Mueller et al. |
| 2002/0104435 | A1 | 8/2002 | Baker et al. |
| 2003/0004364 | A1 | 1/2003 | Yaghi et al. |
| 2003/0078311 | A1 | 4/2003 | Muller et al. |
| 2003/0148165 | A1 | 8/2003 | Muller et al. |
| 2003/0222023 | A1 | 12/2003 | Mueller et al. |
| 2004/0225134 | A1 | 11/2004 | Yaghi et al. |
| 2004/0249189 | A1 | 12/2004 | Mueller et al. |
| 2004/0265670 | A1 | 12/2004 | Muller et al. |
| 2005/0004404 | A1 | 1/2005 | Muller et al. |
| 2005/0124819 | A1 | 6/2005 | Yaghi et al. |
| 2005/0154222 | A1 | 7/2005 | Muller et al. |
| 2005/0192175 | A1 | 9/2005 | Yaghi et al. |
| 2006/0079725 | A1 | 4/2006 | Li et al. |
| 2006/0135824 | A1 | 6/2006 | Mueller et al. |
| 2006/0154807 | A1 | 7/2006 | Yaghi et al. |
| 2006/0185388 | A1 | 8/2006 | Muller et al. |
| 2006/0252641 | A1 | 11/2006 | Yaghi et al. |
| 2007/0068389 | A1 | 3/2007 | Yaghi |
| 2007/0202038 | A1 | 8/2007 | Yaghi et al. |
| 2008/0184883 | A1 | 8/2008 | Zhou et al. |

FOREIGN PATENT DOCUMENTS

| | | |
|---|---|---|
| EP | 0 700 708 A1 | 3/1996 |
| EP | 1 148 025 A1 | 10/2001 |
| EP | 0 790 263 B1 | 2/2002 |
| EP | 1 674 555 A1 | 12/2005 |
| EP | 1 383 775 B1 | 8/2006 |
| WO | WO 02/088148 A1 | 11/2002 |
| WO | WO 03/035717 A1 | 5/2003 |
| WO | WO 03/064030 A1 | 8/2003 |
| WO | WO 03/101975 A1 | 12/2003 |
| WO | WO 03/102000 A1 | 12/2003 |
| WO | WO 2004/037895 A1 | 5/2004 |
| WO | WO2004/101575 A2 | 11/2004 |
| WO | WO 2005/003069 A2 | 1/2005 |
| WO | WO 2005/003622 A1 | 1/2005 |
| WO | WO 2005/068474 A1 | 7/2005 |
| WO | WO 2006/028479 A1 | 3/2006 |
| WO | WO 2006/047423 A2 | 5/2006 |
| WO | WO 2006/050898 A1 | 5/2006 |
| WO | WO 2006/089908 A1 | 8/2006 |
| WO | WO 2006/110740 A2 | 10/2006 |
| WO | WO 2007/038508 A2 | 4/2007 |
| WO | WO 2007/101241 A2 | 9/2007 |

OTHER PUBLICATIONS

Hideki Hayashi, Adrien P. Cote, Hiroyasu Furukawa, Michael O'Keeffe, Omar M. Yaghi, "Zeolite A imidazolate frameworks,"Nature Materials, vol. 6, Jul. 2007, pp. 501-506.

Rahul Banerjee, Anh Phan, Bo Wang, Carolyn Knobler, Hiroyasu Furukawa, Michael O'Keefe, Omar M. Yaghi, "High-Throughput Synthesis of Zeolitic Imidazolate Frameworks and Application of CO2 Capture," Science, vol. 319, Feb. 15, 2008, pp. 939-943.

Kyo Sung Park et al.; "Exceptional Chemical and thermal stability of zeolitic imidazolate frameworks," PNAS, Jul. 5, 2006, vol. 103, No. 27, pp. 10186-10191.

Yun-Qi Tian et al.; "The Silica-Like Extended Polymorphism of Cobalt (II) Imidazolate Three-Dimensional Frameworks: X-ray Single Crystal Structures and Magnetic Properties," Chem. Eur. J. 2003, 9, pp. 5673-5685.

Yun-Qi Tian et al.; "[$Co_5(im)_{10}$•2MB]∞: A Metal-Organic Open-Framework with Zeolite-Like Topology," Angew. Chem. Int. Ed. 2002, 41, No. 8, pp. 1384-1386.

Xiao-Chun Huang et al., "Ligand-Directed Strategy for Zeolite-Type Metal-Organic Frameworks: Zinc(II) Imidazolates with Unusual Zeolitic Topologies," Angew. Chem. Int. Ed. 2006, 45, pp. 1557-1559.

Ziaochun Huang et al.; "[$Zn(bim)_x$] • $(H_2O)_{1.67}$: A metal-organic open-framework with sodalite topology"; Chinese Science Bulletin, vol. 48, No. 15, Aug. 2003, pp. 1531-1534.

Yun-Qi Tian et al.; "Design and Generation of Extended Zeolitic Metal-Organic Frameworks (ZMOFs): Syntheis and Crystal Structures of Zinc(ii) Imidazolate Polymers with Zeolitic Topologies"; Chem. Eur. J., 2007, 13, pp. 4146-4154.

Yun-Qi Tian et al.; "[$Co^{II}Cu^I{}_2(Im)_4$]∞: A Layered Bimetallic Imidazolate Polymer, the First Hydridized Cobalt (ii) Imidazolate," Z.Anorg. Allg. Chem., 2004, 630, pp. 1371-1373.

Yun-Qi Tian et al., "Determination of the Solvothermal Synthesis Mechanism of Metal Imidazolates by X-ray Single-Crystal Studies of a Photoluminescent Cadmium(II) Imidazolate and Its Imtermediate Involving Piperazine," Eur. J. Inorg. Chem., 2004, pp. 1039-1044.

Zhong-Lin Lu et al.; "Synthesis and crystal structure of an imidazolate-bridged dicopper tris(2-aminoethyl)amine complex"; Transition Met. Chem., 22, 1997, pp. 549-552.

Yun-Qi Tian et al.; "Two Polymorphs of Cobalt(II) Imidazolate Polymers Synthesized Solvothermally by Using One Organic Template N, N-Dimethylacetamide"; Inorg. Chem. 2004, 43, pp. 4631-4635.

Xiao-Chun Huang, Jie-Peng Zhang, Xiao-Ming Chen; "One-Dimensional Supramolecular Isomerism of Copper(I) and Silver(I) Imidazolates Based on theLigand Orientations," Crystal Growth & Design, 2006, vol. 6, No. 5, pp. 1194-1198.

Yunling Liu, Victor CH. Kravtsov, Randy Larsen, Mohamed Eddaoudi; "Molecular building blocks approach to the assembly of zeolite-like metal-organic frameworks (ZMOFs) with extra-large cavities"; Chem. Commun., 2006, pp. 1488-1490.

Philip L. Llewellyn et al.; "How Hydration Drastically Improves Adsorption Selectivity for $CO_2$ over CH4 in the Flexible Chromium Terephthlate MIL-53"; Angew. Chem. Int. Ed., 2006, 45, pp. 7751-7754.

Atsushi Kondo et al.; "Novel Expansion/Shrinkage Modulation of 2D Layered MOF Triggered by Clathrate Formation with $CO_2$ Molecules"; Nano Letters, 2006, vol. 6, No. 11, pp. 2581-2584.

Katharine Sanderson, "Space Invaders," news feature in Nature, vol. 448, Aug. 16, 2007, pp. 746-748.

* cited by examiner

Powder X-ray Diffraction Pattern of ZIF-7

Thermogravimetric Analyses of ZIF-7

Powder X-ray Diffraction Pattern of ZIF-9

Powder X-ray Diffraction Pattern of ZIF-1

Scanning Electron Microscopy Image of ZIF-9

Scanning Electron Microscopy Image of ZIF-1 (acetonitrile-exchanged)

Scanning Electron Microscopy Image of ZIF-1 (toluene-exchanged)

Scanning Electron Microscopy Image of ZIF-11

Scanning Electron Microscopy Image of ZIF-8

SEPARATION OF CARBON DIOXIDE FROM METHANE UTILIZING ZEOLITIC IMIDAZOLATE FRAMEWORK MATERIALS

This application claims the benefit of U.S. Provisional Application No. 61/066,550 filed Feb. 21, 2008.

FIELD OF THE INVENTION

The present invention relates to the selective separation of carbon dioxide ("$CO_2$") from methane ("$CH_4$") in streams containing both carbon dioxide and methane utilizing a zeolitic imidazolate framework ("ZIF") material. Preferably, the stream to be separated is fed to the present process in a substantially gaseous phase. In preferred embodiments, the current invention is utilized in a process to separate carbon dioxide from natural gas streams preferably for sequestration of at least a portion of the carbon dioxide present in the natural gas.

BACKGROUND OF THE INVENTION

Gas separation is an important process utilized in various industries, particularly in the production of fuels, chemicals, petrochemicals and specialty products. A gas separation can be accomplished by a variety of methods that, assisted by heat, solids, or other means, generally exploits the differences in physical and/or chemical properties of the components to be separated. For example, gas separation can be achieved by partial liquefaction or by utilizing a solid adsorbent material that preferentially retains or adsorbs a more readily adsorbed component relative to a less readily adsorbed component of the gas mixture, or by several other gas separation techniques known in the industry. One such commercially practiced gas separation process is pressure swing adsorption ("PSA"). PSA processes, when operated under certain conditions, allow a selective component or components in a gas mixture to be preferentially adsorbed within the pore structure of porous adsorbent materials relative to a second component or components in the gas mixture. The total amount adsorbed of each component in the material (i.e., the adsorption capacity) and the selectivity of the adsorption for a specific component over another component may often be improved by operating the process under specific pressure and temperature conditions since both pressure and temperature influence the adsorption loading of the components to a different extent. The efficiency of the PSA process may be further improved by the implementation of processing steps, such as the use of purge stream(s) that have optimally chosen composition, pressures and temperatures. However, relatively few adsorbent materials have separation selectivities, adsorption capacities and other beneficial properties (such as chemical and physical inertness and durability) so as to be able to function as commercially viable and cost-efficient adsorbents in a PSA process.

Some adsorbent materials are able to adsorb a greater amount of one component than another component under certain conditions. Certain components may not be selectively adsorbed or may not be adsorbed to an acceptable level that would lead to an economically viable process. However, if sizable differences in adsorption properties exist for selective components in an adsorbent material, PSA processes can be used to effectively separate certain component gases from a mixture. For example, if a gas mixture such as air is passed at some pressure and temperature through a vessel containing an adsorbent material that selectively adsorbs more oxygen than nitrogen, at least a portion of the oxygen contained in the feedstream will stay in the adsorbent and the gas coming out of the vessel will be enriched in nitrogen. When the bed reaches a selected fraction of its total capacity to adsorb oxygen, it can be regenerated by various pressure swing techniques, thereby releasing the adsorbed oxygen (and any other associated gas components), which can then be captured and isolated as a separate product stream. The adsorbent material which has now been "desorbed" of the oxygen can then be reused and the various steps of the PSA process cycle are repeated so as to allow a continuous operation.

However, finding suitable materials that specifically discriminate between difficult to separate gases in both an efficient and effective manner (that is that they have both good separation selectivity and a high adsorption capacity) are not easily found. Additionally, many adsorbent materials known in the art do not hold up well to the additional components in the streams or are unable to sustain the severe pressure and/or temperature conditions, including cyclic conditions, required by the processes. Therefore, commercially suitable, and more importantly, commercially valuable adsorbent materials are not very readily available. Researchers in the industry continually look for improved adsorbent materials, process configurations and operating conditions to make these separation processes economically viable.

An early teaching of a PSA process having a multi-bed system is found in U.S. Pat. No. 3,430,418 wherein a system having at least four beds is described. This '418 patent describes a cyclic PSA processing sequence that includes in each bed: (1) higher pressure adsorption with release of product effluent from the product end of the bed; (2) co-current depressurization to intermediate pressure with release of void space gas from the product end thereof; (3) countercurrent depressurization to a lower pressure; (4) purge; and (5) repressurization. The void space gas released during the co-current depressurization step is commonly employed for pressure equalization purposes and to provide purge gas to a bed at its lower desorption pressure. Another conventional PSA processes using three sorbent beds is disclosed in U.S. Pat. No. 3,738,087.

Another industrially important gas separation process is temperature swing adsorption ("TSA"). TSA processes, when operated under certain pressure and temperature conditions, allow some components to be selectively adsorbed over others within the pore structure of an adsorbent material. In this process, a stream containing components to be separated flows through an adsorbent material wherein one or more of the components are selectively adsorbed over another component or components. An effluent stream, reduced in concentration of the selectively adsorbed component(s) is obtained during this adsorption "stage" or "step" of the TSA process. In this process, after the adsorbent material has adsorbed a certain amount of the desired component(s), the temperature of the adsorbent is increased, and the selectively adsorbed component(s) is released, or desorbed from the adsorbent materials and can be collected separate from the effluent stream in this step of the overall TSA process cycle. By cyclically swinging the temperature of adsorbent beds, TSA processes can be used to separate components in a mixture when used with an adsorbent that selectively adsorbs one or more of the stream components in the feed mixture relative to one or more different stream components comprising the feed mixture.

PSA and TSA processes do not need to be mutually exclusive. A combined PSA/TSA process may be utilized, for example, by increasing the temperature of the adsorbent materials during the lower pressure purge step of a conventional PSA process to improve the desorption of the selectively adsorbed component(s) in the process. The bed temperature can then be reduced (or allowed to be reduced) during the adsorption portion of the PSA cycle to improve the adsorption characteristics and/or adsorption capacity of the material.

Besides using pressure and temperature to regenerate the adsorption bed, the adsorbent can be regenerated with a purge that is flowed through the adsorbent bed in a manner that displaces adsorbed molecules from the adsorbent. Processes that are conducted with this type of adsorbent regeneration technique are often called partial pressure purge displacement processes ("PPSA"). Processes such as PSA, TSA, purge displacement, and combination thereof are referred to herein as swing adsorption processes. These swing adsorption processes can be conducted with rapid cycles (i.e., cycles of short duration) in which case they are referred to as rapid cycle thermal swing adsorption (RCTSA), rapid cycle pressure swing adsorption (RCPSA), and rapid cycle partial pressure swing or displacement purge adsorption (RCPPSA) technologies.

Additionally, membrane separation processes can be used for the separation of gas components in a mixture. In a membrane separation process, one or more components of the mixed stream contact one side of a membrane material and a portion of the mixed stream permeates through the membrane and is retrieved from the other side of the membrane material as a "permeate" stream. In this process, the permeate stream has a higher concentration (in mole %, weight %, or volume % as defined by the process) of a select component than the mixed stream that initially contacts the membrane. A "retentate" stream is also obtained from the first side of the membrane which has a lower concentration (in mole %, weight %, or volume % as defined by the process) of a select component than the mixed stream that initially contacts the membrane. In this manner, a separation of components is made resulting in a higher value for the two separated streams (i.e., the retentate and the permeate streams) than the original mixed stream that is fed to the membrane separations process. The physical conditions on the permeate side of the membrane (for example pressure, temperature, and purge conditions) are chosen so that there is a gradient of chemical potential across the membrane that is favorable to drive the select component from the feed side to the permeate side of the membrane.

There is a need in the art for improved swing adsorption and/or membrane processes utilizing adsorbent materials for the selective separation of gaseous stream components. In particular, there is a need in the art for improved swing adsorption and/or membrane processes utilizing adsorbent materials for the selective separation and removal of carbon dioxide from methane in streams containing both carbon dioxide and methane.

United States Patent Publication No. US2007/0202038A1 discloses a family of materials which shall be referred to herein as zeolitic imidazolate frameworks (or "ZIF"'s) materials. This publication describes in detail the synthesis and structural and pore volume characterization of various ZIF materials. It includes the low temperature physisorption characterization ($N_2$ and $H_2$ at 77K and Ar at 87K) of selected ZIF structures but it does not disclose adsorption properties of these materials at pressure and temperature conditions that would be relevant to separation processes of gases and hydrocarbons of interest in industrial applications.

SUMMARY OF THE INVENTION

The present invention is a separation process utilizing ZIF-containing materials to effectively separate carbon dioxide, $CO_2$, from methane, $CH_4$, in process feedstreams comprised of both components.

In accordance with one embodiment of the present invention there is provided a process for separating $CO_2$ from a process feedstream, comprising:
  a) contacting an adsorbent bed comprised of a zeolitic imidazolate framework material with a process feedstream comprising $CO_2$ and $CH_4$ at a first pressure and first temperature;
  b) adsorbing at least a portion of the $CO_2$ in the adsorbent bed;
  c) producing a $CO_2$-lean product stream, wherein the $CO_2$-lean product stream has a lower concentration of $CO_2$ by vol % than the process feedstream; and
  d) producing a $CO_2$-rich product stream at a second pressure and second temperature, wherein the $CO_2$-rich product stream has a higher concentration of $CO_2$ by vol % than the process feedstream;
  wherein the zeolitic imidazolate framework material has a framework structure wherein each vertex of the framework structure is comprised of a single metal ion and each pair of connected adjacent vertices of the framework structure is linked by nitrogen atoms of an imidazolate anion or its derivative, and wherein the zeolitic imidazolate framework material has an adsorptive loading ratio for $CO_2$ over $CH_4$ of at least 10.

In accordance with another embodiment of the present invention there is provided a process for separating $CO_2$ from a process feedstream, comprising:
  a) contacting a first side of a membrane comprised of a zeolitic imidazolate framework material with a process feedstream comprising $CO_2$ and $CH_4$ at a first pressure and first temperature;
  b) retrieving a first permeate stream from a second side of the membrane at a second pressure and second temperature, wherein the first permeate stream consists of components that selectively permeate through the membrane and the first permeate stream has a higher concentration of $CO_2$ by vol % than the process feedstream; and
  c) retrieving a first retentate stream;
  wherein the zeolitic imidazolate framework material has a framework structure wherein each vertex of the framework structure is comprised of a single metal ion and each pair of connected adjacent vertices of the framework structure is linked by nitrogen atoms of an imidazolate anion or its derivative, and wherein the zeolitic imidazolate framework material has an adsorptive loading ratio for $CO_2$ over $CH_4$ of at least 10.

In other preferred embodiments of the present invention, the process feedstream is comprised of a natural gas, a synthetically produced gas, a landfill produced gas or a biogenically produced gas.

In even more preferred embodiments of the present invention, the zeolitic imidazolate framework material is selected from ZIF-7 and ZIF-9.

DETAILED DESCRIPTION OF THE INVENTION

Figure 1:
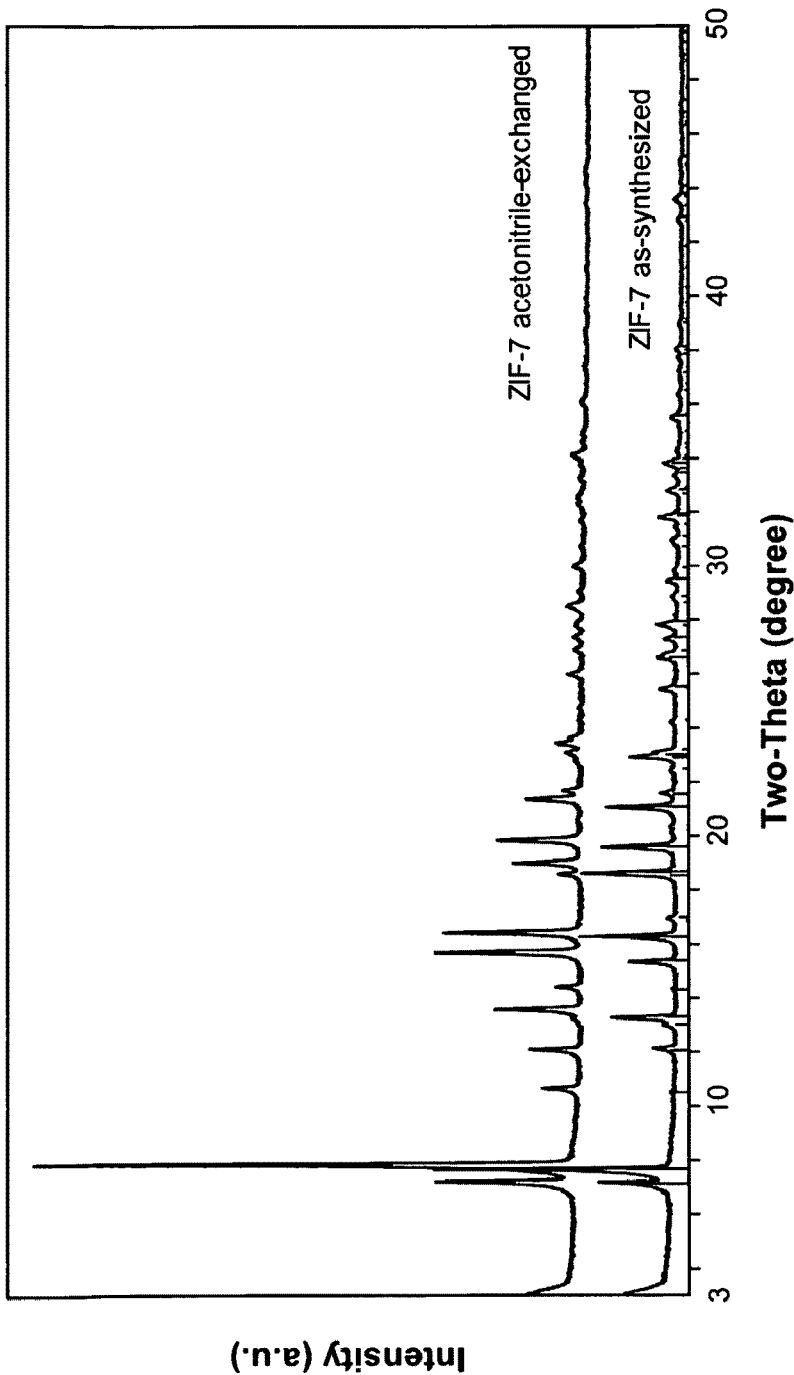
FIG. 1 is the experimental powder X-ray diffraction ("PXRD") patterns of the as-synthesized and acetonitrile-exchanged ZIF-7 samples of Example 1 herein. The calculated PXRD pattern (shown as the vertical stick patterns in the figure) for ZIF-7 based on the single crystal structure of ZIF-7 reported in the "Park Reference" as referenced herein is also shown in the figure.

The present invention is directed to processes for the separation of carbon dioxide ("$CO_2$") from methane ("$CH_4$") in streams containing both carbon dioxide and methane utilizing adsorbents comprised of zeolitic imidazolate framework ("ZIF") materials. Preferably the zeolitic imidazolate frameworks are utilized in a swing adsorption process. The general term "swing adsorption process" as used herein shall be taken to include Pressure Swing Adsorption ("PSA") processes, Temperature Swing Adsorption ("TSA") processes, Pressure Purge Displacement Processes ("PPSA"), Rapid Cycle Pressure Swing Adsorption ("RCPSA") processes, Rapid Cycle Temperature Swing Adsorption ("RCTSA") processes, Rapid Cycle Pressure Purge Displacement Processes ("RCPPSA") as well as combinations of these swing adsorption processes. In a preferred embodiment, the stream to be separated is fed to the process in a substantially gaseous state.

In other preferred embodiments of the present invention, zeolitic imidazolate framework ("ZIF") adsorbent materials are incorporated into a membrane material for the selective separation of carbon dioxide ("$CO_2$") from methane ("$CH_4$") in streams containing both carbon dioxide and methane. The ZIF materials will preferably be utilized in a matrixed membrane material to facilitate the separation of $CO_2$ from $CH_4$. In a preferred embodiment, the feedstream to be separated will contact the membrane wherein the $CO_2$ and the $CH_4$ in the feedstream will be substantially in a gaseous phase.

"Zeolitic imidazolate framework" (or "ZIF") materials are defined herein as microporous crystalline structures having framework topologies commonly found in zeolites and/or in other crystalline materials wherein each vertex of the framework structure is comprised of a single metal ion and each pair of connected adjacent vertices of the framework structure is linked by nitrogen atoms of an imidazolate anion or its derivative. The terms "micropore" or "microporous" as utilized herein is defined as a pore diameter or a material containing pore diameters of less than or equal to 2.0 nm (20 Å), respectively. Descriptions and the synthesis of some of the ZIF materials that can be utilized in the present invention are disclosed in United States Patent Publication No. US 2007/0202038A1 to Yaghi et al., which is hereby incorporated by reference.

The applicants of the present invention have discovered that ZIF materials can selectively separate $CO_2$ from $CH_4$ in streams containing both of these components. Furthermore, this may be accomplished at conditions of pressure, temperature and compositions that are relevant to industrial processes. In order to separate two components from a mixture, the adsorption loading (e.g., in mmole/g) for the first component must be greater than the adsorption loading (e.g., in mmole/g) for the second component. Even though process schemes can be designed to operate at low ratios of adsorption loading (in mmole/g) for the first component vs. the adsorption loading (in mmole/g) for the second component, it is preferred that this "adsorptive loading ratio for $CO_2$ over $CH_4$" for of the ZIF material utilized be at least 10. Since the required equipment size, cost and operating expenses tend to be significantly lowered at higher adsorptive loading ratios, the separations processes become much more attractive utilizing materials and conditions that lead to higher adsorptive loading ratios. In more preferred embodiments of the present invention, the ZIF material utilized in the present invention has an adsorptive loading ratio for $CO_2$ over $CH_4$ of at least about 15, even more preferably at least about 20, and most preferably, at least about 25.

The ratio described above is a property for a specific adsorbate-adsorbent pair, at given conditions of pressure and temperature. This ratio is referred to herein as the "adsorptive loading ratio" or more particularly as the "adsorptive loading ratio for $CO_2$ over $CH_4$". This ratio is defined herein as a unitless quantity that is equal to the adsorption loading (in mmole/g) for the first component divided by the adsorption loading (in mmole/g) for the second component for a specific adsorbent material at a specific pressure and temperature. As used herein, the term "first component" is synonymous with the component carbon dioxide, $CO_2$, and the term "second component" is synonymous with the component methane, $CH_4$. As used herein, although it is preferred that the adsorption loading for each component on a particular ZIF material be measured under the operating component partial pressure and temperature conditions for the system, it is often more advantageous to measure the adsorption loading for a particular ZIF for each component material at more "standard" conditions of pressure and temperature. Therefore, for the purposes of this invention and the scope of the present invention, the adsorptive loading ratio for two components (e.g., $CO_2$ and $CH_4$) can be measured at either operating partial pressure for the specific components and operating temperature conditions for the feedstream contacting the ZIF-containing adsorbent, or at single component testing conditions chosen herein to be 301 K (28° C.) and 106.6 kPa (800 torr). Unless stated otherwise, these latter conditions were used in the testing of the samples in the examples herein, which can be readily duplicated in a laboratory test facility.

ZIF materials that exhibit significantly large adsorptive loading ratios may be used in swing adsorption processes of the present invention to effectively and economically separate $CO_2$ from $CH_4$ in streams containing both components. Each of these swing adsorption processes are comprised of a number of "steps" that include a variety of adsorption and desorption steps that in combination lead to a complete swing adsorption "cycle" that is periodically repeated. Since multiple adsorbent beds are typically used, their appropriate time synchronization leads to the continuous production of products. A complete swing adsorption cycle on a particular adsorbent bed, therefore, comprises all of the adsorption and desorption steps that are taken, beginning with the very first contacting of the feed gas mixture with the adsorbate-free or substantially adsorbate-free adsorbent and continuing through the last desorption stage that regenerates the adsorbent into its adsorbate-free or substantially adsorbate-free state and further including any additional repressurizing and/or purging steps that may occur thereafter to bring the "cycle" back to the first contacting of the feed gas mixture with the adsorbate-free or substantially adsorbate-free adsorbent which has begun the "cycle". At this point, the next swing adsorption "cycle" is started and the cycle is subsequently repeated.

Typically, there is at least one adsorption step wherein a process feedstream is contacted with the adsorbent material in a swing adsorption process. The equivalent terms "process feedstream" or "inlet stream" as used herein in swing adsorption embodiments of the present invention is the mixed component stream comprising at least two components to be separated which is contacted with the adsorbent material during the adsorption cycle. During this step of the process, the process feedstream contacts the adsorbent material under certain process temperature and pressure conditions and as the process feedstream flows through the adsorbent material at least a portion of the "first component" (or "strongly adsorbed component") of the process feedstream is preferentially adsorbed by the adsorbent material with respect to a "second component" (or "weakly adsorbed component"). During this step an "effluent stream" (or "$CO_2$-lean product stream" herein) is drawn from the swing adsorption process wherein the total number of moles of the first component into the swing adsorption process is higher than the total number of moles of the first component out of the swing adsorption process during this adsorption step. Although it is not necessary, it is preferred that the molar concentration of the first component in the process feedstream be greater than the molar concentration of the first component in the effluent stream.

The swing adsorption process is also comprised of at least one desorption step wherein at least a portion of the first component that has been preferentially adsorbed by the adsorbent material is recovered in what is termed herein as a "desorbed stream" (or "$CO_2$-rich product stream" herein). During this step, the process conditions in the swing adsorption process are changed to allow at least a portion of the first component to be desorbed from the adsorbent material and collected as a "desorbed stream". This desorption can be induced by a pressure swing, a temperature swing, the introduction of a partial pressure purge displacement stream, or a combination thereof. In a preferred embodiment, the molar concentration of the first component in the desorbed stream is greater than the molar concentration of the first component in the process feedstream. In another preferred embodiment, the molar concentration of the first component in the desorbed stream is greater than the molar concentration of the first component in the effluent stream.

Although at least these two steps (i.e., adsorption and desorption) are required in the swing adsorption processes of the current invention, additional steps may be utilized in the swing adsorption processes. These steps include, but are not limited to, concurrent purge steps, counter-current purge steps, and/or multiple partial pressurization or depressurization steps. These additional steps may be utilized to improve first and/or second component recovery, improve first or second component purity, and/or obtain multiple product streams in addition to the effluent stream and desorbed stream described above.

One embodiment of the swing adsorption process of the present invention utilizes a Pressure Swing Adsorption ("PSA") process wherein the adsorbent material is comprised of a ZIF material and the "first component" as described above is $CO_2$ and the "second component" as described above is $CH_4$. In this PSA process, the partial pressure of the first component in the adsorption step is higher than the partial pressure of the first component in the desorption step which allows at least a portion of the adsorbed first component to be recovered in the desorption step and the adsorbent material to be regenerated by depletion of the adsorbed components for reuse in a subsequent adsorption step. This is accomplished in part by exposing the adsorbent material to lower partial pressure conditions in the desorption step than the partial pressure conditions in the adsorption step. This desorption can be further assisted by utilizing a purge gas to lower the partial pressure of the first component during the desorption step, a purge step, a partial pressurization step, or a partial depressurization step as described above.

Another type of swing adsorption process of the present invention is a Temperature Swing Adsorption ("TSA") process wherein the adsorbent material is comprised of a ZIF material and the "first component" as described above is $CO_2$ and the "second component" as described above is $CH_4$. The TSA processes operate similar to the PSA processes above wherein the partial pressure of the first component in the adsorption step is higher than the partial pressure of the first component in the desorption step which allows at least a portion of the adsorbed first component to be recovered in the desorption step and the adsorbent material to be regenerated by depletion of the adsorbed components for reuse in a subsequent adsorption step. However, in the TSA processes, this is accomplished in part by exposing the adsorbent material to higher temperature conditions in the desorption step than the temperature conditions in the adsorption step. This desorption can be further assisted by utilizing a purge gas to lower the partial pressure of the first component and/or provide heating of the adsorbent material during the desorption step, a purge step, a partial pressurization step, or a partial depressurization step as described above.

It should also be noted that the steps of the PSA and TSA processes can be combined in a PSA/TSA process of the present invention. In these combined processes, both pressure and temperature changes or "swings" are made between the adsorption steps and desorption steps of the process, resulting in a desired separation of at least a portion of the first component from the second component of the mixed component process feedstream fed to the inlet of the PSA/TSA process.

In embodiments of the swing adsorption processes of the present invention, the ZIF materials may be incorporated into the adsorption swing process in many structural forms and/or in combination with additional components. The ZIF materials may be incorporated as crystallites of preferred size and shape of substantially uniform dimensions or with dimensions suitably distributed according to a preferred distribution. The crystallites may be used directly as produced in the synthesis steps or be more preferably formulated into larger aggregates or incorporated into a structured or matrix material to provide form, stability, and/or in combination with other complementary co-adsorbent materials that can fulfill a variety of other beneficial functions to the overall process. Non-limiting examples include incorporating the ZIF material with a binder material to form a matrix comprising a binder material selected from a crystalline polymer, a non-crystalline polymer, an epoxy, a thermoplastic, a clay, a silica-containing material, an alumina-containing material, and a titania-containing material. The binder material may also exhibit either a microporous or a mesoporous structure. Additionally, it may be advantageous to add suitably chosen additives into this binder material. These additives can be used to improve the adsorption/desorption and transport properties of the selected components within the ZIF materials. Non-limiting examples of these additional additives include zeolites and microporous crystalline materials such as pure silicates, silicoaluminophosphates ("SAPO"s), aluminophosphates ("AlPO"s). In a preferred embodiment, the additional additive is a zeolite. Other additives such as metals or other high heat capacity and high heat conductivity materials may also be incorporated into the matrix to assist in the capture and transfer of at least a portion of the heat that is generated during the exothermic adsorption step(s) of the swing adsorption process, thereby shortening the duration of the cycling process, increasing throughput, and further improving the overall efficiency of the ZIF material for adsorbing the select component or components.

When the ZIF materials are incorporated with a binder, the adsorbent material can be formulated into optimal geometric shapes or be applied onto supporting substrates which further improve the durability of the adsorbent and the rate at which the selected adsorbing components are brought into contact with the adsorption sites of the ZIF material. Non-limiting examples include beads, extrudates, formed pellets, structured beds, monoliths and hollow fibers, as well as coatings applied to plates or monolithic structures fibers or hollow fibers. Depending upon the specific situation, inlet stream composition as well as product stream compositions, process conditions and equipment design for the process of the present invention, certain structures and/or matrix compositions can provide improved separation efficiencies and/or selectivities for the overall process.

Any of the steps described above (i.e., structuring, additives, co-adsorbents, etc) that allow a reduction in the duration of a complete swing adsorption cycle or simply "cycle" are of utmost practical importance since shorter cycle times result in higher throughputs and/or can reduce equipment cost. Whereas conventional swing adsorption processes typically operate at cycles with durations of the order of minutes, with the materials of the present invention and the abovementioned process modifications, it is possible to significantly reduce the duration of a complete cycle by more than 50%. These rapid cycle swing adsorption processes that are enabled by the materials and process conditions of the present invention are particularly advantageous from an economic standpoint. In preferred embodiments of the present invention, the ZIF material is utilized in a swing adsorption process wherein the cycle time is less than about 1 minute, and more preferably, the ZIF material is utilized in a swing adsorption process wherein the cycle time is less than about 30 seconds. In an even more preferred embodiment of the present invention, these short cycle times are incorporated into a rapid cycle pressure swing adsorption ("RCPSA") process embodiment of the present invention.

In another embodiment of the present invention, the ZIF material can be incorporated into a membrane process for the selective separation of carbon dioxide, $CO_2$, from methane, $CH_4$, in streams comprising a mixture of these components. In this embodiment, a ZIF material is incorporated within or coated onto an inorganic substrate or a polymer material and utilized in a membrane separation process, thereby producing a "ZIF-containing membrane". The ZIF material of the membrane, has a net permeation affinity for $CO_2$ over $CH_4$. The permeation rate can be typically described in terms of two multiplicative factors, one related to the diffusion rate and another related to the adsorption loadings of the components of the mixture on the ZIF material. With respect to this latter factor, a ZIF material incorporated into the membrane which has a higher adsorptive loading ratio for $CO_2$ over $CH_4$, improves the concentration gradient for $CO_2$ either at the membrane surface (if coated onto the membrane surface) and/or in the membrane (if incorporated into the membrane matrix). This improved concentration gradient enhances the selective permeation of $CO_2$ relative to $CH_4$ through the membrane, resulting in an improved recovery of $CO_2$ in the membrane permeate stream.

In this embodiment of the present invention, a process feedstream comprising $CO_2$ and $CH_4$ contacts a first side of a ZIF-containing membrane and at least a portion of the process feedstream permeates through the membrane and is retrieved from a second side of the membrane material as a permeate stream. The permeate stream is obtained from the second side of the membrane and the permeate stream thus obtained has a higher vol % of $CO_2$ than the process feedstream. The equivalent terms "process feedstream" or "inlet stream" as used herein in membrane process embodiments of the present invention is the mixed component stream comprising at least two components to be separated which is contacted with the first side of the ZIF-containing membrane. It should be noted that in some embodiments, a "sweep stream" may be utilized on the permeate side of the ZIF-containing membrane in the membrane separation process of the present invention. It should also be noted that the term "permeate stream" as used herein and its composition properties are measured based solely upon the composition of the stream that permeates through the ZIF-containing membrane. For purposes of this invention, if any additional stream, such as a sweep stream, is added on the permeate side of the membrane process, the composition of this sweep stream must be excluded from the compositional analysis of the permeate stream.

Continuing with this process embodiment of the present invention, at least one retentate stream is also obtained from the first side of the membrane which has a lower vol % of $CO_2$ than the process feedstream that initially contacts the membrane. In this manner, a separation of components is made resulting in a higher value for the two separated streams (i.e., the retentate and the permeate streams) than the original mixed stream that is fed to the membrane separations process. In preferred embodiments, the ZIF material utilized in the membrane process of the present invention has an adsorptive loading ratio for $CO_2$ over $CH_4$ of at least about 10, more preferably at least about 20, and even more preferably, at least about 25.

The membranes utilized in embodiments of the present invention can be asymmetric and can be comprised of several layers of different materials. To improve the mass transfer characteristics of these asymmetric membrane structures one or more of these layers can be a porous material. A thin selective layer imparts most of the molecular selectivity in the asymmetric membrane structure and in a preferred embodiment this selective layer contains the ZIF material. On the feed side molecules are selectively adsorbed in the selective layer and on the permeate side the molecules are desorbed. The selective ZIF-containing layer can optionally include other materials. One of the materials that can be present in the ZIF-containing layer is a polymer. When the ZIF containing layer contains more than 10 vol % of another material the selective layer is called a mixed matrix. To mitigate the effect of any defects or pinholes in the selective layer, a reparation coating or reparation layer can be incorporated in the membrane structure.

The ZIF-containing membrane will typically be part of a membrane module that includes a pressure housing. Non-limiting examples of ZIF-containing membrane structures that can be incorporated into the membrane module are hollow-fiber membrane structures, flat sheet membrane structures, and monolithic membrane structures. The membrane module will typically contain seals to isolate the retentate and permeate zones of the module and to prevent flow bypass or cross-contamination of the retentate stream(s) to the permeate stream(s). The seals may also serve as a device for holding the membrane in place within the membrane module.

There are many applications in the industry which can benefit from a process that allows such efficient separation of these two components in a gas phase stream. Most conventional processes for the separation of $CO_2$ from $CH_4$ rely on cryogenic liquefaction of at least one component, typically $CO_2$, and subsequent distillation or crystallization for the efficient separation of these components when present in gas phase streams. The cost of liquefying these gases to temperatures of below about −40° C. (233 K) in order to separate these components makes cryogenic separation processes very costly and results in the separation and recovery of the components from many available mixed gas streams economically unfeasible.

Figure 13:
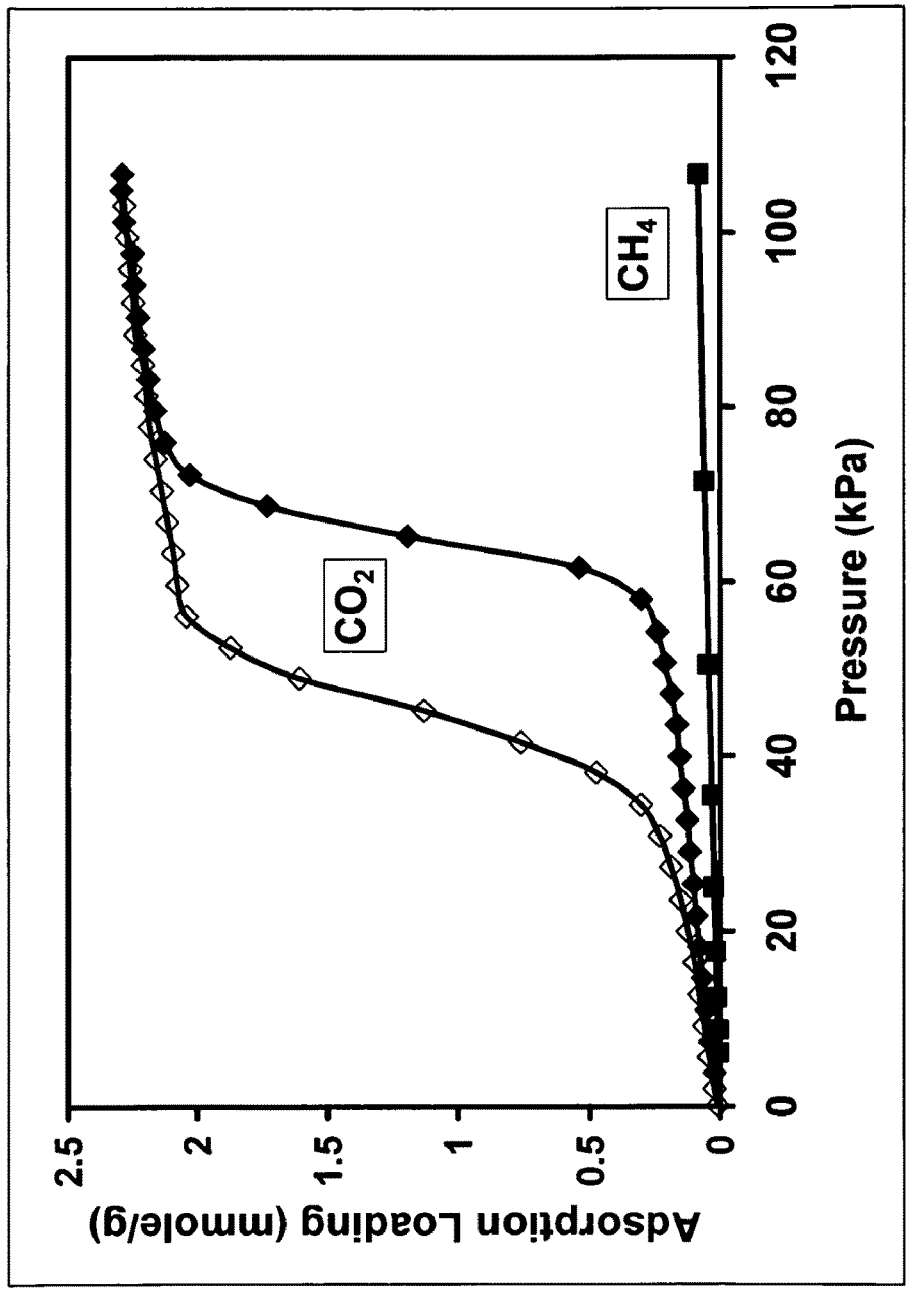
FIG. 13 shows the $CO_2$ adsorption isotherm and the $CH_4$ adsorption isotherm at 301 K for a ZIF-7 sample of Example 6.
Figure 14:
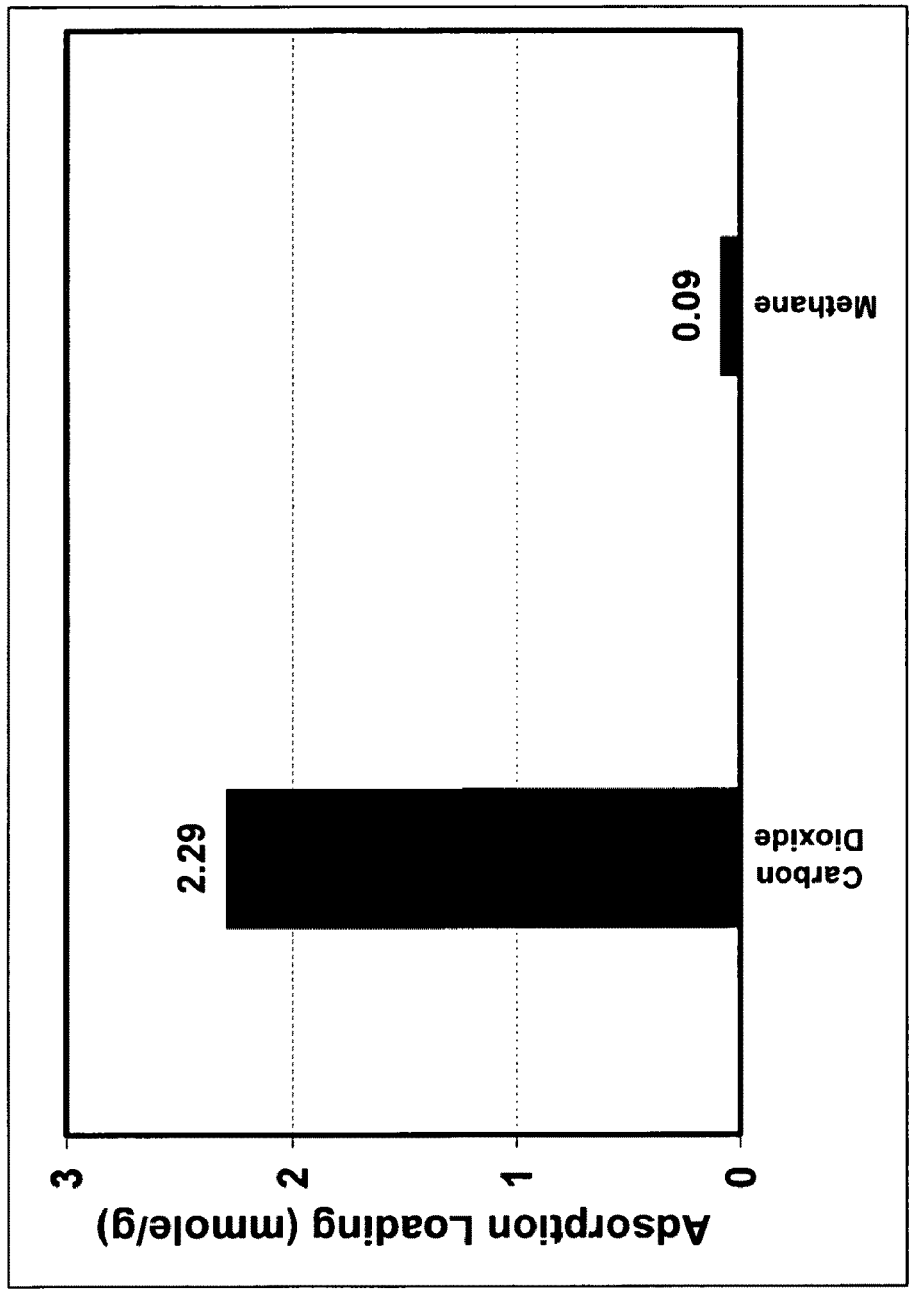
FIG. 14 is a bar graph comparing the adsorption loadings of a ZIF-7 sample of Example 5 for $CO_2$ and $CH_4$ at 301 K and 106.6 kPa.

As an example, FIG. 13 shows the adsorption isotherms for ZIF-7 for carbon dioxide, $CO_2$, and for methane, $CH_4$. As can be seen in this figure, ZIF-7 (as well as ZIF-9 in FIG. 18) has a large adsorptive loading ratio for $CO_2$ over $CH_4$. The overall adsorption loading of these components at standard test conditions of 301 K and 106.6 kPa is shown in the bar graph of FIG. 14. As can be seen in FIG. 14, under these standard test conditions, ZIF-7 has an adsorption loading for $CO_2$ of about 2.29 mmole/g while the ZIF-7 has an adsorption loading for $CH_4$ of only about 0.09 mmole/g. The adsorptive loading ratio for $CO_2$ over $CH_4$ is greater than about 25. Such high adsorptive loading ratios render these ZIF materials very effective adsorbent materials of the processes of the present invention.

It is also noted that ZIF-7 (as well as ZIF-9) exhibits a unique isotherm shape not typically found in microporous crystalline materials such as zeolites. As described herein, this unique isotherm shape for $CO_2$ in ZIF-7 has important implications and distinctively enables embodiments of the present invention. FIG. 13 shows that the isotherm for $CO_2$ at 301 K displays a hysteretic behavior characterized by unique adsorption (solid diamonds) and desorption (open diamonds) branches. The transition from low to high loading in the adsorption branch at about 60 kPa signals a more favorable accommodation of the $CO_2$ within the ZIF-7 structure than in the Henry's law-like region below about 60 kPa. Similarly, the transition from high to low loading in the desorption branch at about 50 kPa signals the less favorable accommodation of the $CO_2$ within the ZIF-7 structure. This behavior is the result of unique energetic interactions between the adsorbed $CO_2$ and the ZIF-7 structure that, as described herein, advantageously enables embodiments of the pressure swing adsorption processes of the present invention. With this particular isotherm shape, it is possible to develop an effective pressure swing adsorption cycle that requires a narrow pressure swing that is only of the order of the pressure gap that exists between the rising adsorption branch and the decreasing desorption branch (i.e., a pressure swing of approximately 20 to 30 kPa in this example). It is also worth noticing that such a cycle would be associated with a fairly large "working capacity" (and thus aid the economics of the process), as seen from the large difference between the loadings at the low and high pressures at which the cycle would operate. The "working capacity" of an adsorbate material is defined herein as the difference between the adsorbate loading in the adsorption step and the adsorbate loading in the desorption step of the "strongly adsorbed component" (which herein is $CO_2$). Larger values of the working capacity are desirable. With more standard adsorbent materials that do not exhibit the type of hysteresis behavior shown in FIG. 13 (i.e., exhibit a more conventional gradual increase in loading with pressure at a constant temperature), the pressure swing has to be significantly broader to achieve an equivalent level of working capacity, with concomitant implications for a higher cost operation.

From the previous discussion on the uniqueness of the isotherm shape, particularly the transition from low to high loading, it follows that in preferred embodiments of the present invention, the ZIF material is utilized in a swing adsorption process, wherein the applied pressure swing is less than about 300 kPa. In preferred embodiments of the present invention, the ZIF material is utilized in a swing adsorption process wherein the applied pressure swing is less than about 200 kPa; and even more preferably, the ZIF material is utilized in a swing adsorption process wherein the applied pressure swing is less than about 100 kPa. In an even more preferred embodiment of the present invention, these narrow applied pressure swings are incorporated into a pressure swing adsorption ("PSA") process embodiment of the present invention. The term "applied pressure swing" as utilized herein is defined as the difference in the maximum and minimum $CO_2$ partial pressures that are experienced in the adsorbent bed during a swing adsorption cycle.

Figure 12:
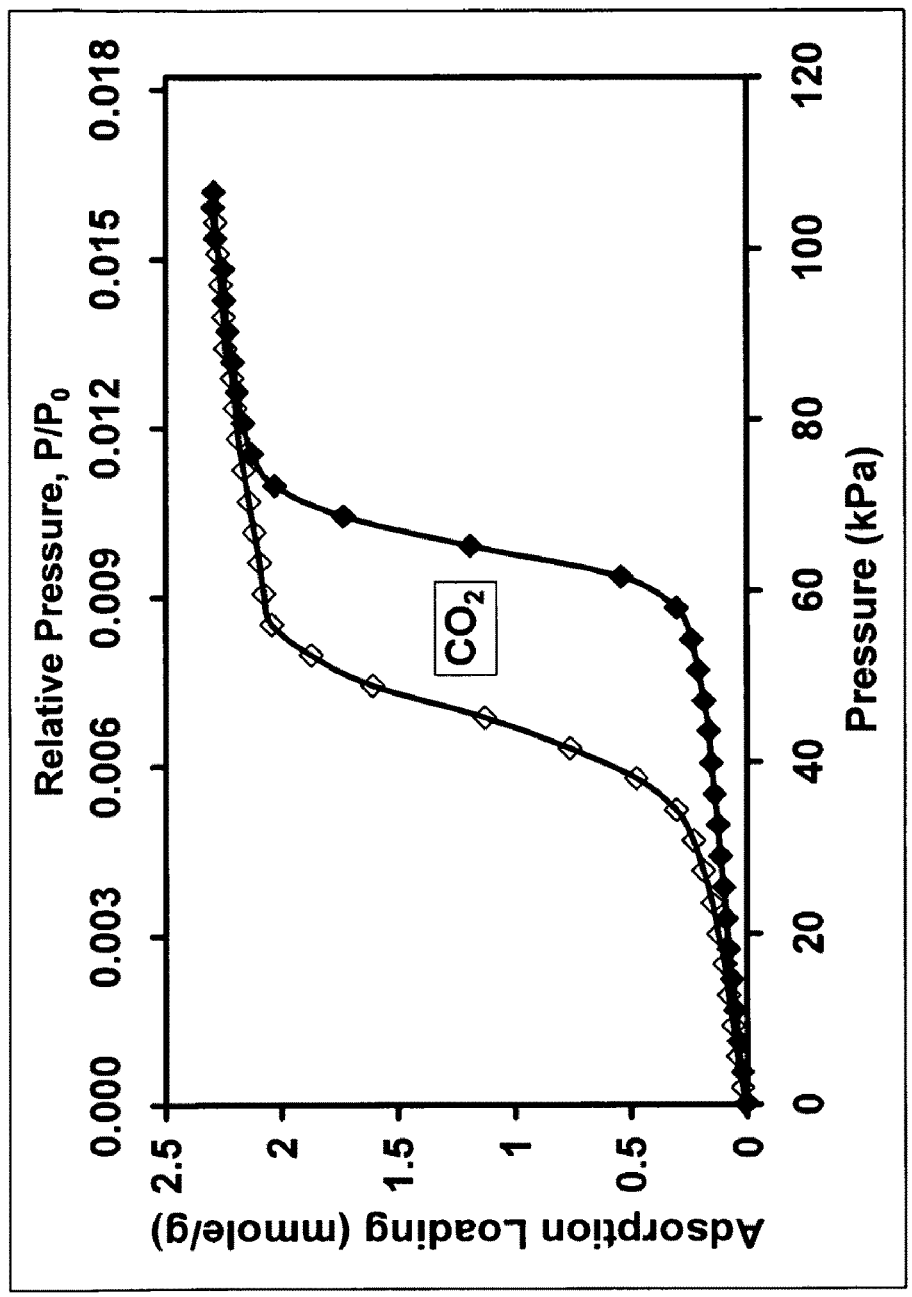
FIG. 12 shows the $CO_2$ adsorption isotherm at 301 K for a ZIF-7 sample of Example 6.

The adsorption isotherm features displayed in FIG. 13 for ZIF-7 have several other advantageous implications for the swing adsorption processes of the present invention. As also shown in FIG. 12, the absolute $CO_2$ partial pressure region at which the low to high adsorption loading transition takes place is fairly low. When such partial pressure (P) is expressed relative to the saturation pressure of $CO_2$ at the temperature of the test experiment ($P_0$), the transition takes place at a relative $P/P_0$ value of less than 0.01 at 301 K (see upper abscissa in FIG. 12), Such low values of $P/P_0$ make ZIF-7 very attractive for adsorbing $CO_2$ from streams that contain low levels of $CO_2$ that would be difficult to adsorb with more conventional materials that require a higher partial pressure to achieve an acceptable adsorption loading at the same temperature. Even more important from a $CO_2/CH_4$ separations standpoint, it is noticed that at the same conditions of pressure and temperature than for $CO_2$, the weaker interactions of $CH_4$ with the ZIF-7 structure do not cause the transition to a high loading state. FIG. 14 shows that when $CH_4$ is contacted with the ZIF-7 material at pressures as high as 106.6 kPa and 301 K, the adsorption loading remains low, in a Henry's law kind of regime, ultimately giving rise to a high adsorptive loading ratio for $CO_2$ relative to $CH_4$ at those conditions. While it is expected that higher $CH_4$ partial pressures could eventually cause the transition to a higher loading state to take place in a material like ZIF-7 at the same temperature of 301 K, one of skill in the art of pressure swing adsorption processes knows that adsorption phenomena are temperature-activated and that the temperature can also be proportionally raised to prevent such transition to occur and thus prevent significant amounts of $CH_4$ from loading into the adsorbent material, which is a key objective of the separation process where it is desired to maximize the enrichment of the adsorbent material with the preferred adsorbate component, $CO_2$. It should also be noted that similar characteristics are exhibited by the ZIF-9 material shown in Example 7.

From the previous discussion on the features of the adsorption isotherm, particularly in embodiments desiring the attainment of high loadings of the preferred adsorbate at low pressures, in a preferred embodiment of the present invention, the ZIF material is utilized in a swing adsorption process wherein the $CO_2$ partial pressure in the gas mixture to be separated is less than about 200 kPa, and more preferably, the ZIF material is utilized in a swing adsorption process wherein the $CO_2$ partial pressure in the gas mixture to be separated is less than about 100 kPa. In an even more preferred embodiment of the present invention, the processing of these low $CO_2$ partial pressure streams are incorporated into a pressure swing adsorption ("PSA") process embodiment of the present invention.

Figure 15:
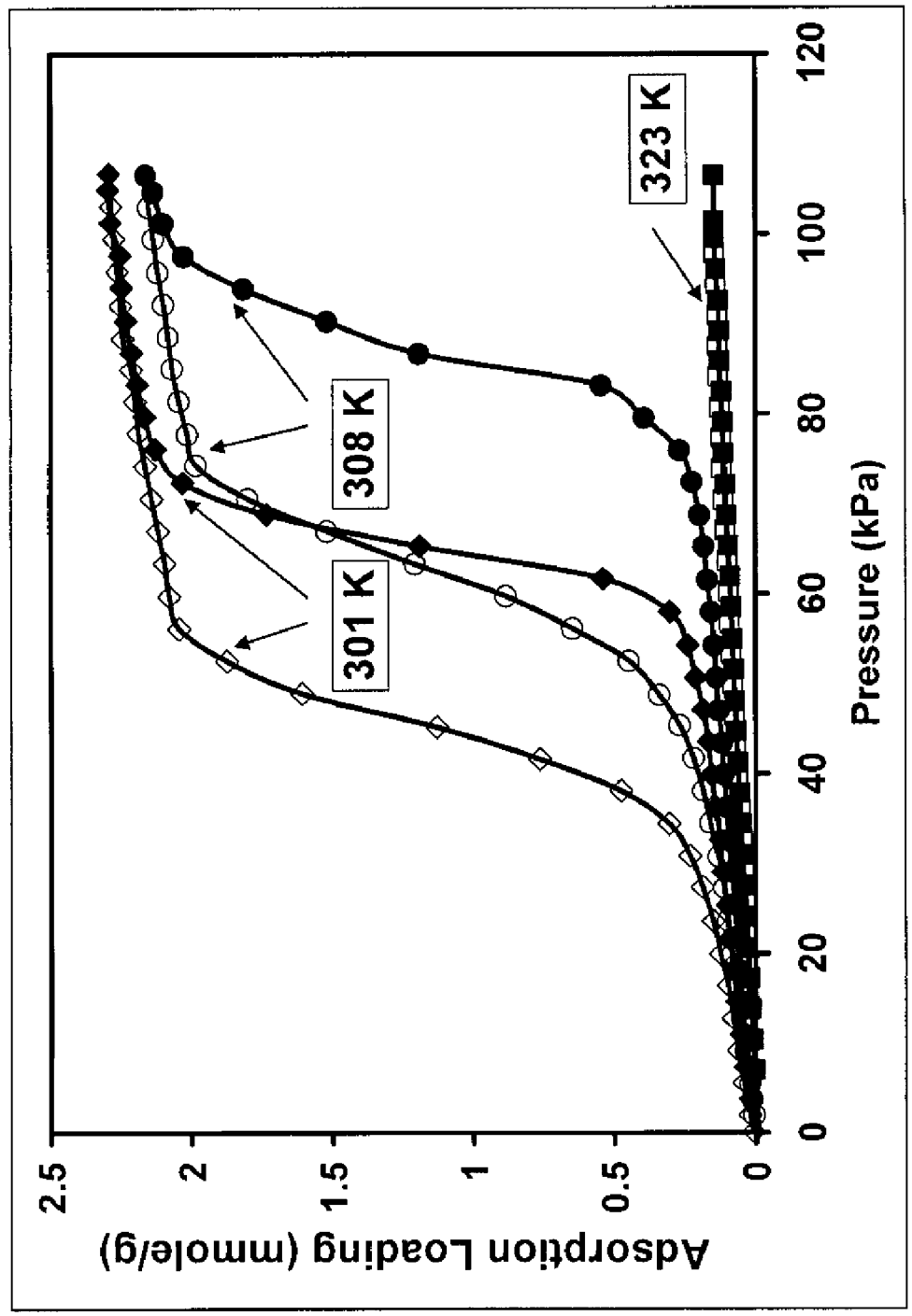
FIG. 15 shows the $CO_2$ adsorption isotherms at 301 K, 308 K, and 323 K for a ZIF-7 sample of Example 6.

The use of temperature to prevent the low to high loading transition in the isotherm is illustrated for $CO_2$ in FIG. 15. This figure contrasts the adsorption isotherms for $CO_2$ in ZIF-7 at three temperatures, namely 301 K, 308 K and 323 K. As the temperature is increased from 301 K to 308 K, both the adsorption and desorption branches remain but are displaced to higher $CO_2$ pressures. When the temperature is further increased to 323 K, the transition does not take place even at pressures of 106.6 kPa, thus confirming the temperature-activated nature of the adsorption process on solid adsorbents such as the ZIFs materials of the present invention. Just as the temperature can be increased to displace or prevent the low to high adsorption loading transition for an adsorbate in a given pressure range (as shown above), the temperature can be alternatively decreased to cause such a low to high adsorption loading transition to take place for an adsorbate in a given pressure range or to displace such transition from a higher pressure to a lower pressure. Such interplay of pressure and temperature can be used to design advantageous swing adsorption schemes incorporating the present invention over a wide range of components pressures in the gaseous process feedstreams.

In a particular embodiment of the present invention, the temperature of the process feedstream is reduced prior to contacting the ZIF-containing adsorbent material. This embodiment is particularly beneficial when it is desired to separate $CO_2$ from $CH_4$ in low pressure process feedstreams, especially when the temperatures of the process feedstream may be significant enough to appreciably shift the adsorption and desorption branches to higher $CO_2$ pressures than those experienced at lower temperatures. As can be seen from FIG. 13 herein, ZIF-7, for example, can achieve a significant separation of $CO_2$ from $CH_4$ at near ambient temperatures of about 28° C. (301 K) under low $CO_2$ partial pressures conditions of less than about 80 kPa. However, as can be seen from FIG. 15, these adsorption/desorption branches shift to higher required $CO_2$ partial pressures at elevated temperatures. Conversely, by reducing the temperature of the process feedstream prior to contacting the ZIF-containing adsorbent material, significant separation of $CO_2$ from $CH_4$ can be achieved at very low pressures due to the corresponding shift of the adsorption and desorption branches to lower pressures.

Figure 17:
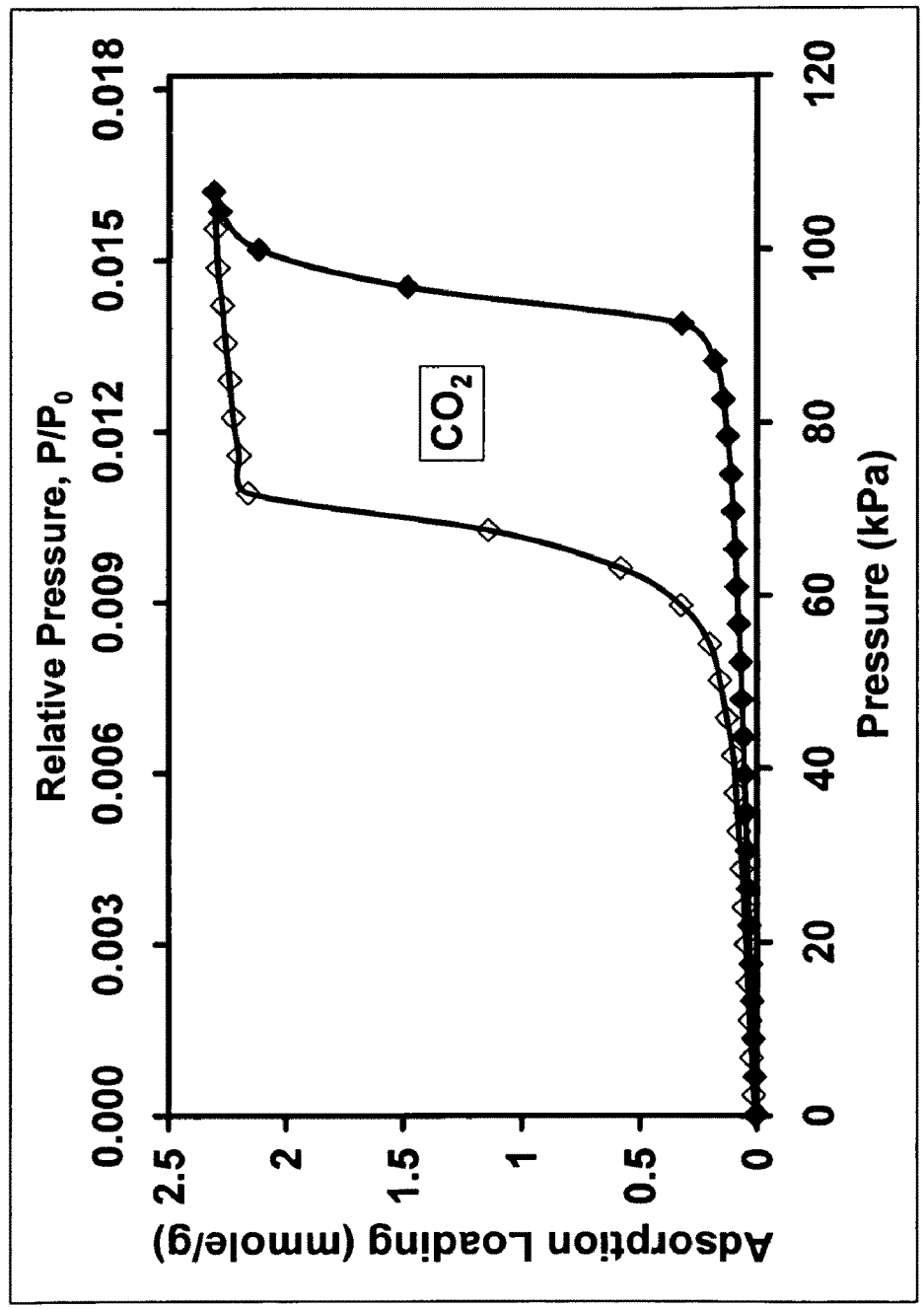
FIG. 17 shows the $CO_2$ adsorption isotherm at 301 K for a ZIF-9 sample of Example 7.
Figure 18:
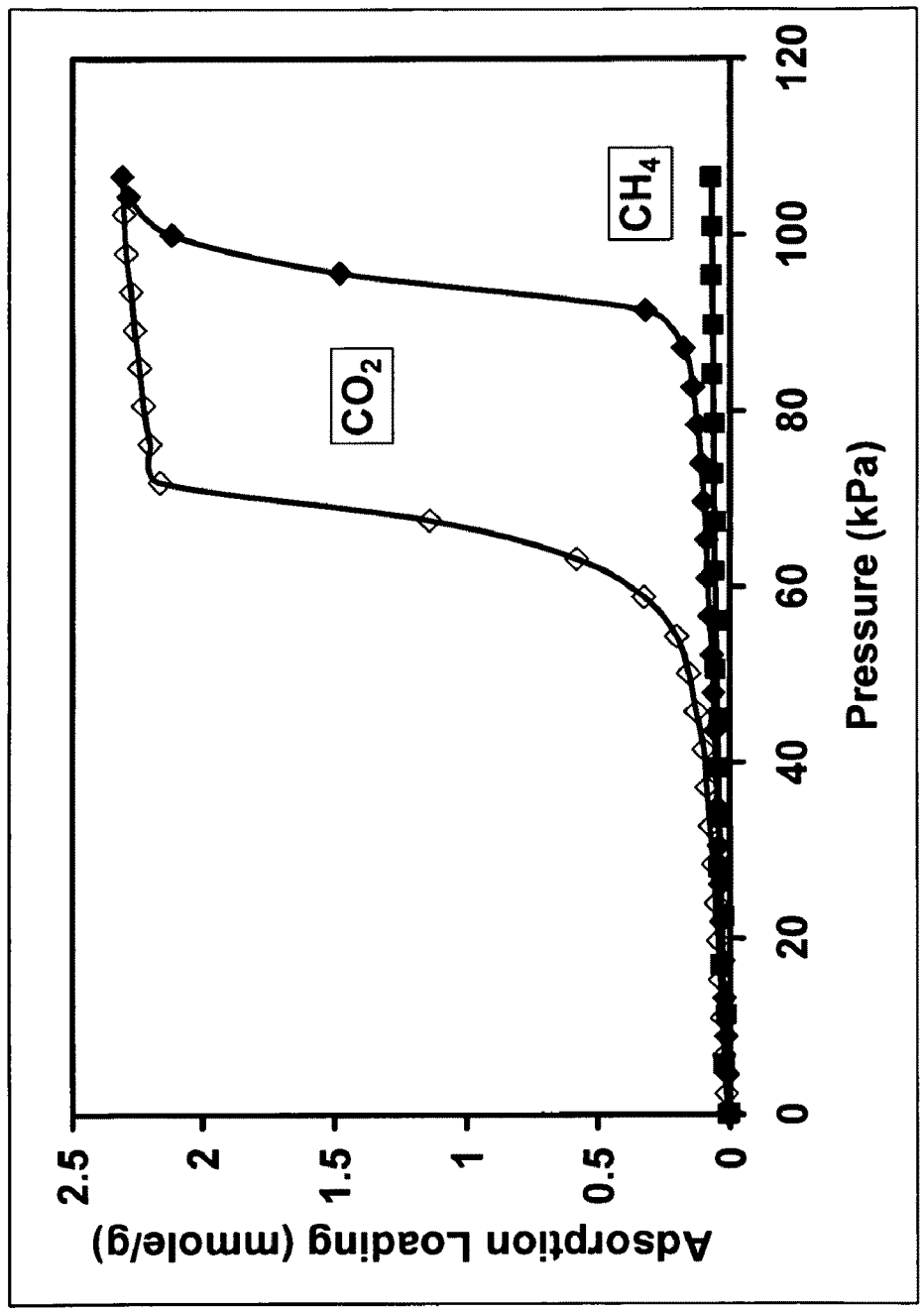
FIG. 18 shows the $CO_2$ adsorption isotherm and the $CH_4$ adsorption isotherm at 301 K for a ZIF-9 sample of Example 7.
Figure 19:
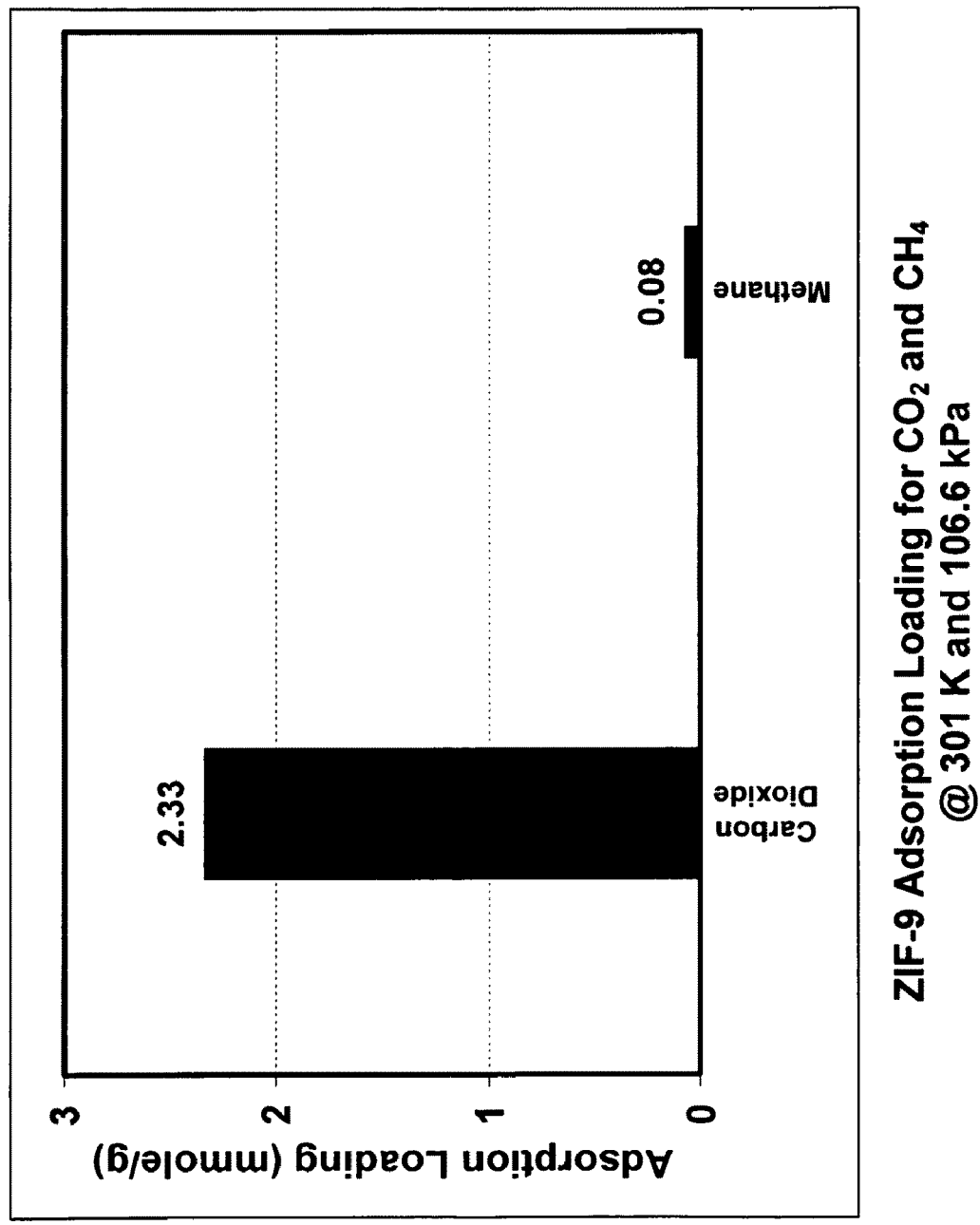
FIG. 19 is a bar graph comparing the adsorption loadings of a ZIF-9 sample of Example 7 for $CO_2$ and $CH_4$ at 301 K and 106.6 kPa.

The characteristics, and swing process implications, of the unique adsorption isotherms shown for ZIF-7 in FIGS. 12 and 13 are also applicable to other ZIF materials having different compositions of matter, which exhibit similar energetic interactions with components such as $CO_2$ and $CH_4$. Thus, while ZIF-7 contains Zn as the single metal ion, ZIF-9 of Example 2, which contains Co as the single metal ion, also exhibits the advantages described herein for ZIF-7 in pressure swing adsorption processes. As described in Examples 1 and 2, both ZIF-7 and ZIF-9 have the same crystal framework structure, SOD. FIGS. 17 and 18 show the corresponding adsorption characterization data for ZIF-9. FIGS. 17 and 18 show that the transition from low to high adsorption loading occurs at a slightly higher $CO_2$ pressure in ZIF-9 (i.e., about 90 kPa) than in ZIF-7 (i.e., about 60 kPa) at the same temperature of 301 K. This difference between ZIF-9 and ZIF-7 primarily reflects some small differences in energetics between the corresponding adsorbate-adsorbent pairs but the overall adsorption characteristics are substantially the same. Interestingly, as shown in FIG. 19, the adsorptive loading ratio for ZIF-9 at 301 K and 106.6 kPa is equal to 29 (=2.33/0.08), while the corresponding adsorptive loading ratio for ZIF-7 is equal to 25 (=2.29/0.09) (see FIG. 14). Thus, these results further illustrate the advantages and breadth of applications of the ZIFs materials of the present invention for separating gaseous mixtures containing $CO_2$ and $CH_4$ through swing adsorption processes.

A major need in the current industry is for effective gas phase processes for the separation of carbon dioxide from methane in the recovery and production of natural gas from gas fields. While methane is a valuable hydrocarbon component for natural gas, almost all natural gas fields contain some level of carbon dioxide in the gas stream. Although the composition of the streams will vary from field to field, many of these natural gas field streams contain a large amount of carbon dioxide, typically in concentrations greater than about 5 vol %. In some instances these natural gas field streams can have a carbon dioxide content greater than about 25 vol %, and in some instances the carbon dioxide content can be even greater than about 50 vol %. In these latter instances, even when the fields have large amounts of stranded gas, processing of the field streams can be economically prohibitive due to the significant equipment and operating expenses associated with the removal of these high levels of carbon dioxide from the valuable methane contained in these gas mixtures. Unless otherwise noted, all component concentrations expressed herein are on a water-free basis.

In the processing of natural gas, it is important to remove $CO_2$ from the processed natural gas. Since the $CO_2$ is non-flammable, the $CO_2$ content of the final natural gas product must be reduced to sufficiently low levels to meet the minimum BTU requirements for natural gas shipped by pipeline. In most cases, the $CO_2$ content of the pipelines natural gas stream needs to be less than about 5 vol %, preferably less than about 2 vol %. Although higher $CO_2$ contents can be utilized as an intermediate product stream from the processes of the present invention, in preferred embodiments of the present invention, the effluent stream obtained from the swing adsorption processes has a $CO_2$ content of less than about 5 vol %, and more preferably less than about 2 vol %.

Another problem that exists in separating $CO_2$ from $CH_4$ in natural gas streams is that the natural gas streams are usually obtained from gas fields under very high pressure. Typical natural gas recovery pressures usually range from about 500 psig (3,447 kPa) to up to about 5,000 psig (34,474 kPa). Since most PSA and TSA processes can be designed to produce a better separation at lower operating pressures (typically below about 500 psig (3,447 kPa) for the inlet stream in the adsorption step in the process), it is desirable to have adsorbent materials with high adsorptive loading ratios that can perform separations efficiently at higher pressures than conventionally performed. Although the swing adsorption processes of the present invention can run efficiently at inlet stream pressures of less than 250 psig (1,724 kPa), in other embodiments, PSA and TSA processes of the present invention can be operated at inlet stream pressures in excess of about 500 psig (3,447 kPa), or even about 1000 psig (6,895 kPa). Although an effluent stream pressure of less than about 250 psig (1,724 kPa) will normally be desired to maintain a good selectivity of the separation made, effluent stream pressures of greater than about 250 psig (1,724 kPa), or even greater than about 500 psig (3,447 kPa) may be obtained especially when utilizing a ZIF material with adsorptive loading ratios for $CO_2$ over $CH_4$ of greater than about 10. Maintaining the effluent stream at these higher pressures is economically desired to minimize the repressurization equipment and energy required to ship the purified natural gas via pipeline. Pipeline pressures for transport of the purified natural gas product stream are typically in the range of about 800 (5,516 kPa) to about 2000 psig (13,790 kPa).

The processes of the present invention can utilize the ZIF adsorption materials at these higher pressures by designing the swing adsorption processes to operate at higher temperatures to capture the benefits between the adsorption and desorption of $CO_2$ in the ZIF material relative to $CH_4$. As described earlier, high adsorptive loading ratios can be maintained at increasing $CH_4$ partial pressures by operating the processes at higher temperatures that ensure the $CO_2$ transition from a low to a high adsorption loading state while simultaneously preventing such transition for $CH_4$. Due to the temperature-activated nature of the adsorption processes (see FIG. 15), which is an intrinsic feature to any adsorbate-adsorbent pair, increasing temperature displaces the transition for both $CO_2$ and $CH_4$ to higher pressures while keeping substantially the same adsorptive loading ratio for $CO_2$ over $CH_4$.

In addition to transportation of natural gas via gas pipelines, there is a quickly growing market for the transportation of liquefied natural gas, or "LNG". In transportation of LNG products, the requirements for minimization of the $CO_2$ content are even more stringent than for gas pipeline transportation. In the LNG product, the $CO_2$ levels in the natural gas stream to be liquefied often need to be brought down to levels of less than about 100 ppmv (parts per million on a volume basis), or even to levels of less than about 50 ppmv. This is due to the fact that the $CO_2$ content in the natural gas stream must be carefully reduced to prevent excessive icing of the heat exchangers which are required in the liquefaction of the natural gas. It is desirable to utilize the process of the present invention for $CO_2$ removal from natural gas streams utilized for LNG production. Therefore, in certain embodiments of the present invention, the $CO_2$ content of the effluent stream from the present swing adsorption process is preferably less than about 100 ppmv $CO_2$, and even more preferably less than about 50 ppmv $CO_2$. As used herein, the term "natural gas" includes a gas obtained from a natural gas reservoir, any intermediate stream leading to the production of a natural gas product, or the final natural gas product itself.

Another desirable commercial process embodiment of the present invention is for use in the separation of synthetically produced gas streams that are obtained through a variety of reactive processes that utilize a carbonaceous source and an oxidant and/or heat. These synthetically produced gas streams find use, for example, as synthesis gas for the production of other chemical products and intermediates (e.g., methanol) as well as in the synthesis of higher molecular weight hydrocarbons (e.g., kerosene fuels, aviation grade fuels, diesel grade fuels or lube blending products obtained, for example, via Fischer-Tropsch synthesis) which themselves find use as final products or as intermediates for further functionalization or for the synthesis of other products. Similarly, these synthetically produced gas streams may also target the generation of enriched hydrogen streams for use as fuels (e.g., fuel cells) or for use in the chemical processing of hydrocarbons (e.g., hydrodesulfurization and hydrodenitrogenation). Depending on feed availability, process options and economics, a variety of carbonaceous sources can be used, ranging from gaseous (e.g., natural gas) to liquid (e.g., naphthas, heavy oils and residue, bitumens, or shale oils) to solids (e.g., coal). With respect to the oxygen source, pure oxygen, air, or steam (plus heat) are typically used. In some instances, only heat is applied to the carbonaceous source to produce a "gasification" gas mixture that contains lesser amounts of full combustion products, which may be used as fuel or chemicals. The specific composition of the synthetically produced gas is strongly dependent on the nature of the carbonaceous source, the oxidant and the use of heat (if any). The produced gas typically contains varying amounts of $H_2$, CO, $CO_2$, $H_2O$, $CH_4$ and $N_2$ as majority components and lesser amounts of sulfur and nitrogen containing species (e.g., $H_2S$ and $NH_3$) as well as other contaminants (e.g., COS). Depending on the intended use of the synthetically produced gas, various levels of purification and preconditioning are required. A particularly important step in the production of a synthetically produced gas is the removal of $CO_2$ from the product stream. The $CO_2$ in the synthetically produced gas is generally not beneficial as it does not incorporate into any subsequent reaction products and it does not add heating value. Additionally, the $CO_2$ present in the synthetically produced gas can exist in sufficiently high concentrations that can contribute to the corrosion of processing equipment, as well as contribute to greenhouse gas emissions.

One embodiment of the present invention is to provide a process feedstream comprising a synthetically produced gas to a swing adsorption process wherein the adsorbent material in the swing adsorption process is comprised of a ZIF material that has an adsorptive loading ratio for $CO_2$ over $CH_4$ of at least about 10 to remove at least a portion of the $CO_2$ from the process feedstream. In a more preferred embodiment of the present invention, a process feedstream comprising a synthetically produced gas is provided to a swing adsorption process wherein the adsorbent material in the swing adsorption process is comprised of a ZIF material that has an adsorptive loading ratio for $CO_2$ over $CH_4$ of at least about 15 to remove at least a portion of the $CO_2$ from the process feedstream. In an even more preferred embodiments of the present invention, the ZIF material utilized in this process has an adsorptive loading ratio for $CO_2$ over $CH_4$ of at least about 20, and most preferably an adsorptive loading ratio for $CO_2$ over $CH_4$ of at least 25.

In the process embodiment of the present invention above for $CO_2$ removal from synthetically produced gas streams, most of the $CH_4$ in the synthetically produced gas feedstream to the process will pass through the adsorbent material and be recovered in the effluent stream from the process. As described prior, in these processes the operating temperature is preferably chosen to allow the low to high loading transition exhibited in the isotherm for $CO_2$ to occur under the selected process conditions, while preventing this low to high loading transition to occur for $CH_4$ under the selected process conditions. Additionally, most of the $H_2$ in the synthetically produced gas inlet stream to the process will pass through the adsorption material and be recovered in the effluent stream from the process. The $CH_4$ in the obtained effluent stream can then be separated from the $H_2$ by conventional methods resulting in a higher purity $H_2$ stream. The $H_2$ stream thus obtained can be directly utilized as a final product or mixed with a carbon monoxide stream for use in further synthesis steps for the catalytic production, for example, of methanol or other liquid hydrocarbon products.

In a preferred embodiment of the present invention, the effluent stream (or "$CO_2$-lean product stream) produced in the process above for the removal of $CO_2$ from a synthetically produced gas contains less than about 5 vol % $CO_2$, and even more preferably less than about 3 vol % $CO_2$. It should also be noted, that as described above, there may be significant quantities of water and contaminants, such as, but not limited to $H_2S$ and $NH_3$, which may be physically damaging or operational hindering to the any of the embodiments of the ZIF-containing separations processes of the present invention.

Therefore, in preferred embodiments of the present invention, a portion of the contaminants are removed prior to contacting the target stream with the ZIF-containing process. There are many conventional processes that are known to those of skill in the art for the removal of such contaminants that may be utilized in conjunction with the processes of the present invention to reduce the concentration of these contaminants to acceptable levels prior to contacting the ZIF or ZIF-containing adsorbent materials disclosed herein.

Another desirable commercial process embodiment of the present invention is for use in the separation of $CO_2$ from $CH_4$ in landfill or biogenically produced gas streams. Landfill gas streams are defined herein as substantially gas phase streams that are produced from the substantially anaerobic biodegradation of organic matter in landfill disposal sites. In these landfill decomposition processes, the released gases are captured and processed for the recovery of valuable hydrocarbons which typically contain a significant concentration of methane. Similarly, biogenically produced gas streams are defined herein as any process that generates a methane-containing product stream from the anaerobic digestion or fermentation of biodegradable organic matter (e.g., manure, sewage, municipal waste, energy crops, etc.).

The capture and purification of landfill and biogenically produced gas streams is gaining more wide-spread commercial importance because it can simultaneously produce a valuable fuel product (i.e., $CH_4$) as well as contribute to a reduction of greenhouse gas emissions (i.e., $CO_2$ and $CH_4$). Both $CH_4$ and $CO_2$ are significant contributors to the greenhouse effect. The emissions from the underlying biodegradation processes generally lead to high concentrations of $CH_4$ and $CO_2$. Depending on the specific conditions of the landfill site or the biogenically produced gas process, the total combined $CH_4$ and $CO_2$ content of these streams can often be greater than about 50 vol % or even greater than about 70 vol %. The $CO_2$ content of the produced gas from these processes is typically very high, often possessing a $CO_2$ content of at least about 20 vol % and sometimes over 40 vol %. Although there are generally some additional contaminants such as $NH_3$, $H_2S$ and mercaptans present in these streams, typically, a sizable fraction of the gas is $CO_2$ and $CH_4$ and therefore an important separation in the cleanup of landfill and biogenically produced gas streams for commercial use is the separation of the $CO_2$ from the $CH_4$ present in the stream.

Another problem that makes it difficult and expensive to separate $CO_2$ from $CH_4$ in these landfill and biogenically produced gas streams is that these streams are often generated at very low pressures, often at pressures less than about 30 psig (206 kPa), or even at pressures less than 10 psig (69 kPa). In order for these streams to be separated by swing adsorption processes, the process feedstream must typically be pressurized up to above about 50 psig (345 kPa) or even 100 psig (689 kPa) prior to contacting most conventional adsorbent materials in order to obtain sufficient separation of the components. This is due to the fact that many conventional adsorbent materials require significant pressures to obtain adsorbed component loadings sufficient to make the size of the equipment small enough to meet economic and space requirements. It has been discovered that many ZIF materials can overcome these deficiencies of the current adsorbents due to their extremely high loading capacities for the selective component at very low pressures.

The results presented in FIGS. 12 and 13 for ZIF-7 and FIGS. 17 and 18 for ZIF-9, which exemplify the ZIF materials of the present invention, clearly show their adequacy for low pressure operation. In preferred embodiments of adsorption processes of the present invention, the landfill and biogenically produced gas streams contact the ZIF or ZIF-containing adsorbent material at a suitably chosen temperature and process feedstream pressures of less than about 50 psig (345 kPa). In other embodiments, the landfill and biogenically produced gas streams contact the ZIF or ZIF-containing adsorbent material at a suitably chosen temperature and process feedstream pressures of less than about 30 psig (207 kPa) or even less than about 10 psig (69 kPa). As can be seen from FIG. 15, in addition to the pressure level of the stream, the temperature level is also critical to the designing a swing adsorption process for optimum separation. As the pressure level decreases, the temperature can also be optionally decreased in order to ensure a significant loading of the adsorbate on the adsorbent material. As discussed prior, this characteristic of the ZIF-containing adsorbent materials can be significant in low-pressure applications of the present invention such as separating $CO_2$ from $CH_4$ present in landfill or biogenically produced gas streams where the pressures may be relatively low as noted above. However, the temperatures at which these streams are produced may be significantly high enough to shift the adsorption/desorption branches to $CO_2$ partial pressures above those required for optimum separations at low pressures. Therefore, in an embodiment of the present invention, the temperature of either the landfill or biogenically produced gas, or a process stream comprised of at least one of these gases, is reduced prior to contacting the ZIF-containing adsorbent material. In this manner, the compression required to raise the landfill or biogenically produced gas to optimum separation conditions for the present invention can be minimized, and in certain embodiments, the need for compression equipment to raise the pressure of the feedstream to the processes of the present invention may be completely eliminated.

With regard to high loadings at low pressures, for example, the sample of ZIF-7 from Example 1 and its corresponding adsorption loading at 301 K and 106.6 kPa from Example 6 shows an extremely large capacity for $CO_2$ of about 2.29 mmole/g of $CO_2$ at these substantially atmospheric pressure and temperature conditions (see FIG. 12). Similarly, the sample of ZIF-9 from Example 2 and its corresponding adsorption loading at 301 K and 106.6 kPa from Example 7 shows a large capacity for $CO_2$ of about 2.33 mmole/g of $CO_2$ at these substantially atmospheric pressure and temperature conditions (see FIG. 19). As discussed prior, ZIF materials, such as ZIF-7 and ZIF-9, can be valuable adsorbent materials for low pressure PSA, TSA, and PSA/TSA processes. In a preferred embodiment of the process of the present invention, a process feedstream comprised of a landfill or biogenically produced gas stream is provided to a swing adsorption process wherein the adsorbent material in the swing adsorption process is comprised of a ZIF material that has adsorptive loading ratio for $CO_2$ over $CH_4$ of at least about 10 to remove at least a portion of the $CO_2$ from the inlet stream. In a more preferred embodiment of the present invention, an process feedstream comprising a landfill or biogenically produced gas stream is provided to a swing adsorption process wherein the adsorbent material in the swing adsorption process is comprised of a ZIF material that has adsorptive loading ratio for $CO_2$ over $CH_4$ of at least about 20 to remove at least a portion of the $CO_2$ from the process feedstream. In an even more preferred embodiments of the present invention, the ZIF material utilized in this process has an adsorptive loading ratio for $CO_2$ over $CH_4$ of at least about 25.

It should be noted that although the processes of the present invention for separation of natural gas streams, synthetically produced gas streams, and landfill and biogenically produced gas streams have been explained above in terms of a swing adsorption configuration, the ZIF-containing membranes described above may also be utilized under similar process inlet conditions to selectively separate $CO_2$ from $CH_4$, and produce similar composition product streams as disclosed in the swing adsorption process embodiments above. In the processes utilizing ZIF-containing membranes to separate $CO_2$ from $CH_4$ in a process feedstream containing both components, it is desirable that the $CO_2$ selectively permeates through the ZIF-containing membrane process producing at least one $CO_2$-rich permeate stream wherein the $CO_2$-rich permeate stream has a higher vol % of $CO_2$ than the process feedstream that contacts the ZIF-containing membrane. Additionally, at least one $CO_2$-lean retentate stream is also produced by the process wherein a $CO_2$-lean retentate stream has a lower vol % of $CO_2$ than the process feedstream. The stream compositions, separations selectivities and properties of the final products produced by the ZIF-containing membrane process embodiments of the present invention are similar to those identified in the swing adsorption process embodiments described above.

Another important process in the industry concerning greenhouse gases, such as $CO_2$, is the sequestration of at least a portion of the $CO_2$ removed from a process stream. The terms "sequestration" or "$CO_2$ sequestration" as utilized herein are defined as the confinement of a waste stream containing at least 50 vol % of $CO_2$ in an underground structure, or repository, or in the deep ocean at pressures of at least 500 psig (3,447 kPa). Depending upon the sequestration process utilized, it may be desirable that the separation process of the present invention be operated so as to produce a high concentration of $CO_2$ in the $CO_2$-rich stream. This is especially desirable when high volumes of $CO_2$ are produced in a process, for example, in the extraction of natural gas streams where high concentrations of $CO_2$ are present in the wellhead gas. Due to the very large production rates of these high pressure natural gas fields, a very large amount of $CO_2$ is produced. Here, it is important that the gas stream to be sequestered contains a large concentration of $CO_2$ in order to reduce the size of the handling and compression equipment required as well as to reduce the energy costs associated with the sequestration of the $CO_2$. Reducing the overall volume of the gas stream to be sequestered also has the benefit of minimizing the storage requirements necessary for this sequestration.

However, the need to separate and sequester a portion of the $CO_2$ that is present in a process stream can apply to any process wherein $CO_2$ is produced as an unwanted by-product. In some of these processes, it is more important that a high percentage of the $CO_2$ produced by a process be separated and sequestered so that the $CO_2$ released to the atmosphere and/or the residual $CO_2$ remaining in the process gas is minimized. In this case, the separation processes of the present invention may be designed to minimize the amount of $CO_2$ that remains in the $CO_2$-lean product stream produced.

As such, the $CO_2$-rich product stream produced by the separation processes of the present invention can be further sequestered. In the separation of $CO_2$ from the valuable $CH_4$ in natural gas production, the $CO_2$ that is preferentially adsorbed in the separation process can be sequestered at high pressures in underground formations. It is desirable that these underground formations be located near the production site of the natural gas to minimize transportation costs. Underground formations that are suitable for sequestration of $CO_2$ include aquifers that have a top seal that prevents significant loss of the injected components, oil reservoirs, gas reservoirs, depleted oil reservoirs and depleted gas reservoirs. Typically the separated $CO_2$-rich product stream has to be recompressed to pressures greater than 2,000 psig (13,790 kPa) and often to pressures greater than 5,000 psig (34,474 kPa) to be injected into these types of underground formations. Therefore, it is beneficial that the process embodiment of the present invention utilized for the separation of the $CO_2$ from the $CH_4$ be able to produce the $CO_2$-rich product stream at high pressures in order to minimize the amount of compression necessary for the sequestration. As stated prior, in preferred embodiments of the present invention, $CO_2$-rich product streams can be produced by the present invention wherein the $CO_2$-rich product stream produced is at a pressure greater than about 250 psig, and even more preferably, the $CO_2$-rich product stream produced is at a pressure greater than about 500 psig.

In preferred embodiments of the present invention at least a portion of the $CO_2$-rich stream produced by the separation process of the current invention is sequestered. In preferred embodiments, the $CO_2$-rich stream that is produced has a $CO_2$ content of at least of 75 vol % wherein at least a portion of the $CO_2$-rich stream is sequestered. In a more preferred embodiment, the $CO_2$-rich stream has a $CO_2$ content of at least of 85 vol % wherein at least a portion of the $CO_2$-rich stream is sequestered. In other preferred embodiments of the present invention, the $CO_2$-lean product stream obtained has a $CO_2$ content of less than about 5 vol %, and more preferably less than about 2 vol %. The utilization of this process embodiment is particularly beneficial wherein the $CO_2$-lean stream is released to the atmosphere as an exhaust stream.

Although the present invention has been described in terms of specific embodiments, it is not so limited. Suitable alterations and modifications for operation under specific conditions will be apparent to those skilled in the art. It is therefore intended that the following claims be interpreted as covering all such alterations and modifications as fall within the true spirit and scope of the invention.

The Examples below are provided to illustrate the synthesis and the adsorption properties of a few select zeolitic imidazolate framework materials to illustrate the benefits of the present invention. These Examples only illustrate specific embodiments of the present invention and are not meant to limit the scope of the current invention.

EXAMPLES

In the following Examples 1 through 5, small amounts of Zeolitic Imidazolate Frameworks (or "ZIFs") samples were synthesized for use in testing for adsorption and separations processes that are described in detail in Examples 6 through 10. ZIFs are a unique type of microporous crystalline structures having framework topologies commonly found in zeolites and/or in other crystalline materials wherein each vertex is comprised of a single metal ion and each pair of connected adjacent vertices of the framework structure are linked by the nitrogen atoms of an imidazolate anion or its derivative. Each ZIF material with a specific type of solvent occluded is characterized by a unique X-ray diffraction pattern. However, due to the porous and flexible nature of ZIF framework structures, the X-ray diffraction pattern can be altered upon solvent-exchange or desolvation. The ZIF materials used in the gas adsorption screening studies were prepared according to published procedures with slight modifications in reaction scale and/or sample activation; see reference Park, K. S.; Ni, Z.; Côté, A. P.; Choi, J. Y.; Huang, R.; Uribe-Romo, F. J.; Chae, H. K.; O'Keeffe, M.; Yaghi, O. M. *Proc. Natl. Acad. Sci. U.S.A.* 2006, 103, 10186-10191, which is incorporated herein by reference and herein referred to as the "Park Reference".

The examples of ZIF materials provided herein are not meant to be limiting of the present invention in any manner. The general synthesis and structural characterization of some of the ZIF materials applicable to the present invention are presented in United States Patent Publication No. US2007/0202038A1 which is herein incorporated by reference.

Detailed synthesis procedures are described below in Examples 1 through 5 for selected ZIF materials.

Example 1

In this example, a ZIF-7 material was synthesized. The framework of ZIF-7 has a chemical composition of $ZnL_2$ (wherein L=benzimidazolate, i.e., the anion of benzimidazole) and a topology defined by the Zn cations that is identical to the zeolitic framework type SOD. SOD is a three-letter framework type code as defined by the International Zeolite Association ("IZA") in the "Atlas of Zeolite Framework Types" (Ch. Baerlocher, L. B. McCusker, D. H. Olson, Sixth Revised Edition, Elsevier Amsterdam, 2007).

In the synthesis of the ZIF-7 material, 9.00 g of zinc nitrate tetrahydrate ($Zn(NO_3)_2 \cdot 4H_2O$, 34.4 mmol) and 3.00 g of Benzimidazole (25.4 mmol) were dissolved in 900 ml DMF (N,N-Dimethylformamide) in a 1 liter glass jar. The jar was tightly capped and the reaction mixture was heated in an isothermal oven at 373 K for 48 hours. After reaction, the mother liquor was decanted. The solid crystallized on the side wall and the bottom part of the jar was collected, washed with and stored in DMF and labeled "as-synthesized ZIF-7".

In order to activate the ZIF-7, the as-synthesized solid was heated under vacuum at 473 K for 24 hours, transferred to a 120 ml vial, immersed in acetonitrile (c.a. 100 ml) and soaked at 348 K for 48 hours. The acetonitrile-exchanged ZIF-7 was loaded in a glass tube and evacuated on a vacuum line apparatus at room-temperature for 16 hours to remove the solvent molecules residing in its pores. 2.10 g of activated ZIF-7 was obtained, corresponding to 55% yield (based on Benzimidazole).

For gas adsorption experiments, the acetonitrile-exchanged ZIF-7 was loaded directly in the sample holder of the gravimetric gas-adsorption unit and activated in-situ by using the conditions described in Example 6.

FIG. 1 shows a comparison of the experimental powder X-ray diffraction ("PXRD") patterns of the as-synthesized and the acetonitrile-exchanged ZIF-7 samples and the calculated PXRD pattern (shown as the stick pattern) based on the single crystal structure of ZIF-7 reported in the "Park Reference" as referenced herein. The PXRD patterns as shown in FIG. 1 are plotted as the diffraction intensity (in arbitrary units) against the diffraction angle two theta (in degrees).

The high purity of the as-synthesized ZIF-7 sample is evidenced by the coincidence of experimental and calculated PXRD patterns. It is worth noting the slight differences between the two experimental PXRD patterns of ZIF-7. The pattern of as-synthesized ZIF-7 is indexed to rhombohedral space group R$\bar{3}$, a=b=22.927 Å, c=15.603 Å whereas the pattern of acetonitrile-exchanged ZIF-7 is indexed to the same space group with a=b=22.522 Å and c=15.760 Å. The data suggest a slight distortion of the unit cell of ZIF-7 upon solvent-exchange.

Figure 2:
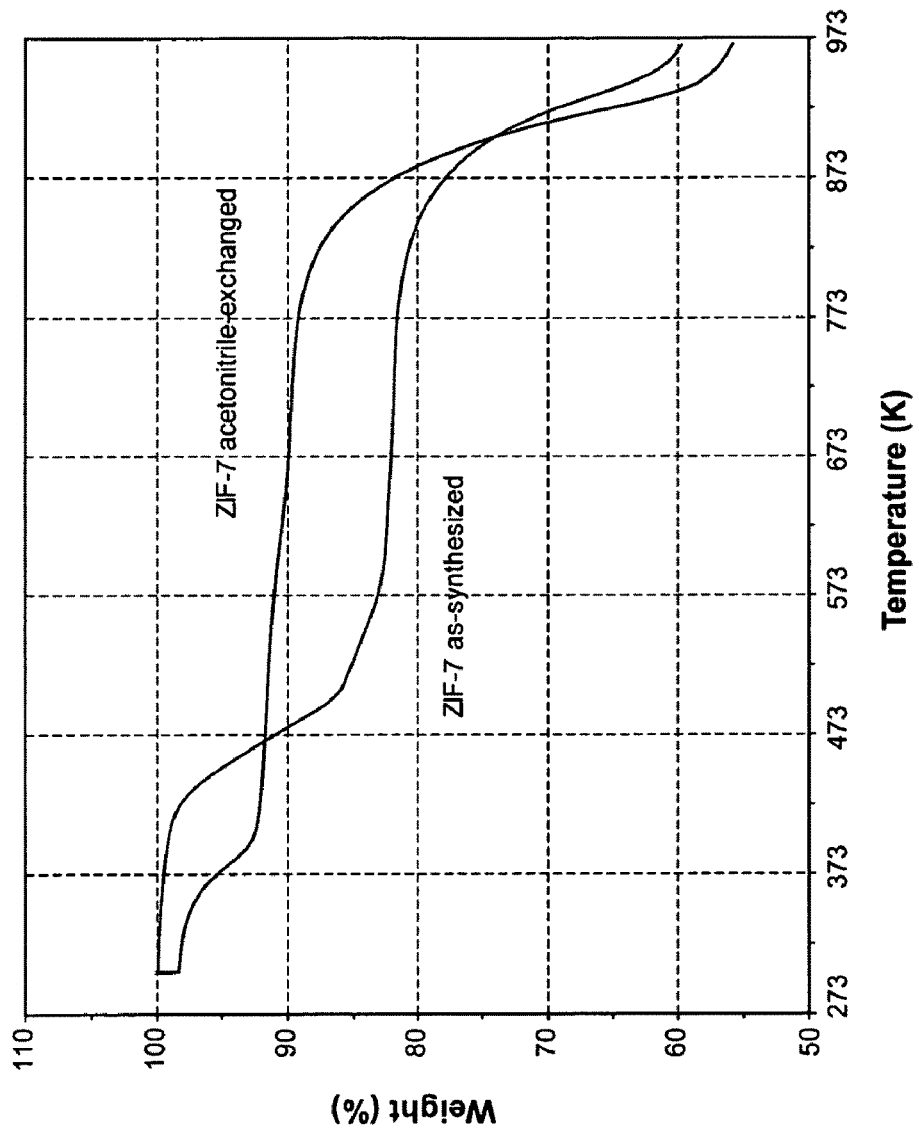
FIG. 2 shows the thermogravimetric analyses ("TGA"s) for the as-synthesized and acetonitrile-exchanged ZIF-7 samples of Example 1 herein.

FIG. 2 shows the thermogravimetric analyses ("TGA") for the as-synthesized and the acetonitrile-exchanged ZIF-7 samples in nitrogen atmosphere. The activation conditions described above were chosen based on TGA data.

Figure 11:
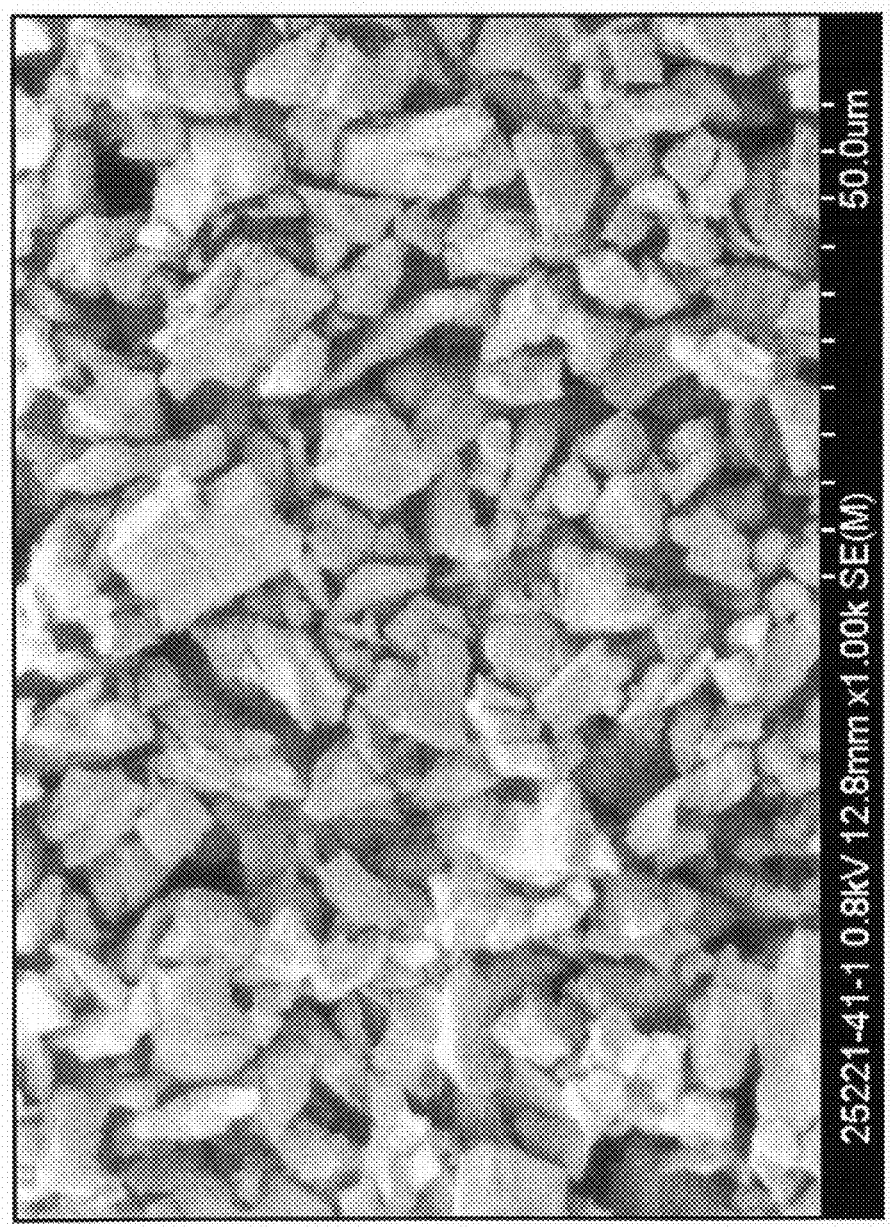
FIG. 11 is a Scanning Electron Microscopy ("SEM") image of a ZIF-7 sample of Example 6.

FIG. 11 is a Scanning Electron Microscopy ("SEM") image of a sample of ZIF-7 produced.

Example 2

In this example, a ZIF-9 material was synthesized. The framework of ZIF-9 has a chemical composition of $CoL_2$ (wherein L=benzimidazolate, i.e., the anion of benzimidazole) and a topology defined by the Co cations that is identical to the zeolitic framework type SOD. SOD is a three-letter framework type code as defined by the International Zeolite Association ("IZA") in the "Atlas of Zeolite Framework Types" (Ch. Baerlocher, L. B. McCusker, D. H. Olson, Sixth Revised Edition, Elsevier Amsterdam, 2007).

In the synthesis of the ZIF-9 material, 1.26 g of cobalt nitrate hexahydrate ($Co(NO_3)_2.6H_2O$, 4.33 mmol) and 0.360 g of Benzimidazole (3.05 mmol) were dissolved in 108 ml DMF (N,N-Dimethylformamide) in a 120 ml vial. The vial was tightly capped and the reaction mixture was heated in an isothermal oven at 373 K for 96 hours. After reaction, the mother liquor was decanted. The solid crystallized on the side wall and the bottom part of the jar was collected, washed with and stored in DMF and labeled "as-synthesized ZIF-9".

In order to activate the ZIF-9, the as-synthesized solid was heated under vacuum at 473 K for 24 hours, transferred to a 20 ml vial, immersed in acetonitrile (c.a. 15 ml) and soaked at 348 K for 48 hours. The acetonitrile-exchanged ZIF-9 was loaded in a glass tube and evacuated on a vacuum line apparatus at room-temperature for 16 hours to remove the solvent molecules residing in its pores. 0.07 g of activated ZIF-9 was obtained, corresponding to 15% yield (based on Benzimidazole).

For gas adsorption experiments, the acetonitrile-exchanged ZIF-9 was loaded directly in the sample holder of the gravimetric gas adsorption unit and activated in-situ by using the conditions described in Example 7.

Figure 3:
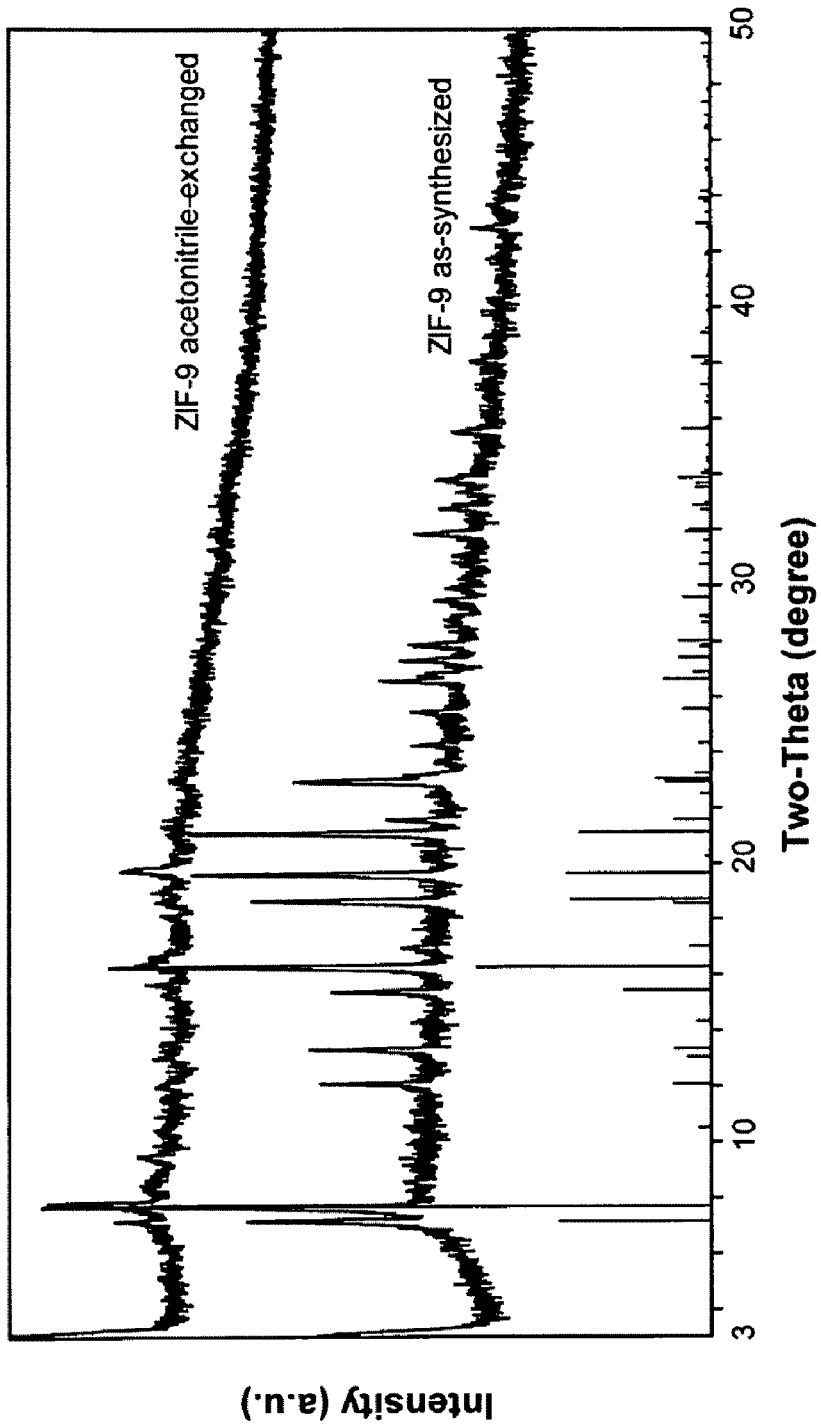
FIG. 3 is the experimental powder X-ray diffraction ("PXRD") patterns of the as-synthesized and acetonitrile-exchanged ZIF-9 samples of Example 2 herein. The calculated PXRD pattern (shown as the vertical stick patterns in the figure) for ZIF-9 based on the single crystal structure of ZIF-9 reported in the "Park Reference" as referenced herein is also shown in the figure.

FIG. 3 shows a comparison of the experimental powder X-ray diffraction ("PXRD") patterns of the as-synthesized and the acetonitrile-exchanged ZIF-9 samples and the calculated PXRD pattern (shown as the stick pattern) based on the single crystal structure of ZIF-9 reported in the "Park Reference" as referenced herein. The PXRD patterns as shown in FIG. 3 are plotted as the diffraction intensity (in arbitrary units) against the diffraction angle two theta (in degrees).

The high purity of the as-synthesized ZIF-9 sample is evidenced by the coincidence of experimental and calculated PXRD patterns. The relatively large background in the PXRD pattern of the as-synthesized ZIF-9 sample cannot be attributed to the existence of amorphous impurities because only purple cubic crystals are observed within the sample by optical microscopy. The PXRD data suggests that Co-containing ZIF-9 is intrinsically of lower crystallinity when compared to its isomorphous Zn-containing material ZIF-7 (comparing FIGS. 1 and 3).

Figure 4:
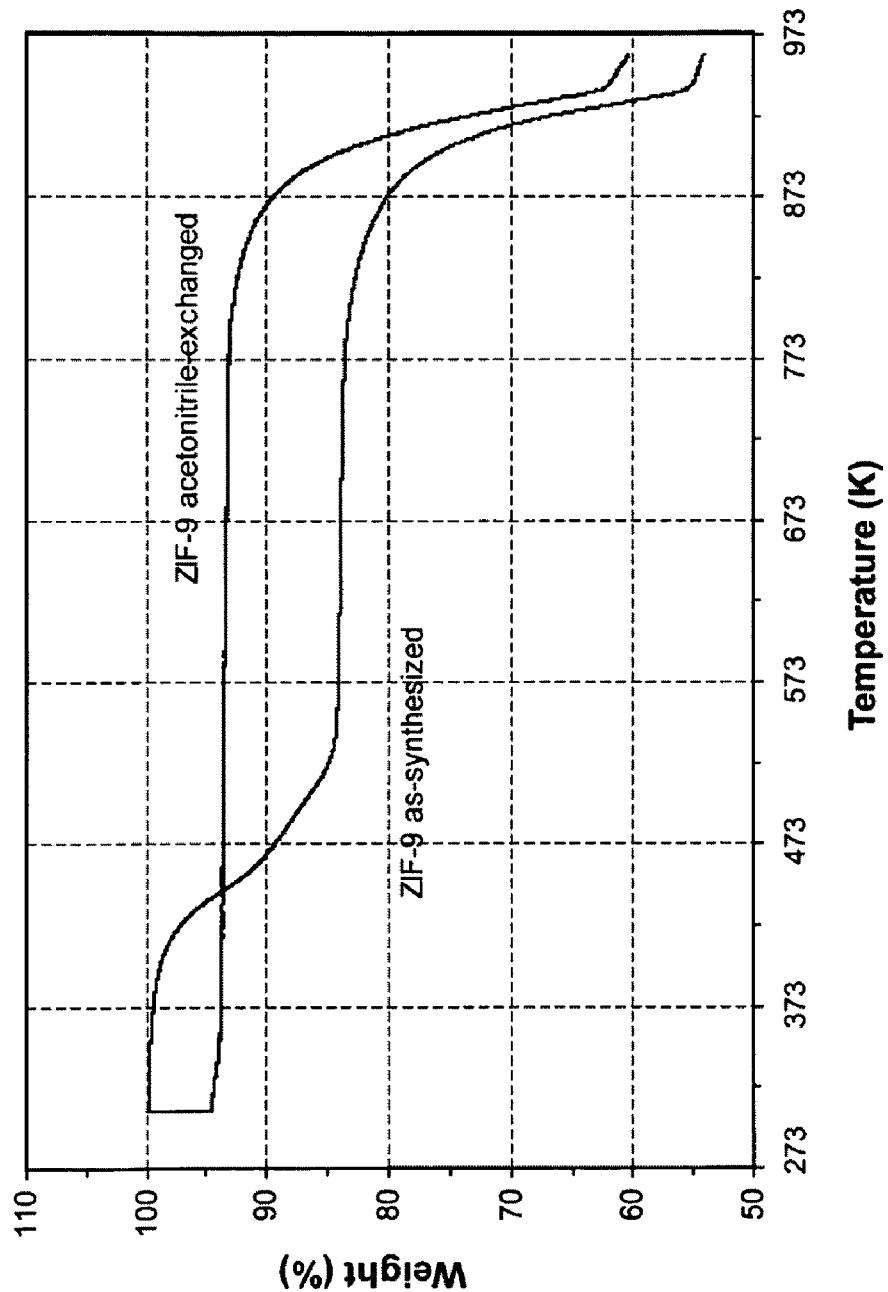
FIG. 4 shows the thermogravimetric analyses ("TGA"s) for the as-synthesized and acetonitrile-exchanged ZIF-9 samples of Example 2 herein.

FIG. 4 shows the thermogravimetric analyses ("TGA") for the as-synthesized and the acetonitrile-exchanged ZIF-9 samples in nitrogen atmosphere. The activation conditions described above were chosen based on TGA data.

Figure 16:
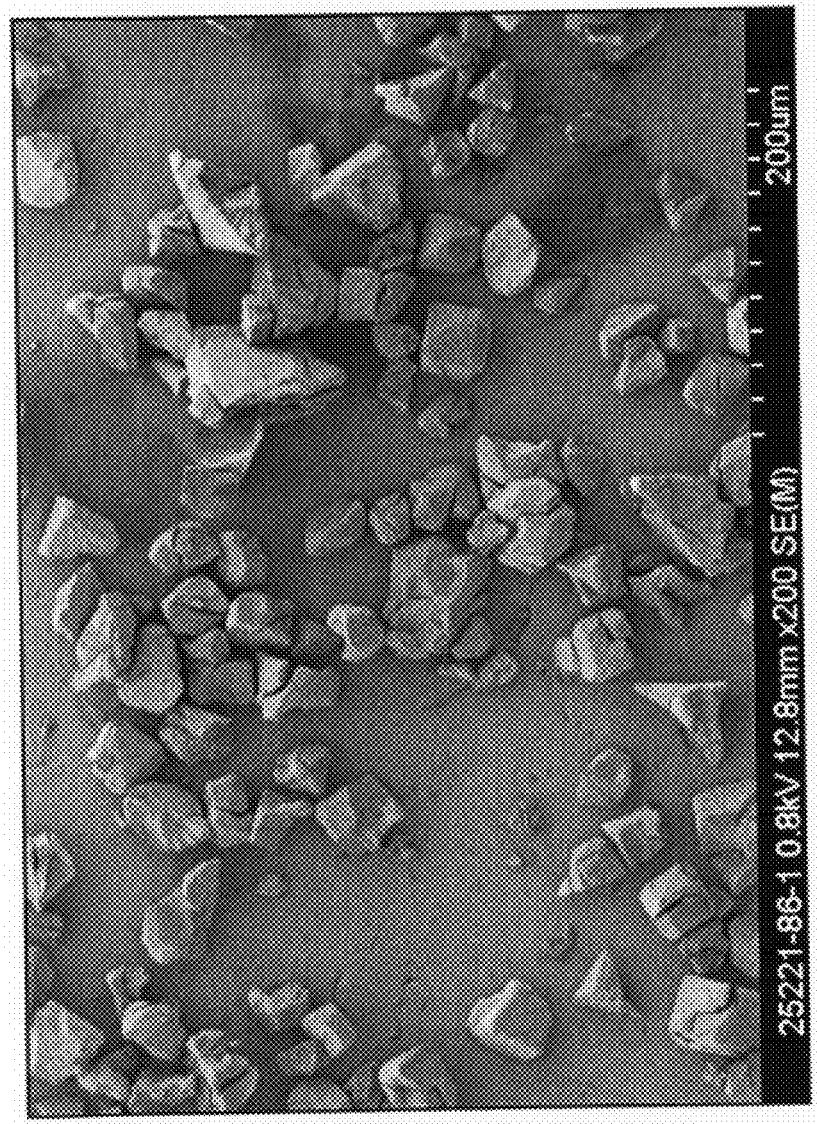
FIG. 16 is a Scanning Electron Microscopy ("SEM") image of a ZIF-9 sample of Example 7.

FIG. 16 is a Scanning Electron Microscopy ("SEM") image of a sample of ZIF-9 produced.

Example 3

In this example, a ZIF-1 material was synthesized. The framework of ZIF-1 has a chemical composition of $ZnL_2$ (wherein L=imidazolate, i.e., the anion of imidazole) and a topology defined by the Zn cations that is identical to the zeolitic framework type BCT. BCT is a three-letter framework type code as defined by the International Zeolite Association ("IZA") in the "Atlas of Zeolite Framework Types" (Ch. Baerlocher, L. B. McCusker, D. H. Olson, Sixth Revised Edition, Elsevier Amsterdam, 2007).

In the synthesis of the ZIF-1 material, 1.25 g of zinc nitrate tetrahydrate ($Zn(NO_3)_2.4H_2O$, 4.77 mmol) and 2.75 g of Imidazole (40.4 mmol) were dissolved in 100 ml DMAc (N,N-Dimethylacetamide) in a 120 ml glass vial. The vial was tightly capped and the reaction mixture was heated in an isothermal oven at 358 K for 72 hours. After reaction, the mother liquor was decanted. The solid crystallized on the side wall and the bottom part of the vial was collected and washed with DMF (N,N-Dimethylformamide) to remove any residual mother liquor. The product was then transferred to a 20 ml vial, stored in DMF and labeled "as-synthesized ZIF-1".

In order to activate the ZIF-1, the as-synthesized solid was immersed in acetonitrile (c.a. 15 ml) for a total of 72 hours. The solvent volume was replaced every 24 hours. The acetonitrile-exchanged ZIF-1 was loaded in a glass tube and evacuated on a vacuum line apparatus at room temperature for 16 hours to remove the solvent molecules residing in its pores. 0.13 g of activated ZIF-1 was obtained, corresponding to 14% yield (based on zinc nitrate tetrahydrate). Alternatively, the as-synthesized ZIF-1 was activated by exchanging with toluene followed by heating under vacuum at 443 K for 2 hours.

For gas adsorption experiments, the acetonitrile-exchanged or toluene-exchanged ZIF-1 was loaded directly in the sample holder of the gravimetric gas adsorption unit and activated in-situ by using the conditions described in Example 8.

Figure 5:
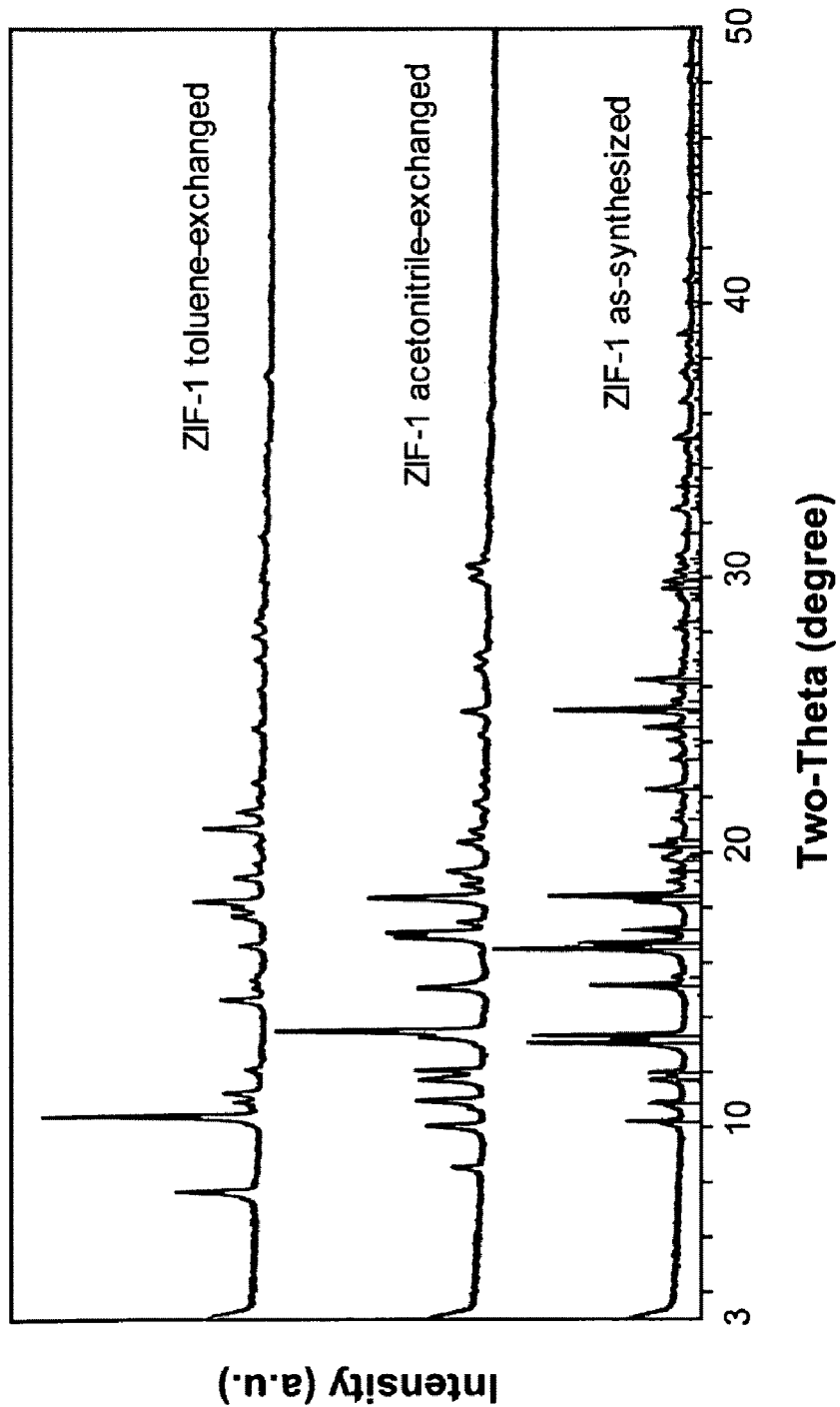
FIG. 5 is the experimental powder X-ray diffraction ("PXRD") patterns of the as-synthesized, the acetonitrile-exchanged and the toluene-exchanged ZIF-1 samples of Example 3 herein. The calculated PXRD pattern (shown as the vertical stick patterns in the figure) for ZIF-1 based on the single crystal structure of ZIF-1 reported in the "Park Reference" as referenced herein is also shown in the figure.

FIG. 5 shows a comparison of the experimental powder X-ray diffraction ("PXRD") patterns of the as-synthesized, the acetonitrile-exchanged and the toluene-exchanged ZIF-1 samples and the calculated PXRD pattern (shown as the stick pattern) based on the single crystal structure of ZIF-1 reported in the "Park Reference" as referenced herein. The PXRD patterns as shown in FIG. 5 are plotted as the diffraction intensity (in arbitrary units) against the diffraction angle two theta (in degrees).

The high purity of the as-synthesized ZIF-1 sample is evidenced by the coincidence of experimental and calculated PXRD patterns. It is worth noting the differences between the three experimental PXRD patterns of ZIF-1. The pattern of as-synthesized ZIF-1 is indexed to monoclinic space group $P2_1/c$, a=9.699 Å, b=15.185 Å, c=16.555 Å, β=116.9° whereas the pattern of acetonitrile-exchanged ZIF-1 is indexed to the same space group with a=10.098 Å, b=14.649 Å, c=17.300 Å, β=119.5° and pattern of toluene-exchanged ZIF-1 is indexed to a space group of orthorhombic symmetry Pnn2 with a=15.708 Å, b=9.455 Å, c=16.969 Å. The data suggest distortions of the unit cell of ZIF-1 upon solvent-exchange. We point out that high-symmetry analog of ZIF-1 does exist. The single crystal structure of such a component was reported in the "Park Reference" as referenced herein (ZIF-2 having the same framework topology as ZIF-1, orthorhombic, Pbca, a=9.679 Å, b=24.114 Å, c=24.450 Å).

Figure 6:
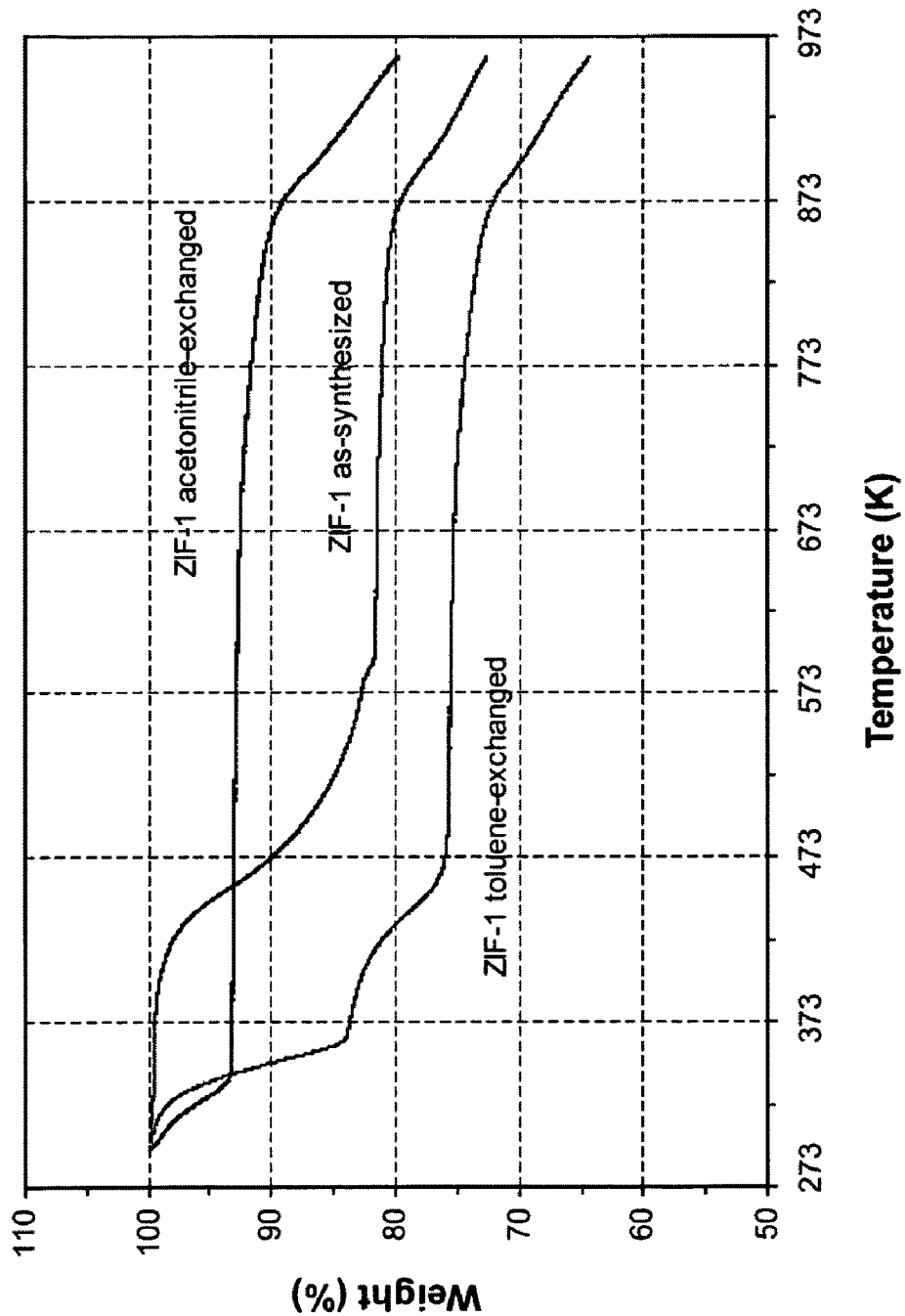
FIG. 6 shows the thermogravimetric analyses ("TGA"s) for the as-synthesized, the acetonitrile-exchanged and the toluene-exchanged ZIF-1 samples of Example 3 herein.

FIG. 6 shows the thermogravimetric analyses ("TGA") for the as-synthesized, the acetonitrile-exchanged and the toluene-exchanged ZIF-1 samples in nitrogen atmosphere. The activation conditions described above were chosen based on TGA data.

Figure 20:
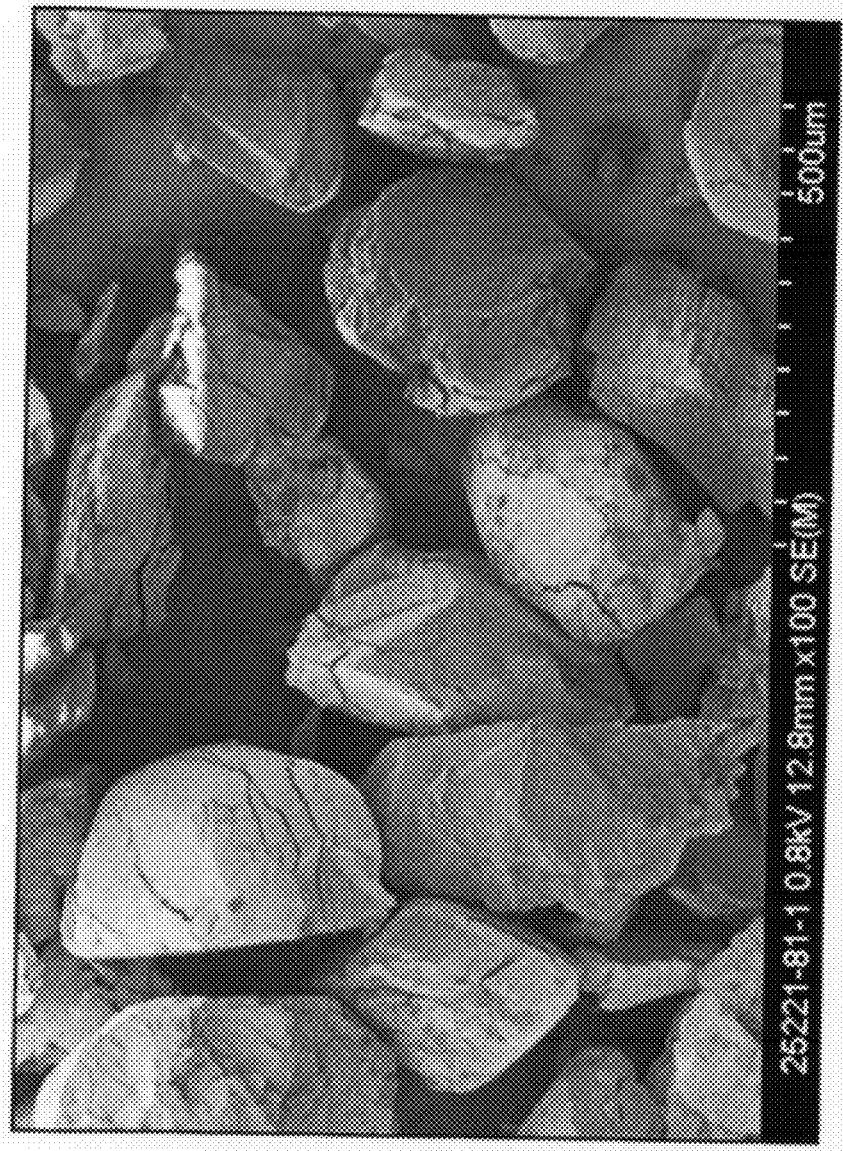
FIG. 20 is a Scanning Electron Microscopy ("SEM") image of a ZIF-1 (acetonitrile-exchanged) sample of Example 8.
Figure 21:
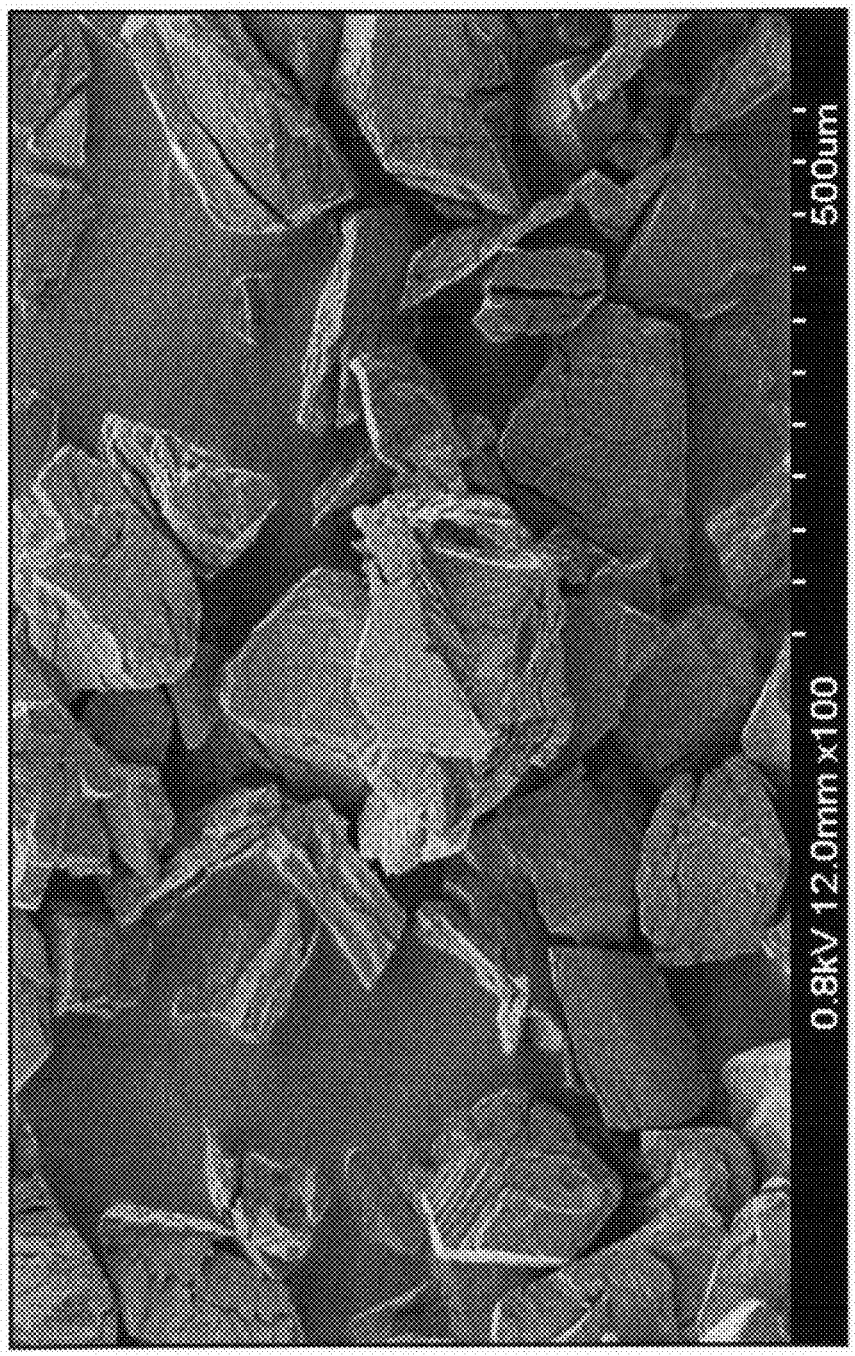
FIG. 21 is a Scanning Electron Microscopy ("SEM") image of a ZIF-1 (toluene-exchanged) sample of Example 8.

FIG. 20 is a Scanning Electron Microscopy ("SEM") image of a sample of ZIF-1 (acetonitrile-exchanged) produced. FIG. 21 is a Scanning Electron Microscopy ("SEM") image of a sample of ZIF-1 (toluene-exchanged) produced.

Example 4

In this example, a ZIF-11 material was synthesized. The framework of ZIF-11 has a chemical composition of $ZnL_2$ (wherein L=benzimidazolate, i.e., the anion of benzimidazole) and a topology defined by the Zn cations that is identical to the zeolitic framework type RHO. RHO is a three-letter framework type code as defined by the International Zeolite Association ("IZA") in the "Atlas of Zeolite Framework Types" (Ch. Baerlocher, L. B. McCusker, D. H. Olson, Sixth Revised Edition, Elsevier Amsterdam, 2007).

In the synthesis of the ZIF-11 material, 0.330 g of zinc nitrate hexahydrate ($Zn(NO_3)_2.6H_2O$, 1.11 mmol) and 0.990 g of Benzimidazole (8.38 mmol) were dissolved in 100 ml DEF (N,N-Diethylformamide) in a 120 ml glass vial. The vial was tightly capped and the reaction mixture was heated in an isothermal oven at 373 k for 96 hours. After reaction, the mother liquor was decanted. The solid crystallized on the side wall and the bottom part of the vial was collected and washed with DMF (N,N-Dimethylformamide) repeatedly to remove any residual mother liquor and an amorphous by-product. The product was then transferred to a 20 ml vial and the DMF solvent was decanted. After the addition of chloroform (c.a. 15 ml), the vial was capped and the mixture was immersed in an ultrasonic bath for 30 minutes to mechanically detach an unidentified dense-phase from the surfaces of ZIF-11 crystals. Two layers of solids appeared after the vial sat on a level surface undisturbed for 30 minutes. The solid layer floating on the surface of chloroform was carefully collected using a pipette and transferred to another 20 ml vial. The solid was washed with and stored in DMF and labeled "purified ZIF-11".

In order to activate the ZIF-11, the purified solid was immersed in methanol (c.a. 15 ml) for a total of 72 hours. The solvent volume was replaced every 24 hours. The methanol-exchanged ZIF-11 was loaded in a glass tube and evacuated on a vacuum line apparatus. After the removal of external methanol solvent at room temperature, the solid was heated under vacuum at 423 K for 16 hours to remove the solvent molecules residing in the pores of the ZIF-11. A 0.09 g sample of activated ZIF-11 was thus obtained, corresponding to 27% yield (based on zinc nitrate hexahydrate).

For gas adsorption experiments, the methanol-exchanged ZIF-11 was loaded directly in the sample holder of the gravimetric gas adsorption unit and activated in-situ by using the conditions described in Example 9.

Figure 7:
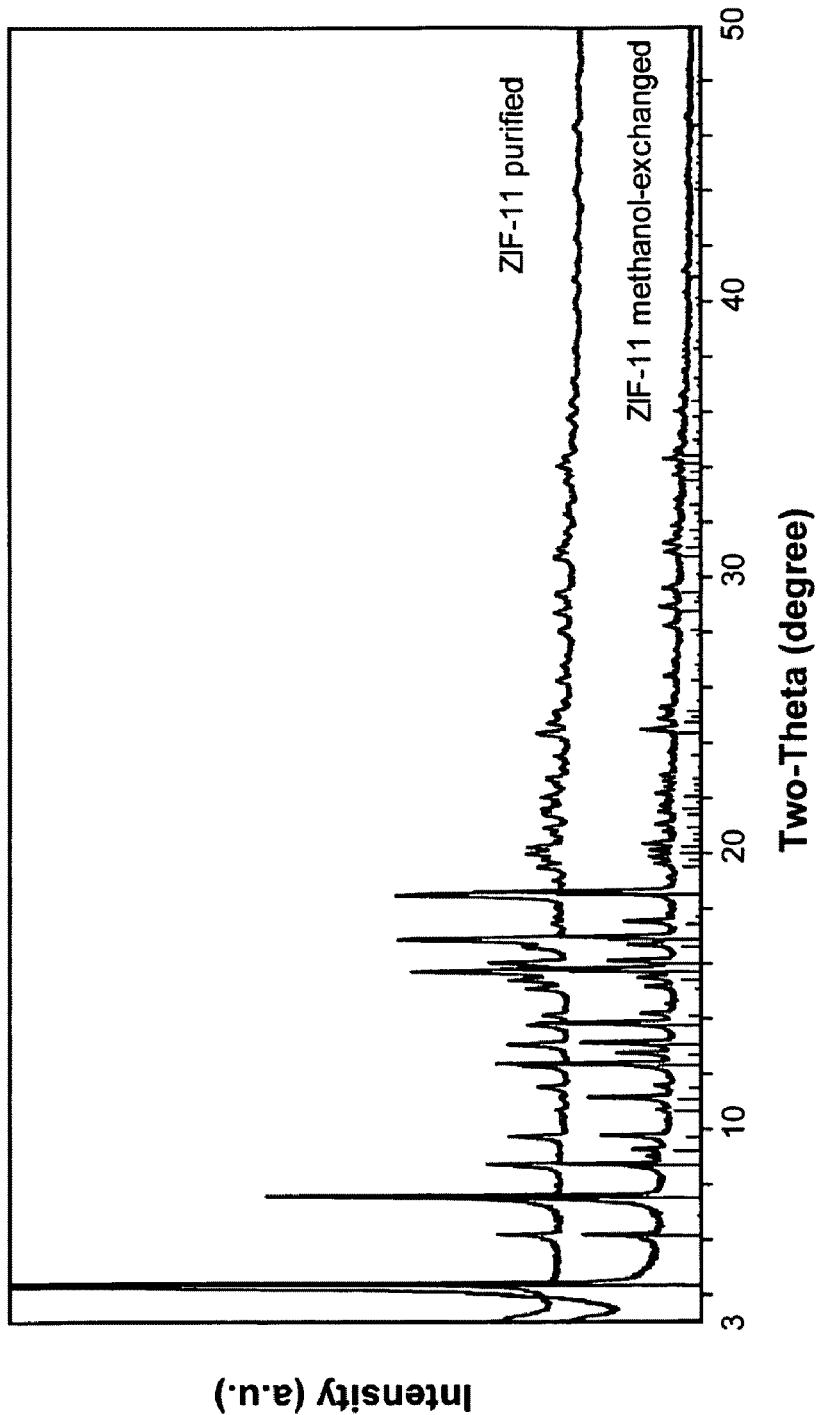
FIG. 7 is the experimental powder X-ray diffraction ("PXRD") patterns of the purified and methanol-exchanged ZIF-11 samples of Example 4 herein. The calculated PXRD pattern (shown as the vertical stick patterns in the figure) for ZIF-11 based on the single crystal structure of ZIF-11 reported in the "Park Reference" as referenced herein is also shown in the figure.

FIG. 7 shows a comparison of the experimental powder X-ray diffraction ("PXRD") patterns of the purified and the methanol-exchanged ZIF-11 samples and the calculated PXRD pattern (shown as the stick pattern) based on the single crystal structure of ZIF-11 reported in the "Park Reference" as referenced herein. The PXRD patterns as shown in FIG. 7 are plotted as the diffraction intensity (in arbitrary units) against the diffraction angle two-theta (in degrees).

The high purity of the sample is evidenced by the coincidence of experimental and calculated PXRD patterns. It is worth noting the slight differences between the two experimental PXRD patterns of ZIF-11. After methanol-exchange, the intensities of the diffraction peaks were altered and the peak positions were systematically shifted to higher two-theta angle (in degrees).

Figure 8:
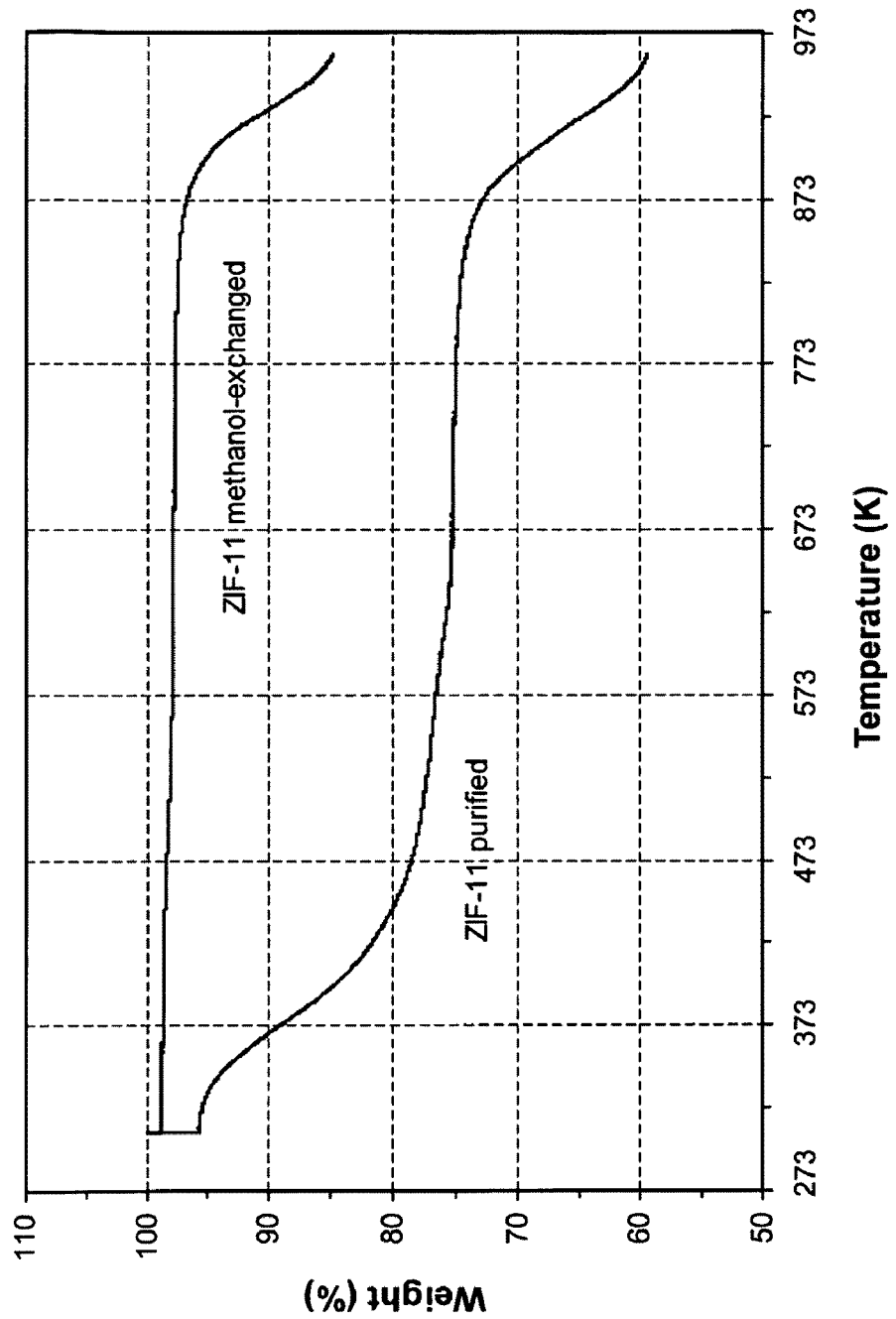
FIG. 8 shows the thermogravimetric analyses ("TGA"s) for the purified and methanol-exchanged ZIF-11 samples of Example 4 herein.

FIG. 8 shows the thermogravimetric analyses ("TGA") for the purified and the methanol-exchanged ZIF-11 samples in nitrogen atmosphere. The activation conditions described above were chosen based on TGA data.

Figure 24:
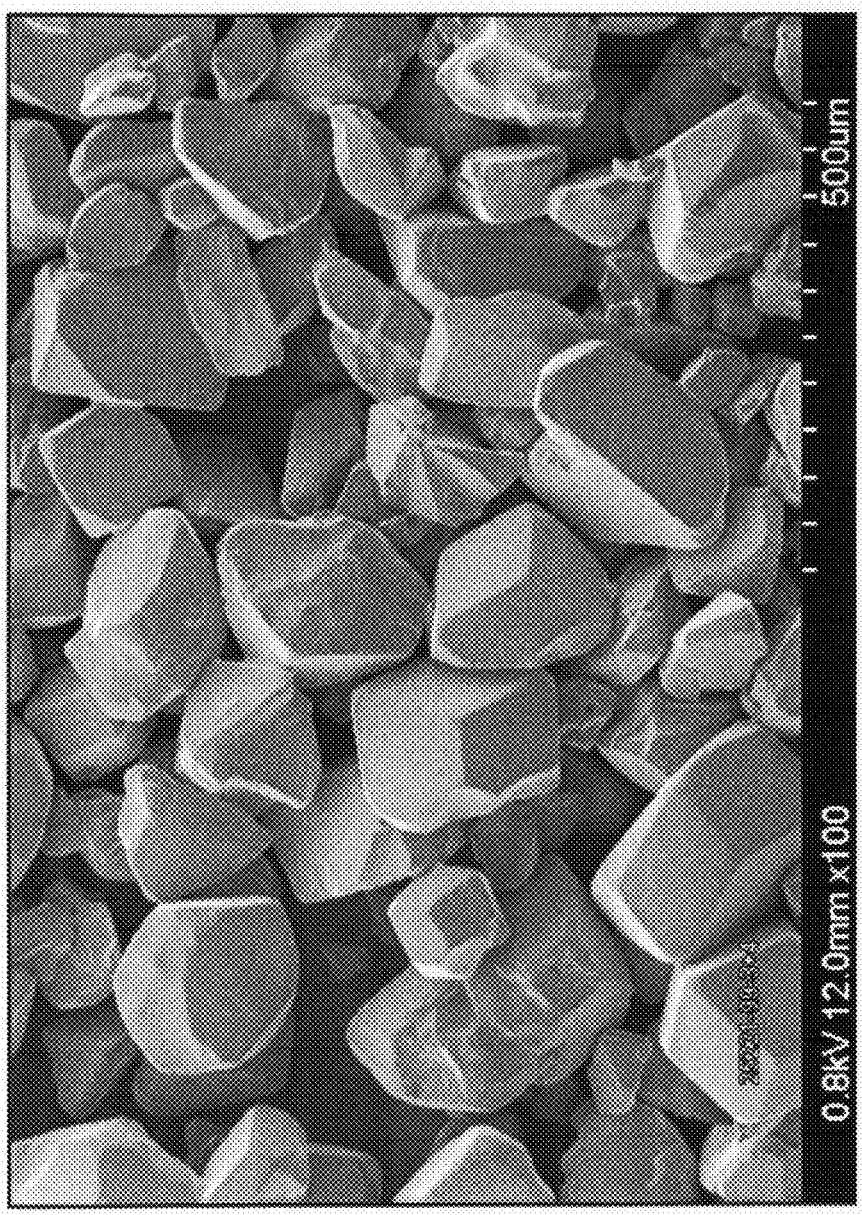
FIG. 24 is a Scanning Electron Microscopy ("SEM") image of a ZIF-11 sample of Example 9.

FIG. 24 is a Scanning Electron Microscopy ("SEM") image of a sample of ZIF-11 produced.

Example 5

In this example, a ZIF-8 material was synthesized. The framework of ZIF-8 has a chemical composition of $ZnL_2$ (wherein L=2-Methylimidazolate, i.e., the anion of 2-Methylimidazole) and a topology defined by the Zn cations that is identical to the zeolitic framework type SOD. SOD is a three-letter framework type code as defined by the International Zeolite Association ("IZA") in the "Atlas of Zeolite Framework Types" (Ch. Baerlocher, L. B. McCusker, D. H. Olson, Sixth Revised Edition, Elsevier Amsterdam, 2007).

In the synthesis of the ZIF-8 material, 10.50 g of zinc nitrate tetrahydrate ($Zn(NO_3)_2.4H_2O$, 40.2 mmol) and 3.00 g of 2-Methylimidazole (36.5 mmol) were dissolved in 900 ml DMF (N,N-Dimethylformamide) in a 1 liter glass jar. The jar was tightly capped and the reaction mixture was heated in an isothermal oven at 413 K for 24 hours. After reaction, the mother liquor was decanted. The solid crystallized on the side wall and the bottom part of the jar was collected and washed with DMF repeatedly to remove any residual mother liquor and an amorphous by-product. The product was then transferred to a 120 ml vial and the DMF solvent was decanted. After the addition of chloroform (c.a. 100 ml), the vial was capped and the mixture was immersed in an ultrasonic bath for 30 minutes to mechanically detach zinc oxide particles from the surfaces of ZIF-8 crystals. Two layers of solids appeared after the vial sat on a level surface undisturbed for 30 minutes. The solid layer floating on the surface of chloroform was carefully collected using a pipette and transferred to another 120 ml vial. The solid was washed with and stored in DMF and labeled "purified ZIF-8".

In order to activate the ZIF-8, the purified solid was immersed in methanol (c.a. 100 ml) for a total of 72 hours. The solvent volume was replaced every 24 hours. This methanol-exchanged ZIF-8 was loaded in a glass tube and evacuated on a vacuum line apparatus. After the removal of external methanol solvent at room-temperature, the solid was heated under vacuum at 523 K for 16 hours to remove the solvent molecules residing in the pores of ZIF-8. 1.70 g of activated ZIF-8 was obtained, corresponding to 41% yield (based on 2-Methylimidazole).

For gas adsorption experiments, the methanol-exchanged ZIF-8 was loaded directly in the sample holder of the gravimetric gas adsorption unit and activated in-situ by using the conditions described in Example 10.

Figure 9:
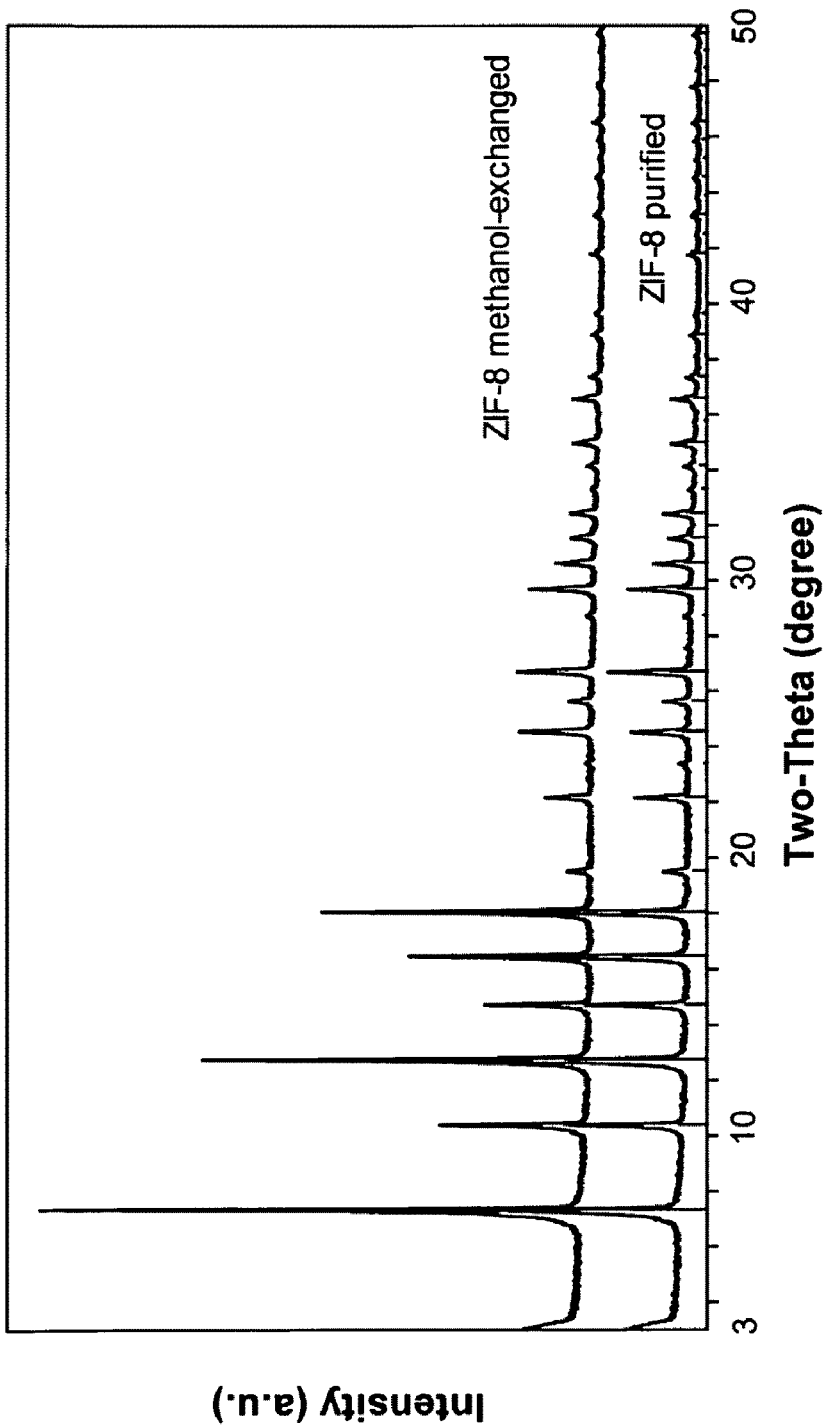
FIG. 9 is the experimental powder X-ray diffraction ("PXRD") patterns of the purified and methanol-exchanged ZIF-8 samples of Example 5 herein. The calculated PXRD pattern (shown as the vertical stick patterns in the figure) for ZIF-8 based on the single crystal structure of ZIF-8 reported in the "Park Reference" as referenced herein is also shown in the figure.

FIG. 9 shows a comparison of the experimental powder X-ray diffraction ("PXRD") patterns of the purified and the methanol-exchanged ZIF-8 samples and the calculated PXRD pattern (stick pattern) based on the single crystal structure of ZIF-8 reported in the "Park Reference" as referenced herein. The high purity of the sample is evidenced by the coincidence of experimental and calculated PXRD patterns. The PXRD patterns as shown in FIG. 9 are plotted as the diffraction intensity (in arbitrary units) against the diffraction angle two theta (in degrees).

Figure 10:
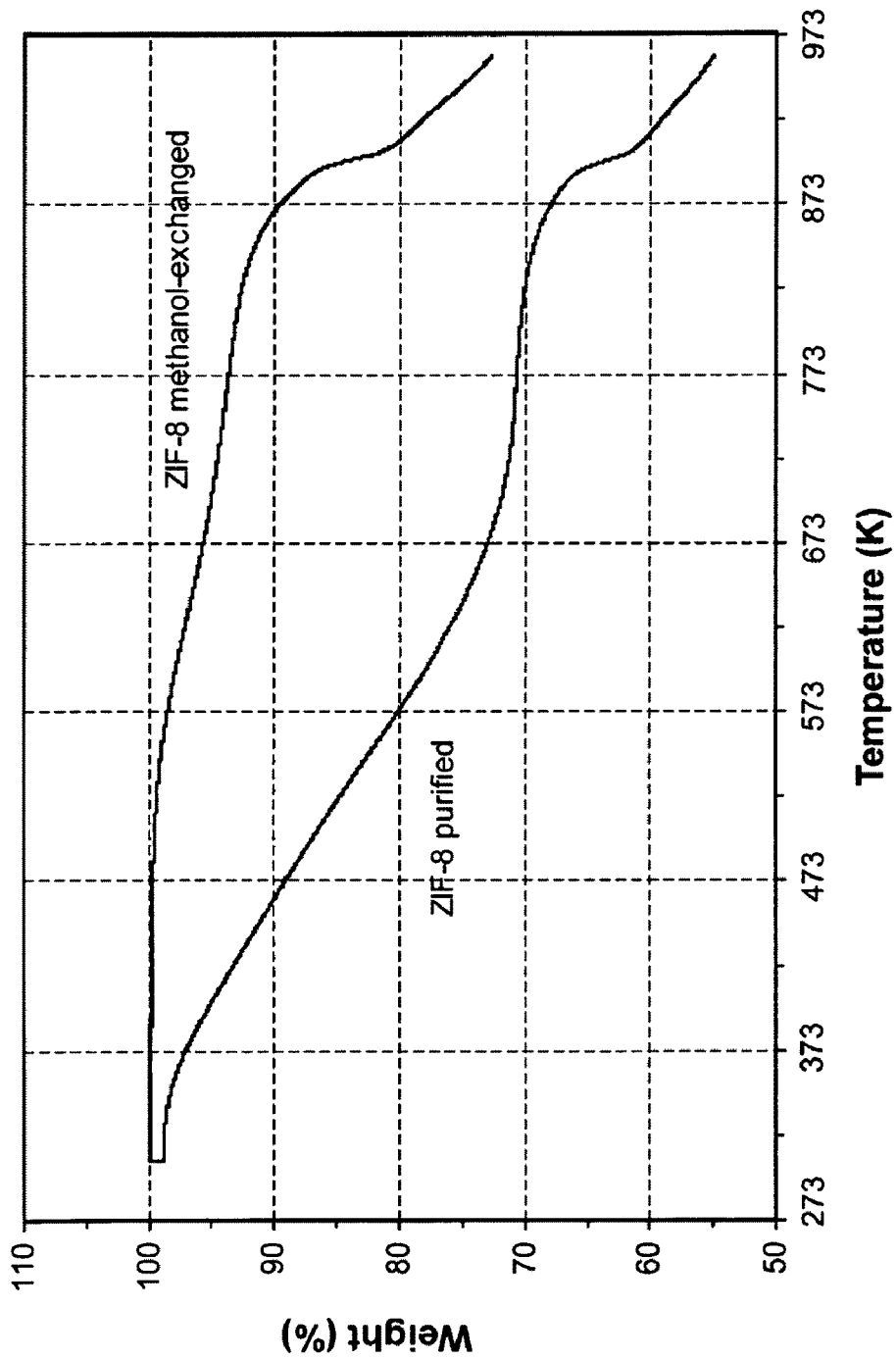
FIG. 10 shows the thermogravimetric analyses ("TGA"s) for the purified and methanol-exchanged ZIF-8 samples of Example 5 herein.

FIG. 10 shows the thermogravimetric analyses ("TGA") for the purified and the methanol-exchanged ZIF-8 samples in nitrogen atmosphere. The activation conditions described above were chosen based on TGA data.

Figure 27:
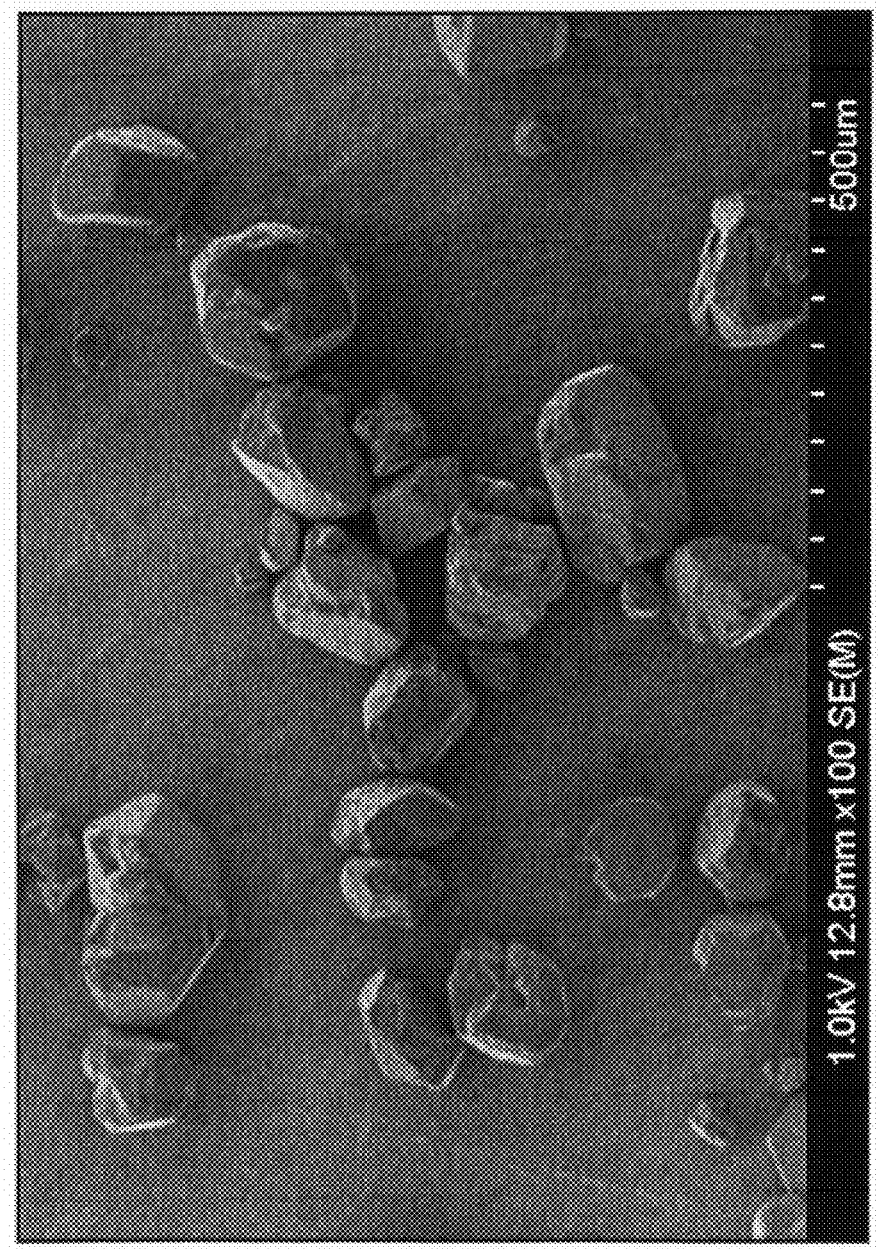
FIG. 27 is a Scanning Electron Microscopy ("SEM") image of a ZIF-8 sample of Example 10.

FIG. 27 is a Scanning Electron Microscopy ("SEM") image of a sample of ZIF-8 produced.

Examples 6-10

In Examples 6 through 10 herein, a Cahn® microbalance apparatus (TG121, 0.1 µg) was used to gravimetrically characterize the adsorption/desorption properties of gases and hydrocarbons (i.e., adsorbates) in various zeolitic imidazolate frameworks (i.e., adsorbents). Experiments were carried out on various adsorbate-adsorbent pairs to determine the adsorption isotherms for the various ZIF materials synthesized in Examples 1 through 5 above. At a constant temperature, the equilibrium adsorbate loading was measured at various adsorbate pressures up to 106.6 kPa. In order to capture any potential hysteretic behavior, for each isotherm half of the experimental points were measured in the adsorption mode (i.e., increasing the pressure from vacuum to the maximum pressure of 106.6 kPa) and the other half of the experimental points were measured in the desorption mode (i.e., decreasing the pressure from the maximum pressure of 106.6 kPa to vacuum). In all experiments, a LabVIEW® computer software was used to automatically set, control and monitor the sequence of steps followed in each experiment.

The adsorbate feed was brought into the feed manifold from lecture bottles or from house supply lines containing high purity gases and hydrocarbons. The feed manifold was in contact with the adsorbent located in the sample holder of the microbalance. The adsorbate pressure within the feed manifold was controlled between vacuum and 106.6 kPa by a MKS® Type 146 Measurement and Control System, which was connected to the computer via RS232 communications. The feed manifold was equipped with three MKS® 120A pressure transducers (0-0.0133 kPa, 0-1.33 kPa and 0-133 kPa) that provided the adsorbate pressure information to the controller. The controller actuated two electronic valves to adjust the adsorbate pressure within the feed manifold. One valve (MKS 0248A, Type 0010RK) was connected to the adsorbate feed supply and the other valve (MKS 0248A, Type 10000RV) was connected to the vacuum line. A Pfeiffer® TSU 261 turbomolecular pump was used to achieve the vacuum conditions.

Typically, prior to the adsorption isotherm measurements, about 15-90 mg of adsorbent was loaded in the microbalance at 301 K. In order to avoid the contacting of the adsorbent with ambient air, the adsorbent was fully immersed in an excess of a specified solvent (i.e., an amount well in excess of that required to fill its internal pore volume). The solvent was removed through the use of dynamic vacuum. In some cases, where the solvent was held more strongly within the interior of the adsorbate, heating was also used. Typically, the following steps (all under dynamic vacuum) were applied: (a) outgassing at 301 K for a prescribed duration, (b) heating to a prescribed temperature and kept there for a prescribed duration, (c) cooling to 301 K. Because the microbalance was tare just prior to loading the sample, the dry weight was directly obtained from the microbalance upon completion of the clean-up procedure. The type of solvent, the heating temperature as well as the duration of the steps was dependent on the particular ZIF material under study. For a given ZIF sample, the same clean-up steps were repeated each time a new successive experiment was conducted. Prior to removing the sample from the microbalance, the first and/or second adsorption experiments were repeated. These repeat experiments revealed excellent reproducibility, confirming the adequacy of the experimental adsorption isotherm procedures as well as the stability of the samples throughout the adsorption experiments. X-ray measurements of the removed samples further confirmed their integrity.

Example 6

In this example, adsorption isotherm experiments were carried out on ZIF-7 samples obtained from the synthesis detailed in Example 1 above in compliance with the general testing procedures for Examples 6-10 described above.

For the testing of each absorbate in this experiment, a sample of ZIF-7 was loaded with acetonitrile as the solvent. It was out-gassed for 6 hrs at 301 K under dynamic vacuum. No further heating was applied. The dry weight was 46.68 mg. The same clean-up procedure was applied to ZIF-7 prior to all subsequent experiments with other adsorbates. A Scanning Electron Microscopy ("SEM") image of this sample is shown in FIG. 11. FIG. 12 shows the $CO_2$ adsorption isotherm on ZIF-7 at 301 K. The ordinate displays the equilibrium adsorption loading in typical units of mmole/g. The lower abscissa displays the absolute $CO_2$ pressure in kPa. The upper abscissa displays the relative $CO_2$ pressure, where the normalizing pressure $P_0$ corresponds to the $CO_2$ saturation pressure at 301 K. From thermodynamic equilibrium vapor pressure data, a value of 6583.8 kPa was estimated for $P_0$. The filled and open symbols identify the corresponding adsorption and desorption branches, respectively (the adsorption branch is shown with filled diamond legend and the desorption branch is shown with open diamond legend).

In accordance with the testing procedures, an adsorption isotherm for methane, $CH_4$, was also generated and is shown together in FIG. 13 with the adsorption/desorption isotherm from FIG. 12 above. In the testing regime of this example, methane did not exhibit the separate adsorption and desorption branches as was exhibited for carbon dioxide and therefore, the adsorption and desorption curves for methane in this regime overlap for ZIF-7. As can be seen from FIG. 13, at the upper test pressure of 106.6 kPa@301 K, the adsorption loading of carbon dioxide, $CO_2$, was significantly larger than the adsorption loading for methane, $CH_4$, on the ZIF-7 material.

FIG. 14 is a bar graph comparing the corresponding adsorption loadings of the ZIF-7 material for carbon dioxide, $CO_2$, and methane, $CH_4$, at test conditions of 301 K and 106.6 kPa obtained from the tests above. As can be seen from this bar graph, the adsorption loading of the ZIF-7 material for $CO_2$ at 106.6 kPa@301 K was approximately 2.29 mmole/g while the adsorption loading for $CH_4$ was approximately 0.09 mmole/g. At these conditions, the adsorptive loading ratio for $CO_2$ over $CH_4$ is approximately 25.4, illustrating the high selectivity of the ZIF-7 material for $CO_2$ over $CH_4$, making ZIF-7 a suitable material for use in the present invention.

Additional isotherms for ZIF-7 were performed at different temperatures to investigate the adsorption/desorption characteristics of ZIF-7 at higher temperatures. The adsorption isotherms of ZIF-7 for $CO_2$ performed at 301 K, 308 K, and 323 K are shown in FIG. 15. As can be seen in FIG. 15, consistent with adsorption-based principles, as the temperature is increased from 301 K to 308 K, the transition from low to high $CO_2$ loading is displaced to higher pressures. This figure shows that comparable adsorption loadings of $CO_2$ on ZIF-7 occur at a correspondingly increased partial pressure. FIG. 15 also shows that at 323 K, the transition from low to high $CO_2$ loading does not take place under the conditions that were tested up to the maximum test pressure of 106.6 kPa. Such behavior is equivalent to that of $CH_4$ as exhibited in FIG. 13, that due to weaker $CH_4$ interactions with the adsorbent, $CH_4$ is unable to undergo the transition to a high loading state. It is this interplay of variables involving the adsorbate, adsorbent, pressure and temperature that can be used to an advantage in designing effective swing adsorption processes in accordance with the present invention for effectively separating $CO_2$ from $CH_4$ in gas mixtures containing both components.

Example 7

In this example, adsorption isotherm experiments were carried out on ZIF-9 samples obtained from the synthesis detailed in Example 2 above in compliance with the general testing procedures for Examples 6-10 described above.

For the testing of each absorbate in this experiment, a sample of ZIF-9 was loaded with acetonitrile as the solvent. It was out-gassed for 6 hrs at 301 K under dynamic vacuum. No further heating was applied. The dry weight was 56.35 mg. The same clean-up procedure was applied to ZIF-9 prior to all subsequent experiments with other adsorbates. A Scanning Electron Microscopy ("SEM") image of this sample is shown in FIG. 16. FIG. 17 shows the $CO_2$ adsorption isotherm on ZIF-9 at 301 K. The ordinate displays the equilibrium adsorption loading in typical units of mmole/g. The lower abscissa displays the absolute $CO_2$ pressure in kPa. The upper abscissa displays the relative $CO_2$ pressure, where the normalizing pressure $P_0$ corresponds to the $CO_2$ saturation pressure at 301 K. From thermodynamic equilibrium vapor pressure data, a value of 6583.8 kPa was estimated for $P_0$. The filled and open symbols identify the corresponding adsorption and desorption branches, respectively (the adsorption branch is shown with filled diamond legend and the desorption branch is shown with open diamond legend).

In accordance with the testing procedures, an adsorption isotherm for methane, $CH_4$, was also generated and is shown together in FIG. 18 with the adsorption/desorption isotherm from FIG. 17 above. In the testing regime of this example, methane did not exhibit the separate adsorption and desorption branches as was exhibited for carbon dioxide and therefore, the adsorption and desorption curves for methane in this regime overlap for ZIF-9. As can be seen from FIG. 18, at the upper test pressure of 106.6 kPa@301 K, the adsorption loading of carbon dioxide, $CO_2$, was significantly larger than the adsorption loading for methane, $CH_4$, on the ZIF-9 material.

FIG. 19 is a bar graph comparing the corresponding adsorption loadings of the ZIF-9 material for carbon dioxide, $CO_2$, and methane, $CH_4$, at test conditions of 301 K and 106.6 kPa obtained from the tests above. As can be seen from this bar graph, the adsorption loading of the ZIF-9 material for $CO_2$ at 106.6 kPa@301 K was approximately 2.33 mmole/g while the adsorption loading for $CH_4$ was approximately 0.08 mmole/g. At these conditions, the adsorptive loading ratio for $CO_2$ over $CH_4$ is approximately 29.1, illustrating the high selectivity of the ZIF-9 material for $CO_2$ over $CH_4$, making ZIF-9 a suitable material for use in the present invention.

Example 8

In this example, adsorption isotherm experiments were carried out on ZIF-1 samples obtained from the synthesis detailed in Example 3 above in compliance with the general testing procedures for Examples 6-10 described above.

For the testing of the acetonitrile-exchanged ZIF-1 sample, a portion of the ZIF-1 sample produced and activated as in Example 3 was loaded with acetonitrile as the solvent. It was out-gassed for 6 hrs at 301 K under dynamic vacuum. No further heating was applied. The dry weight was 69.64 mg. The same clean-up procedure was applied to the acetonitrile-exchanged ZIF-1 prior to all subsequent experiments with other adsorbates. A Scanning Electron Microscopy ("SEM") image of the acetonitrile-exchanged ZIF-1 sample is shown in FIG. 20.

For the testing of the toluene-exchanged ZIF-1 sample, a portion of the ZIF-1 sample produced and activated as in Example 3 was loaded with toluene as the solvent. It was out-gassed for 6 hrs at 301 K under dynamic vacuum, heated to 443 K for 2 hrs and then cooled to 301 K. The dry weight was 46.21 mg. The same clean-up procedure was applied to the toluene-exchanged ZIF-1 prior to all subsequent experiments with other adsorbates. A Scanning Electron Microscopy ("SEM") image of toluene-exchanged ZIF-1 sample is shown in FIG. 21.

Figure 22:
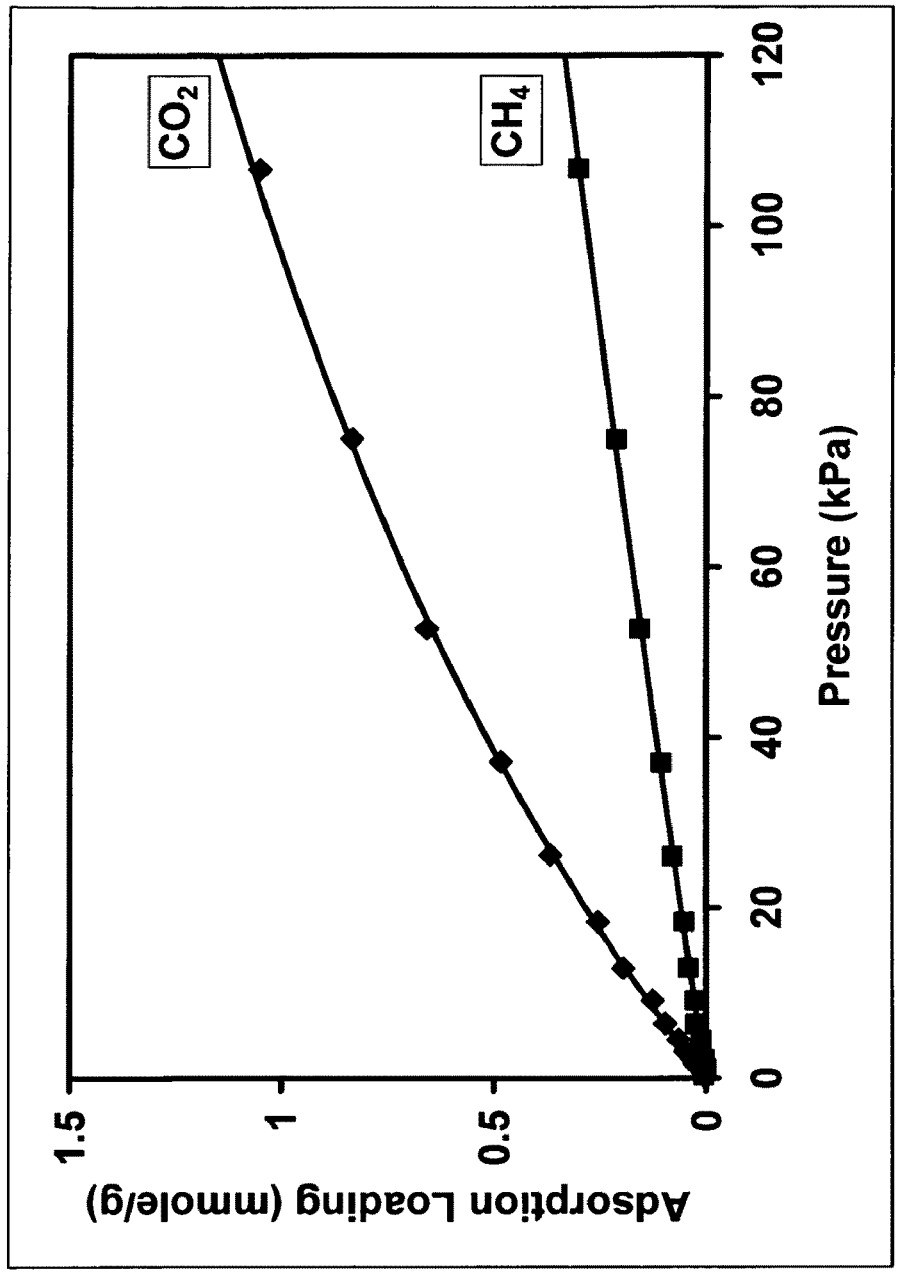
FIG. 22 shows the $CO_2$ adsorption isotherm and the $CH_4$ adsorption isotherm at 301 K for a ZIF-1 (acetonitrile-exchanged) sample of Example 8.

FIG. 22 shows the adsorption isotherms of the acetonitrile-exchanged ZIF-1 for carbon dioxide, $CO_2$, and methane, $CH_4$, at 301 K. The ordinate displays the equilibrium adsorption loading in typical units of mmole/g. The abscissa displays the absolute pressure of the adsorbate in kPa. As can be seen from FIG. 22, at the upper test pressure of 106.6 kPa@301 K, the adsorption loading of carbon dioxide, $CO_2$, was higher than the adsorption loading for methane, $CH_4$, on the acetonitrile-exchanged ZIF-1 material.

Figure 23:
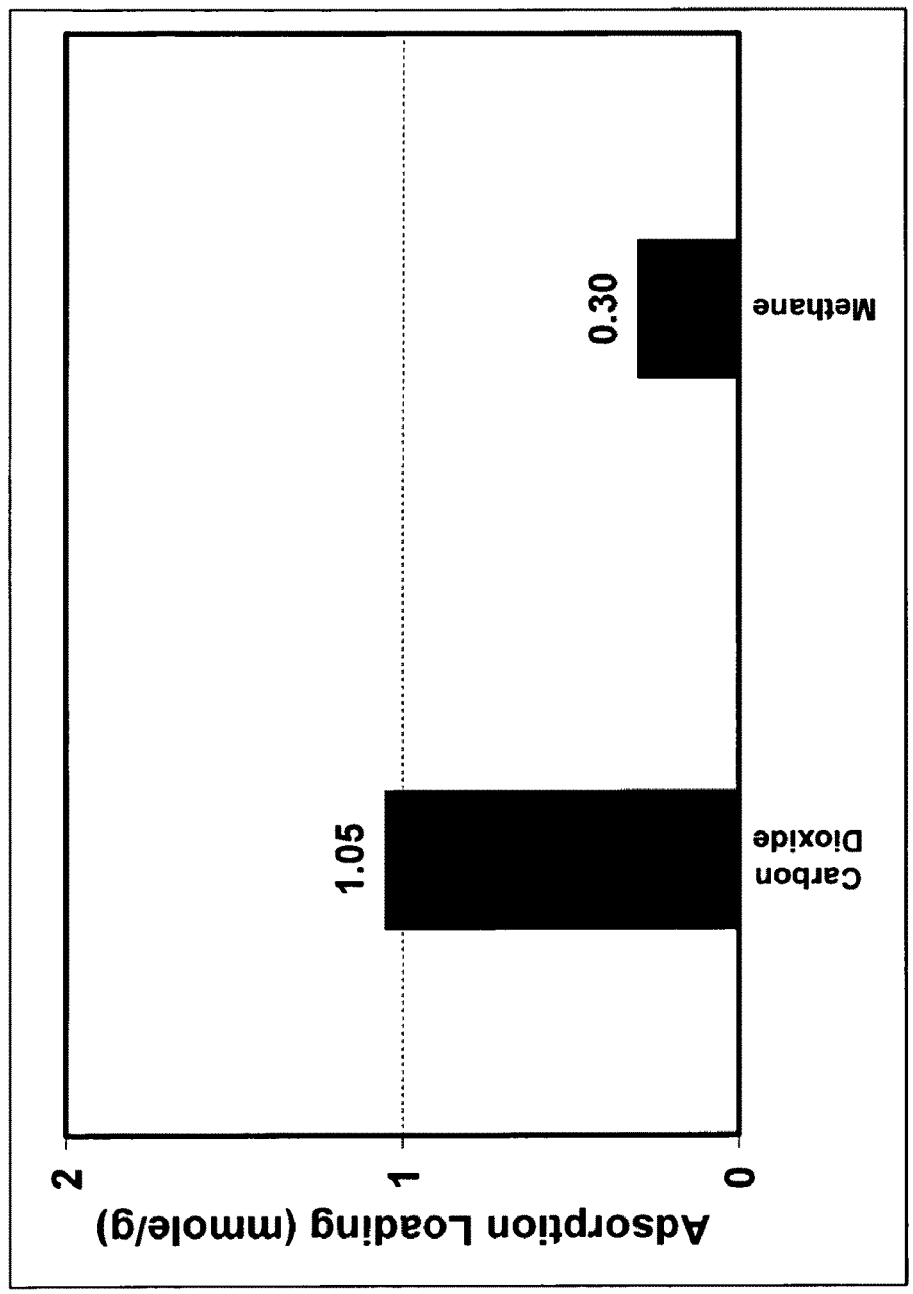
FIG. 23 is a bar graph comparing the adsorption loadings of a ZIF-1 (acetonitrile-exchanged) sample of Example 8 for $CO_2$ and $CH_4$ at 301 K and 106.6 kPa.

FIG. 23 is a bar graph comparing the corresponding adsorption loadings of the acetonitrile-exchanged ZIF-1 material for carbon dioxide, $CO_2$, and methane, $CH_4$, at test conditions of 301 K and 106.6 kPa obtained from the tests above. As can be seen from this bar graph, the adsorption loading of the acetonitrile-exchanged ZIF-1 material for $CO_2$ at 106.6 kPa@301 K was approximately 1.05 mmole/g while the adsorption loading for $CH_4$ was approximately 0.30 mmole/g. However, at these conditions, the adsorptive loading ratio for $CO_2$ over $CH_4$ was only approximately 3.5. This example illustrates that the acetonitrile-exchanged ZIF-1 does not possess an adsorptive loading ratio high enough to meet the requirements of the present invention.

It should be noted that, although not shown, the toluene-exchanged ZIF-1 material exhibits similar adsorption loading characteristics as the acetonitrile-exchanged ZIF-1 material.

Example 9

In this example, adsorption isotherm experiments were carried out on ZIF-11 samples obtained from the synthesis detailed in Example 4 above in compliance with the general testing procedures for Examples 6-10 described above.

Figure 25:
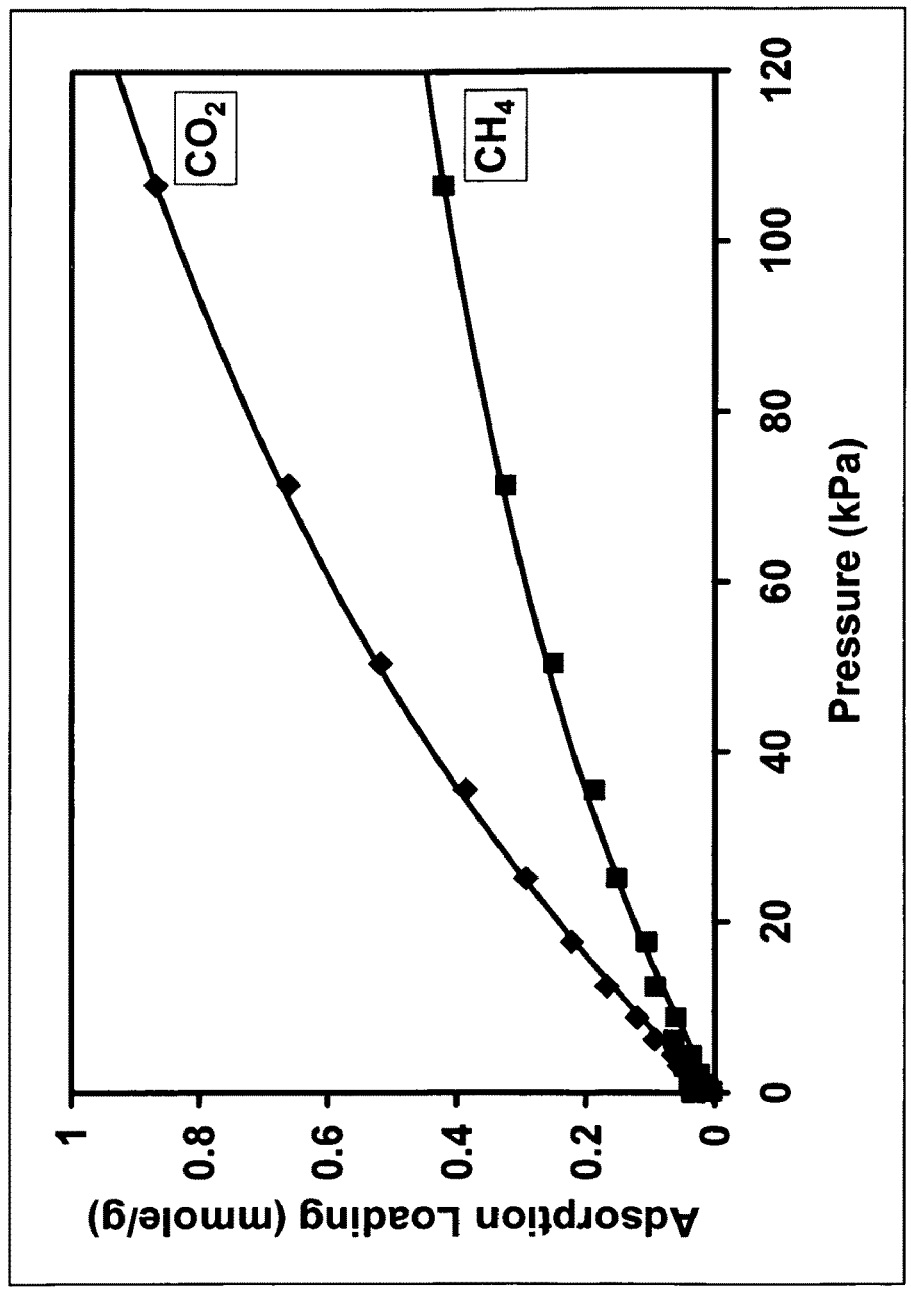
FIG. 25 shows the $CO_2$ adsorption isotherm and the $CH_4$ adsorption isotherm at 301 K for a ZIF-11 sample of Example 9.

For the testing of each absorbate in this experiment, a sample of ZIF-11 was loaded with methanol as the solvent. It was out-gassed for 2 hrs at 301 K under dynamic vacuum, heated to 423 K for 3 hrs, and then cooled to 301 K. The dry weight was 82.07 mg. The same clean-up procedure was applied to ZIF-11 prior to all subsequent experiments with other adsorbates. A Scanning Electron Microscopy ("SEM") image of this sample is shown in FIG. 24. FIG. 25 shows the adsorption isotherms of ZIF-11 for carbon dioxide, $CO_2$, and methane, $CH_4$, at 301 K. The ordinate displays the equilibrium adsorption loading in typical units of mmole/g. The abscissa displays the absolute pressure of the adsorbate in kPa. As can be seen from FIG. 25, at the upper test pressure of 106.6 kPa@301 K, the adsorption loading of carbon dioxide, $CO_2$, was higher than the adsorption loading for methane, $CH_4$, on the ZIF-11 material.

Figure 26:
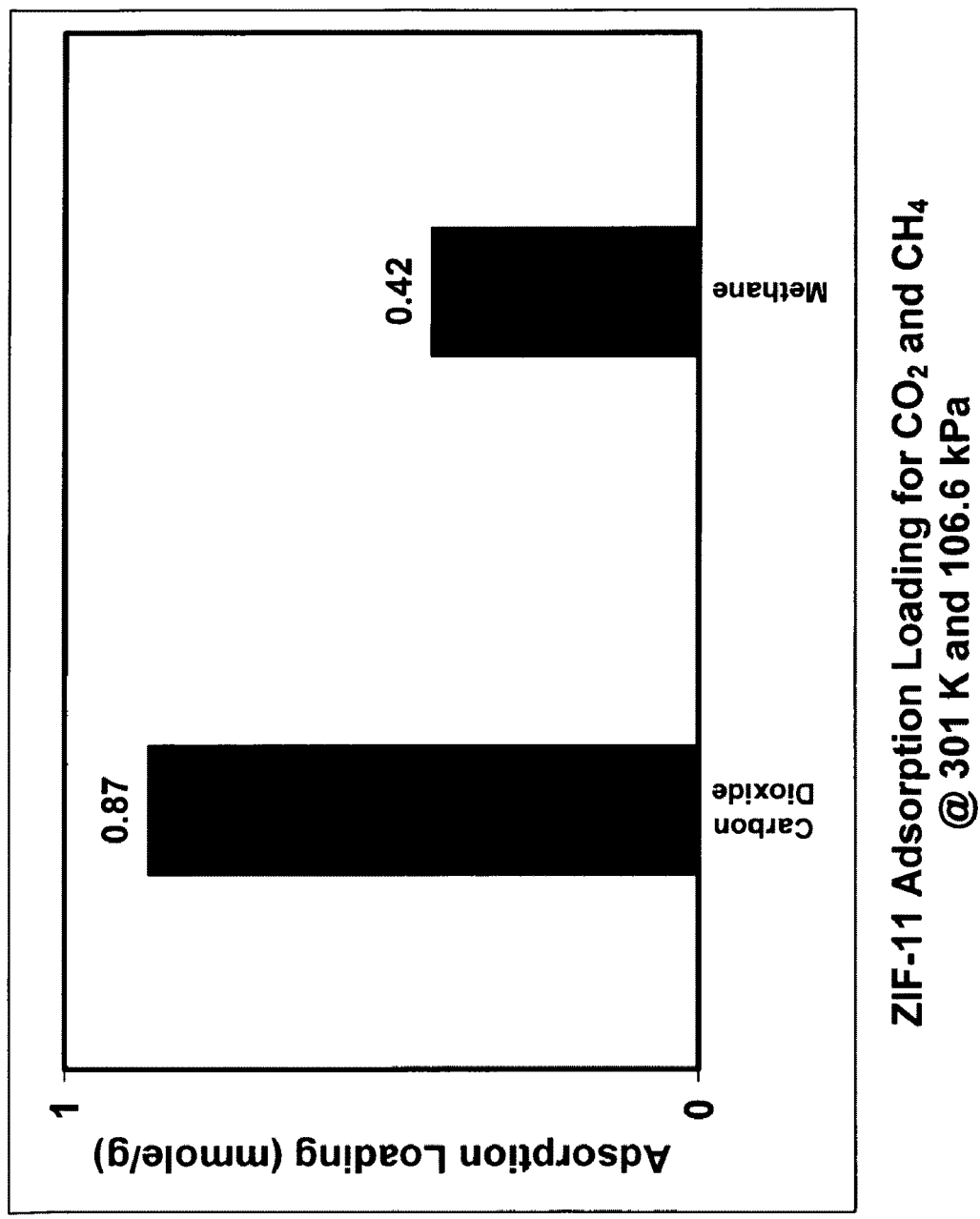
FIG. 26 is a bar graph comparing the adsorption loadings of a ZIF-11 sample of Example 9 for $CO_2$ and $CH_4$ at 301 K and 106.6 kPa.

FIG. 26 is a bar graph comparing the corresponding adsorption loadings of the ZIF-11 material for carbon dioxide, $CO_2$, and methane, $CH_4$, at test conditions of 301 K and 106.6 kPa obtained from the tests above. As can be seen from this bar graph, the adsorption loading of the ZIF-11 material for $CO_2$ at 106.6 kPa@301 K was approximately 0.87 mmole/g while the adsorption loading for $CH_4$ was approximately 0.42 mmole/g. However, at these conditions, the adsorptive loading ration for $CO_2$ over $CH_4$ was only approximately 2.1. This example illustrates that ZIF-11 does not possess an adsorptive loading ratio high enough to meet the requirements of the present invention.

Example 10

In this example, adsorption isotherm experiments were carried out on ZIF-8 samples obtained from the synthesis detailed in Example 5 above in compliance with the general testing procedures for Examples 6-10 described above.

Figure 28:
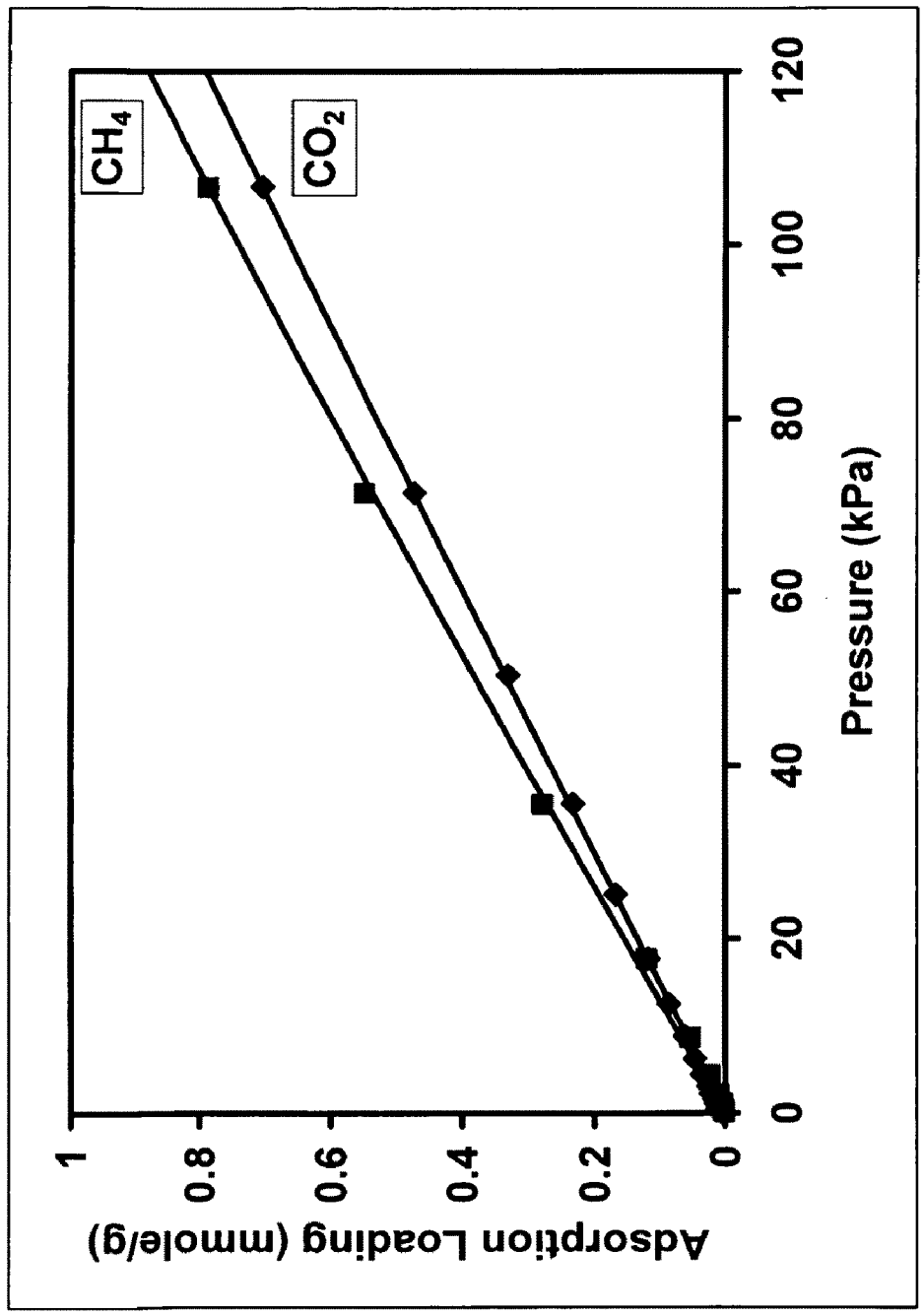
FIG. 28 shows the $CO_2$ adsorption isotherm and the $CH_4$ adsorption isotherm at 301 K for a ZIF-8 sample of Example 10.

For the testing of each absorbate in this experiment, a sample of ZIF-8 was loaded with methanol as the solvent. It was out-gassed for 2 hrs at 301 K under dynamic vacuum, heated to 523 K for 3 hrs, and then cooled to 301 K. The dry weight was 16.37 mg. The same clean-up procedure was applied to ZIF-8 prior to all subsequent experiments with other adsorbates. A Scanning Electron Microscopy ("SEM") image of this sample is shown in FIG. 27. FIG. 28 shows the adsorption isotherms of ZIF-8 for carbon dioxide, $CO_2$, and methane, $CH_4$, at 301 K. The ordinate displays the equilibrium adsorption loading in typical units of mmole/g. The abscissa displays the absolute pressure of the adsorbate in kPa. As can be seen from FIG. 28, at the upper test pressure of 106.6 kPa@301 K, there was not a significant difference in the adsorption loading of carbon dioxide, $CO_2$, as compared to the adsorption loading for methane, $CH_4$, on the ZIF-8 material. In fact, in contrast to the other ZIF materials tested, the adsorption loading on the ZIF-8 material was lower for $CO_2$ than for $CH_4$.

Figure 29:
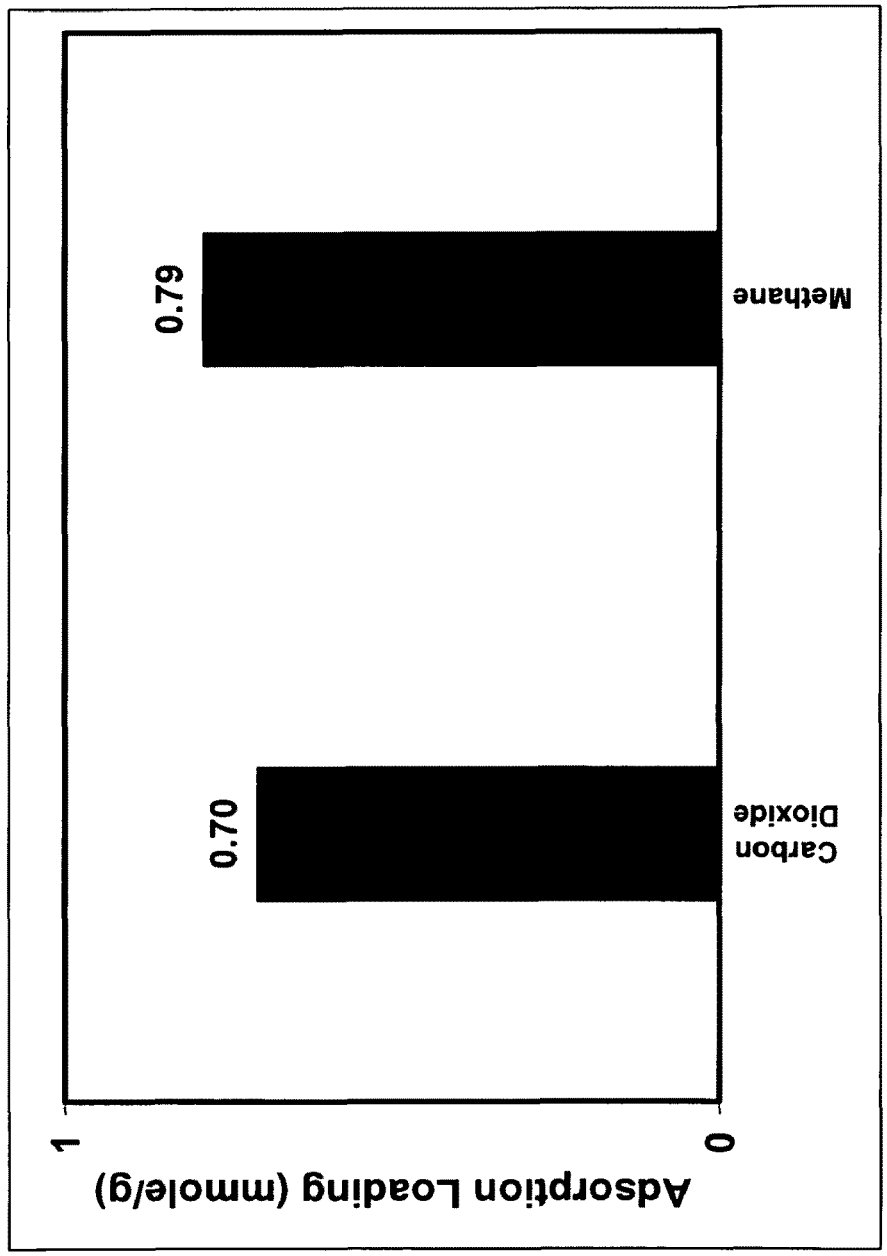
FIG. 29 is a bar graph comparing the adsorption loadings of a ZIF-8 sample of Example 10 for $CO_2$ and $CH_4$ at 301 K and 106.6 kPa.

FIG. 29 is a bar graph comparing the corresponding adsorption loadings of the ZIF-8 material for carbon dioxide, $CO_2$, and methane, $CH_4$, at test conditions of 301 K and 106.6 kPa obtained from the tests above. As can be seen from this bar graph, the adsorption loading of the ZIF-8 material for $CO_2$ at 106.6 kPa@301 K was approximately 0.70 mmole/g while the adsorption loading for $CH_4$ was approximately 0.79 mmole/g. At these conditions, the adsorptive loading ratio for $CO_2$ over $CH_4$ is approximately 0.9. This example illustrates that ZIF-8 does not possess an adsorptive loading ratio high enough to meet the requirements of the present invention.

What is claimed is:

1. A process for separating $CO_2$ from a process feedstream, comprising:
   a) contacting an adsorbent bed comprised of a zeolitic imidazolate framework material with a process feedstream comprising $CO_2$ and $CH_4$ at a first pressure and first temperature;
   b) adsorbing at least a portion of the $CO_2$ in the adsorbent bed, thereby producing a $CO_2$-lean product stream, wherein the $CO_2$-lean product stream has a lower concentration of $CO_2$ by vol % than the process feedstream; and
   c) producing a $CO_2$-rich product stream at a second pressure and second temperature, wherein the $CO_2$-rich product stream has a higher concentration of $CO_2$ by vol % than the process feedstream;
   wherein the zeolitic imidazolate framework material has a framework structure wherein each vertex of the framework structure is comprised of a single metal ion and each pair of connected adjacent vertices of the framework structure is linked by nitrogen atoms of an imidazolate anion or its derivative, and wherein the zeolitic imidazolate framework material has an adsorptive loading ratio for $CO_2$ over $CH_4$ of at least 10; and the adsorptive loading ratio for $CO_2$ over $CH_4$ is measured at 301 K and 106.6 kPa.

2. The process of claim 1, wherein the $CO_2$ partial pressure in step a) is greater than the $CO_2$ partial pressure in step d).

3. The process of claim 1, wherein the first pressure is greater than the second pressure.

4. The process of claim 2, wherein the second temperature is greater than the first temperature.

5. The process of claim 2, wherein the steps of the process are part of a rapid cycle swing adsorption process and the cycle time of the rapid cycle swing adsorption process is less than about 1 minute.

6. The process of claim 2, wherein the process is a swing adsorption process and the difference between the maximum and minimum $CO_2$ partial pressures achieved in the adsorbent bed during a cycle is less than 300 kPa.

7. The process of claim 2, wherein the $CO_2$ partial pressure of the process feedstream in step a) is less than about 200 kPa.

8. The process of claim 1, wherein the process feedstream is comprised of a natural gas.

9. The process of claim 8, wherein at least a portion of the $CO_2$-lean product stream is utilized to make a final natural gas product.

10. The process of claim 8, wherein the process feedstream has a $CO_2$ content of at least about 10 vol % and the $CO_2$-lean product stream has a $CO_2$ content of less than about 5 vol %.

11. The process of claim 10, wherein the pressure of the process feedstream is at least 500 psig.

12. The process of claim 11, wherein the pressure of the $CO_2$-lean product stream is at least 250 psig.

13. The process of claim 1, wherein the process feedstream is comprised of a synthetically produced gas and the $CO_2$-lean product stream has a $CO_2$ content of less than 5 vol %.

14. The process of claim 1, wherein the process feedstream is comprised of an organically derived gas stream selected from a landfill produced gas and a biogenically produced gas.

15. The process of claim 14, wherein the $CO_2$ partial pressure of the process feedstream in step a) is less than about 200 kPa.

16. The process of claim 14, wherein the temperature of the organically derived gas stream is reduced prior to contacting the adsorbent bed in step a).

17. The process of claim 14, wherein the process feedstream contacts the adsorbent bed at a pressure of less than about 50 psig.

18. The process of claim 17, wherein the second temperature is greater than the first temperature.

19. A process for separating $CO_2$ from a process feedstream, comprising:
   a) contacting an adsorbent bed comprised of a zeolitic imidazolate framework material with a process feedstream comprising $CO_2$ and $CH_4$ at a first pressure and first temperature;
   b) adsorbing at least a portion of the $CO_2$ in the adsorbent bed, thereby producing a $CO_2$-lean product stream, wherein the $CO_2$-lean product stream has a lower concentration of $CO_2$ by vol % than the process feedstream; and
   c) producing a $CO_2$-rich product stream at a second pressure and second temperature, wherein the $CO_2$-rich product stream has a higher concentration of $CO_2$ by vol % than the process feedstream;
   wherein the zeolitic imidazolate framework material has a framework structure wherein each vertex of the framework structure is comprised of a single metal ion and each pair of connected adjacent vertices of the framework structure is linked by nitrogen atoms of an imidazolate anion or its derivative, and wherein the zeolitic imidazolate framework material has an adsorptive loading ratio for $CO_2$ over $CH_4$ of at least 10; and the process feedstream is comprised of a natural gas and at least a portion of the $CO_2$-rich product stream is sequestered at a pressure of at least 500 psig.

20. A process for separating $CO_2$ from a process feedstream, comprising:
   a) contacting an adsorbent bed comprised of a zeolitic imidazolate framework material with a process feedstream comprising $CO_2$ and $CH_4$ at a first pressure and first temperature;

b) adsorbing at least a portion of the $CO_2$ in the adsorbent bed, thereby producing a $CO_2$-lean product stream, wherein the $CO_2$-lean product stream has a lower concentration of $CO_2$ by vol % than the process feedstream; and
c) producing a $CO_2$-rich product stream at a second pressure and second temperature, wherein the $CO_2$-rich product stream has a higher concentration of $CO_2$ by vol % than the process feedstream;
wherein the zeolitic imidazolate framework material has a framework structure wherein each vertex of the framework structure is comprised of a single metal ion and each pair of connected adjacent vertices of the framework structure is linked by nitrogen atoms of an imidazolate anion or its derivative, and wherein the zeolitic imidazolate framework material has an adsorptive loading ratio for $CO_2$ over $CH_4$ of at least 10, wherein the adsorptive loading ratio for $CO_2$ over $CH_4$ is measured at 301 K and 106.6 kPa; and the process feedstream is comprised of an organically derived gas stream selected from a landfill produced gas and a biogenically produced gas; and the process feedstream contacts the adsorbent bed at a pressure of less than about 50 psig.

21. The process of claim 20, wherein the zeolitic imidazolate framework material is selected from the group consisting of ZIF-7 and ZIF-9.

* * * * *

UNITED STATES PATENT AND TRADEMARK OFFICE
CERTIFICATE OF CORRECTION

PATENT NO. : 8,142,746 B2  
APPLICATION NO. : 12/321752  
DATED : March 27, 2012  
INVENTOR(S) : Sebastian C. Reyes et al.

Page 1 of 1

It is certified that error appears in the above-identified patent and that said Letters Patent is hereby corrected as shown below:

In the Claims

- Column 31, line 59, claim 2: replace "step d)" with "step c)"

Signed and Sealed this
Second Day of December, 2014

Michelle K. Lee
*Deputy Director of the United States Patent and Trademark Office*